United States Patent
Esquerré et al.

(10) Patent No.: US 9,902,947 B2
(45) Date of Patent: Feb. 27, 2018

(54) CYAA-CARRIED POLYPEPTIDE(S) AND USE TO INDUCE BOTH THERAPEUTIC AND PROPHYLACTIC IMMUNE RESPONSES

(75) Inventors: Michael Esquerré, Toulouse (FR); Marie Momot, Toulouse (FR); Anne Goubier, Sauveterre de Bearn (FR); Yolande Misseri, Dremil-Lafage (FR)

(73) Assignee: GENTICEL, Labege (FR)

( * ) Notice: Subject to any disclaimer, the term of this patent is extended or adjusted under 35 U.S.C. 154(b) by 0 days.

(21) Appl. No.: 13/981,250

(22) PCT Filed: Jan. 24, 2012

(86) PCT No.: PCT/EP2012/051027
§ 371 (c)(1),
(2), (4) Date: Oct. 8, 2013

(87) PCT Pub. No.: WO2012/101112
PCT Pub. Date: Aug. 2, 2012

(65) Prior Publication Data
US 2014/0037670 A1 Feb. 6, 2014

(30) Foreign Application Priority Data
Jan. 24, 2011 (EP) .................................. 11305069

(51) Int. Cl.
C12N 9/88 (2006.01)
A61K 39/00 (2006.01)
A61K 39/12 (2006.01)
A61K 39/39 (2006.01)

(52) U.S. Cl.
CPC ............ *C12N 9/88* (2013.01); *A61K 39/0011* (2013.01); *A61K 39/12* (2013.01); *A61K 39/39* (2013.01); *A61K 2039/55511* (2013.01); *A61K 2039/55561* (2013.01); *A61K 2039/585* (2013.01); *A61K 2039/6037* (2013.01); *A61K 2039/70* (2013.01); *C07K 2319/33* (2013.01); *C07K 2319/40* (2013.01); *C12N 2710/20034* (2013.01)

(58) Field of Classification Search
None
See application file for complete search history.

(56) References Cited

U.S. PATENT DOCUMENTS

2007/0072266 A1* 3/2007 Preville et al. .............. 435/69.1

FOREIGN PATENT DOCUMENTS

| EP | 1576967 B1 | 9/2007 |
|---|---|---|
| EP | 1 894 941 A1 | 3/2008 |
| WO | WO 2005/053738 A1 | 6/2005 |
| WO | WO 2008/025848 A2 | 3/2008 |
| WO | WO 2008/026071 A2 | 3/2008 |

OTHER PUBLICATIONS

Baldwin et al. (Clin Cancer Res. Nov. 1, 2003;9(14):5205-13).*
Van de Loo et al. (Proc. Natl. Acad. Sci 1995).*
Broun et al. (Science 1998).*
Fayolle et al., "Delivery of Multiple Epitopes by Recombinant Detoxified Adenylate Cyclase of Bordetella pertussis Indues Protective Antiviral Immunity", Journal of Virology, vol. 75, No. 16 (2001) pp. 7330-7338.
Guermonprez et al., "In vivo receptor-mediated delivery of a recombinant invasive bacterial toxoid to CD11c+CD8α-CD11bhigh dendritic cells", Eur. J. Immunol., vol. 32 (2002) pp. 3071-3081.
International Search Report issued in PCT/EP2012/051027 dated Mar. 7, 2012.
Mascarell et al., "Delivery of the HIV-1 Tat protein to dendritic cells by the CyaA vector induces specific Th1 response and high affinity meutralizing antibodies in non human primates". Vaccine. vol. 24 (2006) pp. 3490-3499.
Preville et al., "Eradication of Established Tumors by Vaccination with Recombinant Bordetella pertussis Adenylate Cyclase Carrying the Human Papillomavirus 16 E7 Oncoprotein", Cancer Res., vol. 65, No. 2 (2005) pp. 641-649.
Berraondo et al., "Eradication of Large Tumors in Mice by a Tritherapy Targeting the Innate, Adaptive, and Regulatory Components of the Immune System," Cancer Research, vol. 67, No. 18, Sep. 15, 2007, pp. 8847-8855.
Schlecht et al., "Antigen Targeting to CD11b Allows Efficient Presentation of CD4+ and CD8+ T Cell Epitopes and In Vivo Th1-Polarized T Cell Priming," The Journal of Immunology, vol. 173, 2004, pp. 6089-6097.

* cited by examiner

*Primary Examiner* — J. Hines
*Assistant Examiner* — Khatol Shahnan Shah
(74) *Attorney, Agent, or Firm* — Birch, Stewart, Kolasch & Birch, LLP

(57) ABSTRACT

The invention is directed to means, based on CyaA-carried polypeptide(s), for use in the immunotherapeutic treatment of first determined pathological condition(s) diagnosed in a mammalian host by eliciting a T cell immune response against a first group of epitopes contained in said polypeptide(s) and in the prophylaxis against second determined pathological condition(s) in the same mammalian host by eliciting a T cell memory immune response against a second group of epitopes contained in said polypeptide(s), said immune responses being obtained after administration of said vector-carried polypeptide(s) into said host, wherein said prophylaxis against second determined pathological condition(s) is not observed when said second group of epitopes is not contained in said administered vector-carried polypeptide(s).

29 Claims, 22 Drawing Sheets

B. pertussis [NP_879578.1]
MQQSHQAGYANAADRESGIPAAVLDGIKAVAKEKNATLMFRLVNPHSTSLIAEGVATKGLGVHAKSSDWG
LQAGYIPVNPNLSKLFGRAPEVIARADNDVNSSLAHGHTAVDLTLSKERLDYLRQAGLVTGMADGVVASN
HAGYEQFEFRVKETSDGRYAVQYRRKGGDDFEAVKVIGNAAGIPLTADIDMFAIMPHLSNFRDSARSSVT
SGDSVTDYLARTRRAASEATGGLDRERIDLLWKIARAGARSAVGTEARRQFRYDGDMNIGVITDFELEVR
NALNRRAHAVGAQDVVQHGTEQNNPFPEADEKIFVVSATGESQMLTRGQLKEYIGQQRGEGYVFYENRAY
GVAGKSLFDDGLGAAPGVPSGRSKFSPDVLETVPASPGLRRPSLGAVERQDSGYDSLDGVGSRSFSLGEV
SDMAAVEAAELEMTRQVLHAGARQDDAEPGVSGASAHWGQRALQGAQAVAAAQRLVHAIALMTQFGRAGS
TNTPQEAASLSAAVFGLGEASSAVAETVSGFFRGSSRWAGGFGVAGGAMALGGGIAAAVGAGMSLTDDAP
AGGQKAAAGAEIALQLTGGTVELASSIALALAAARGVTSGLQVAGASAGAAAGALAAALSPMEIYGLVQQS
HYADQLDKLAQESSAYGYEGDALLAQLYRDKTAAEGAVAGVSAVLSTVGAAVSIAAAASVVGAPVAVVTS
LLTGALNGILRGVQQPIIEKLANDYARKIDELGGPQAYFEKNLQARHEQLANSDGLRKMLADLQAGWNAS
SVIGVQTTEISKSALELAAITGNADNLKSVDVFVDRFVQGERVAGQPVVLDVAAGGIDIASRKGERPALT
FITPLAAPGEEQRRRTKTGKSEFTTFVEIVGKQDRWRIRDGAADTTIDLAKVVSQLVDANGVLKHSIKLD
VIGGDGDDVVLANASRIHYDGGAGTNTVSYAALGRQDSITVSADGERFNVRKQLNNANVYREGVATQTTA
YGKRTENVQYRHVELARVGQLVEVDTLEHVQHIIGGAGNDSITGNAHDNFLAGGSGDDRLDGGAGNDTLV
GGEGQNTVIGGAGDDVFLQDLGVWSNQLDGGAGVDTVKYNVHQPSEERLERMGDTGIHADLQKGTVEKWP
ALNLFSVDHVKNIENLHGSRLNDRIAGDDQDNELWGHDGNDTIRGRGGDDILRGGLGLDTLYGEDGNDIF
LQDDETVSDDIDGGAGLDTVDYSAMIHPGRIVAPHEYGFGIEADLSREWVRKASALGVDYYDNVRNVENV
IGTSMKDVLIGDAQANTLMGQGGDDTVRGGDGDDLLFGGDGNDMLYGDAGNDTLYGGLGDDTLEGGAGND
WFGQTQAREHDVLRGGDGVDTVDYSQTGAHAGIAAGRIGLGILADLGAGRVDKLGEAGSSAYDTVSGIEN
VVGTELADRITGDAQANVLRGAGGADVLAGGEGDDVLLGGDGDDQLSGDAGRDRLYGEAGDDWFFQDAAN
AGNLLDGGDGRDTVDFSGPGRGLDAGAKGVFLSLGKGFASLMDEPETSNVLRNIENAVGSARDDVLIGDA
GANVLNGLAGNDVLSGGAGDDVLLGDEGSDLLSGDAGNDDLFGGQGDDTYLFGVGYGHDTIYESGGGHDT
IRINAGADQLWFARQGNDLEIRILGTDDALTVHDWYRDADHRVEIIHAANQAVDQAGIEKLVEAMAQYPD
PGAAAAAPPAARVPDTLMQSLAVNWR (SEQ ID NO :1)

B. parapertussis [NP_882677.1]
MLDVWFLQKDEVLSATHRLRRCESVQSTTYRQIHMQQSHQAGYANAADRESGIPAAVLDGIKAVAKEKNA
TLMFRLVNPHSTSLIAEGVATKGLGVHAKSSDWGLQAGYIPVNPNLSKLFGRAPEVIARADNDVNSSLAH
GHTAVDLTLSKERLDYLRQAGLVTGMADGVVASNHAGYEQFEFRVKETSDGRYAVQYRRKGGDDFEAVKV
IGNAAGIPLTADIDMFAIMPHLSNFRDSARSSVTSGDSVTDYLARTRRAASEATGGLDRERIDLLWKIAR
AGARSAVGTEARRQFRYDGDMNIGVITDFELEVRNALNRRAHAVGAQDVVQHGTEQNNPFPEADEKIFVV
SATGESQMLTRGQLKEYIGQQRGEGYVFYENRAYGVAGKSLFDDGLGAAPGVPGGRSKSSPDVLETVPAS
PGLRRPSLGAVERQDSGYDSLDGVGSRSFSLGEVSDMAAVEAAELEMTRQVLHAGARQDDAEPGVSGASA
HWGQRALQGAQAVAAAQRLVHAIALMTQFGRAGSTNTPQEAASLSAAVFGLGEASSAVAETVSGFFRGSS
RWAGGFGVAGGAMALGGGIAAAVGAGMSLTDDAPAGQKAAVGAEIALQLTGGTVELASSIALALAAARGV
TSGLQVAGASAGAAAGALAAALSPMEIYGLVQQSHYADQLDKLAQESSAYGYEGDALLAQLYRDKTAAEG
AVAGVSAVLSTVGAAVSIAAAASVVGAPVAVVTSLLTGALNGILRGVQQPIIEKLANDYARKIDELGGPQ
AYFEKNLQARHEQLANSDGLRKMLADLQAGWNASSVIGVQTTEISKSALELAAITGNADNLKSADVFVDR
FIQGERVAGQPVVLDVAAGGIDIASRKGERPALTFITPLAAPGEEQRRRTKTGKSEFTTFVEIVGKQDRW
RIRDGAADTTIDLAKVVSQLVDANGVLKHSIKLEVIGGDGDDVVLANASRIHYDGGAGTNTVSYAALGRQ
DSITVSADGERFNVRKQLNNANVYREGVATQKTAYGKRTENVQYRHVELARVGQLVEVDTLEHVQHIIGG
AGNDSITGNAHDNFLAGGAGDDRLDGGAGNDTLVGGEGHNTVVGGAGDDVFLQDLGVWSNQLDGGAGVDT
VKYNVHQPSEERLERMGDTGIHADLQKGTVEKWPALNLFSVDHVKNIENLHGSSLNDSIAGDDRDNELWG
DDGNDTIHGRGGDDILRGGLGLDTLYGEDGNDIFLQDDETVSDDIDGGAGLDTVDYSAMIHAGKIVAPHE
YGFGIEADLSEGWVRKAARRGMGYYDSVRSVENVIGTSMKDVLIGDAQANTLMGQGGDDTVRGGDGDDLL
FGGDGNDMLYGDAGNDTLYGGLGDDTLEGGAGNDWFGQTPAREHDVLRGGAGVDTVDYSQAGAHAGVATG
RIGLGILADLGAGRVDKLGEAGSSAYDTVSGIENVVGTELADRITGDAQANVLRGAGGADVLAGGEGDDV
LLGGEGDDQLSGDAGRDRLYGEAGDDWFFQDAANAGNLLDGGDGNDTVDFSGPGRGLDAGAKGVFLSLGK
GFASLMDEPETSNVLRHIENAVGSVRDDVLIGDAGANVLNGLAGNDVLSGGAGDDVLLGDEGSDLLSGDA
GNDDLFGGQGDDTYLFGAGYGHDTIYESGGGHDTIRINAGADQLWFARQGNDLEIRILGTDDALTVHDWY
RDADHRVEAIHAANQAIDPAGIEKLVEAMAQYPDPGAAAAAPPAARVPDTLMQSLAVNWR (SEQ ID NO :2)

Fig. 1A

B. bronchiseptica [NP_886873.1]
MLDVWFLQKDEVLSATHRLRRCESVQSTTYRQIHMQQSHQAGYANAADRESGIPAAVLDGIKAVAKEKNA
TLMFRLVNPHSTSLIAEGVATKGLGVHAKSSDWGLQAGYIPVNPNLSKLFGRAPEVIARADNDVNSSLAH
GHTAVDLTLSKERLDYLRQAGLVTGMADGVVASNHAGYEQFEFRVKETSDGRYAVQYRRKGGDDFEAVKV
IGNAAGIPLTADIDMFAIMPHLSNFRDSARSSVTSGDSVTDYLARTRRAASEATGGLDRERIDLLWKIAR
AGARSAVGTEARRQFRYDGDMNIGVITDFELEVRNALNRRAHAVGAQDVVQHGTEQNNPFPEADEKIFVV
SATGESQMLTRGQLKEYIGQQRGEGYVFYENRAYGVAGKSLFDDGLGAAPGVPGGRSKSSPDVLETVPAS
PGLRRPSLGAVERQDSGYDSLDGVGSRSFSLGEVSDMAAVEAAELEMTRQVLHAGARQDDAEPGVSGASA
HWGQRALQGAQAVAAAQRLVHAIALMTQFGRAGSTNTPQEAASLSAAVFGLGEASSAVAETVSGFFRGSS
RWAGGFGVAGGAMALGGGIAAAVGAGMSLTDDAPAGQKAAAGAEIALQLTGGTVELASSIALALAAARGV
TSGLQVAGASAGAAAGALAAALSPMEIYGLVQQSHYADQLDKLAQESSAYGYEGDALLAQLYRDKTAAEG
AVAGVSAVLSTVGAAVSIAAAASVVGAPVAVVTSLLTGALNGILRGVQQPIIEKLANDYARKIDELGGPQ
AYFEKNLQARHEQLANSDGLRKMLADLQAGWNASSVIGVQTTEISKSALELAAITGNADNLKSADVFVDR
FIQGERVAGQPVVLDVAAGGIDIASRKGERPALTFITPLAAPGEEQRRRTKTGKSEFTTFVEIVGKQDRW
RIRDGAADTTIDLAKVVSQLVDANGVLKHSIKLEVIGGDGDDVVLANASRIHYDGGAGTNTVSYAALGRQ
DSITVSADGERFNVRKQLNNANVYREGVATQKTAYGKRTENVQYRHVELARVGQLVEVDTLEHVQHIIGG
AGNDSITGNAHDNFLAGGAGDDRLDGGAGNDTLVGGEGHNTVVGGAGDDVFLQDLGVWSNQLDGGAGVDT
VKYNVHQPSEERLERMGDTGIHADLQKGTVEKWPALNLFSVDHVKNIENLHGSSLNDSIAGDDRDNELWG
DDGNDTIHGRGGDDILRGGLGLDTLYGEDGNDIFLQDDETVSDDIDGGAGLDTVDYSAMIHAGKIVAPHE
YGFGIEADLSEGWVRKAARRGMDYYDSVRSVENVIGTSMKDVLIGDAQANTLMGQGGDDTVRGGDGDDLL
FGGDGNDMLYGDAGNDTLYGGLGDDTLEGGAGNDWFGQTPAREHDVLRGGAGVDTVDYSQAGAHAGVATG
RIGLGILADLGAGRVDKLGEAGSSAYDTVSGIENVVGTELADRITGDAQANVLRGAGGADVLAGGEGDDV
LLGGDGDDQLSGDAGRDRLYGEAGDDWFFQDAANAGNLLDGGDGNDTVDFSGPGRGLDAGAKGVFLSLGK
GFASLMDEPETSNVLRHIENAVGSVRDDVLIGDAGANVLNGLAGNDVLSGGAGDDVLLGDEGSDLLSGDA
GNDDLFGGQGDDTYLFGAGYGHDTIYESGGGHDTIRINAGADQLWFARQGNDLEIRILGTDDALTVHDWY
RDADHRVEAIHAANQAIDPAGIEKLVEAMAQYDPGAAAAAPPAARVPDTLMQSLAVNWR (SEQ ID NO :3)

Fig. 1B

*B. pertussis*
ATGCAGCAATCGCATCAGGCTGGTTACGCAAACGCCGCCGACCGGGAGTCTGGCATCCCCGCAGCCGTAC
TCGATGGCATCAAGGCCGTGGCGAAGGAAAAAAACGCCACATTGATGTTCCGCCTGGTCAACCCCCATTC
CACCAGCCTGATTGCCGAAGGGGTGGCCACCAAAGGATTGGGCGTGCACGCCAAGTCGTCCGATTGGGGG
TTGCAGGCGGGCTACATTCCCGTCAACCCGAATCTTTCCAAACTGTTCGGCCGTGCGCCCGAGGTGATCG
CGCGGGCCGACAACGACGTCAACAGCAGCCTGGCGCATGGCCATACCGCGGTCGACCTGACGCTGTCGAA
AGAGCGGCTTGACTATCTGCGGCAAGCGGGCCTGGTCACCGGCATGGCCGATGGCGTGGTCGCGAGCAAC
CACGCAGGCTACGAGCAGTTCGAGTTTCGCGTGAAGGAAACCTCGGACGGGCGCTATGCCGTGCAGTATC
GCCGCAAGGGCGGCGACGATTTCGAGGCGGTCAAGGTGATCGGCAATGCCGCCGGTATTCCACTGACGGC
GGATATCGACATGTTCGCCATTATGCCGCATCTGTCCAACTTCCGCGACTCGGCGCGCAGTTCGGTGACC
AGCGGCGATTCGGTGACCGATTACCTGGCGCGCACGCGGCGGGCCGCCAGCGAGGCCACGGGCGGCCTGG
ATCGCGAACGCATCGACTTGTTGTGGAAAATCGCTCGCGCCGGCGCCCGTTCCGCAGTGGGCACCGAGGC
GCGTCGCCAGTTCCGCTACGACGGCGACATGAATATCGGCGTGATCACCGATTTCGAGCTGGAAGTGCGC
AATGCGCTGAACAGGCGGGCGCACGCCGTCGGCGCGCAGGACGTGGTCCAGCATGGCACTGAGCAGAACA
ATCCTTTCCCGGAGGCAGATGAGAAGATTTCGTCGTATCGGCCACCGGTGAAAGCCAGATGCTCACGCG
CGGGCAACTGAAGGAATACATTGGCCAGCAGCGCGGCGAGGGCTATGTCTTCTACGAGAACCGTGCATAC
GGCGTGGCGGGGAAAAGCCTGTTCGACGATGGGCTGGGAGCCGCGCCCGGCGTGCCGAGCGGACGTTCGA
AGTTCTCGCCGGATGTACTGGAAACGGTGCCGGCGTCACCCGGATTGCGGCGGCCGTCGCTGGGCGCAGT
GGAACGCCAGGATTCCGGCTATGACAGCCTTGATGGGGTGGGATCGCGATCGTTCTCGTTGGGCGAGGTG
TCCGACATGGCCGCCGTGGAAGCGGCGGAACTGGAAATGACCCGGCAAGTCTTGCACGCCGGGGCGCGGC
AGGACGATGCCGAGCCGGGCGTGAGCGGTGCGTCGGCGCACTGGGGGCAGCGGGCGCTGCAGGGCGCCCA
GGCGGTGGCGGCGGCGCAGCGGCTGGTTCATGCCATTGCCCTGATGACGCAATTCGGCCGGGCCGGTTCC
ACCAACACGCCGCAGGAAGCGGCCTCGTTGTCGGCGGCCGTGTTCGGCTTGGGCGAGGCCAGCAGCGCCG
TGGCCGAAACCGTGAGCGGTTTTTTCCGCGGGTCTTCGCGCTGGGCCGGCGGTTTCGGCGTGGCTGGCGG
CGCGATGGCGCTGGGAGGCGGCATCGCCGCGGCCGTTGGCGCCGGGATGTCGTTGACCGATGACGCGCCG
GCCGGACAGAAGGCCGCCGCCGGCGCCGAGATCGCGCTGCAGTTGACAGGTGGAACGGTCGAGCTGGCTT
CTTCCATCGCGTTGGCGCTGGCCGCGGCGCGCGGCGTGACCAGCGGCTTGCAGGTGGCCGGGGCGTCGGC
CGGGGCGGCTGCCGGCGCATTGGCCGCGGCGCTCAGTCCCATGGAGATCTACGGCCTGGTGCAGCAATCG
CACTATGCGGATCAGCTGGACAAGCTGGCGCAGGAATCGAGCGCATACGGTTACGAGGGCGACGCCTTGC
TGGCCCAGCTGTATCGCGACAAGACGGCCGCCGAGGGCGCCGTCGCCGGCGTCTCCGCCGTCCTGAGCAC
GGTGGGGGCGGCGGTGTCGATCGCCGCGGCGGCCAGCGTGGTAGGGGCCCCGGTGGCGGTGGTCACTTCC
TTGCTGACCGGGGCTCTCAACGGCATCCTGCGCGGCGTGCAGCAGCCCATCATCGAAAAGCTGGCCAACG
ATTACGCTCGCAAGATCGACGAGCTGGGCGGGCCGCAAGCGTACTTCGAGAAAAACCTGCAGGCGCGTCA
CGAACAACTGGCCAATTCGGACGGCCTACGGAAAATGCTGGCCGACCTGCAGGCCGGTTGGAACGCCAGC
AGCGTGATCGGGGTGCAGACGACAGAGATCTCCAAGTCGGCGCTCGAACTGGCCGCCATTACCGGCAACG
CGGACAACCTGAAATCCGTCGACGTGTTCGTGGACCGCTTCGTCCAGGGCGAGCGGGTGGCCGGCCAGCC
GGTGGTCCTCGACGTCGCCGCCGGCGGCATCGATATCGCCAGCCGCAAGGGCGAGCGGCCGGCGCTGACG
TTCATCACGCCGCTGGCCGCGCCAGGAGAAGAGCAGCGCCGGCGCACGAAAACGGGCAAGAGCGAATTCA
CCACATTCGTCGAGATCGTGGGCAAGCAGGACCGCTGGCGCATCCGGGACGGCGCGGCCGACACCACCAT
CGATCTGGCCAAGGTGGTGTCGCAACTGGTCGACGCCAATGGCGTGCTCAAGCACAGCATCAAACTGGAT
GTGATCGGCGGAGATGGCGATGACGTCGTGCTTGCCAATGCTTCGCGCATCCATTATGACGGCGGCGCGG
GCACCAACACGGTCAGCTATGCCGCCCTGGGTCGACAGGATTCCATTACCGTGTCCGCCGACGGGGAACG
TTTCAACGTGCGCAAGCAGTTGAACAACGCCAACGTGTATCGCGAAGGCGTGGCTACCCAGACAACCGCC
TACGGCAAGCGCACGGAGAATGTCCAATACCGCCATGTCGAGCTGGCCCGTGTCGGGCAACTGGTGGAGG
TCGACACGCTCGAGCATGTGCAGCACATCATCGGCGGGCCGGCAACGATTCGATCACCGGCAATGCGCA
CGACAACTTCCTAGCCGGCGGGTCGGGCGACGACAGGCTGGATGGCGGCGCCGGCAACGACACCCTGGTT
GGCGGCGAGGGCCAAAACACGGTCATCGGCGGCGCCGGCGACGACGTATTCCTGCAGGACCTGGGGGTAT
GGAGCAACCAGCTCGATGGCGGCGCGGGCGTCGATACCGTGAAGTACAACGTGCACCAGCCTTCCGAGGA
GCGCCTCGAACGCATGGGCGACACGGGCATCCATGCCGATCTTCAAAAGGGCACGGTCGAGAAGTGGCCG
GCCCTGAACCTGTTCAGCGTCGACCATGTCAAGAATATCGAGAATCTGCACGGCTCCCGCCTGAACGACC
GCATCGCCGGCGACGACCAGGACAACGAGCTCTGGGGCCACGATGGCAACGACACGATACGCGGCCGGGG
CGGCGACGACATCCTGCGCGGCGGCCTGGGCCTGGACACGCTGTATGGCGAGGACGGCAACGACATCTTC
CTGCAGGACGACGAGACCGTCAGCGATGACATCGACGGCGGCGCGGGCTGGACACCGTCGACTACTCCG
CCATGATCCATCCAGGCAGGATCGTTGCGCCGCATGAATACGGCTTCGGGATCGAGGCGGACCTGTCCAG
GGAATGGGTGCGCAAGGCGTCCGCGCTGGGCGTGGACTATTACGATAATGTCCGCAATGTCGAAAACGTC
ATCGGTACGAGCATGAAGGATGTGCTCATCGGCGACGCGCAAGCCAATACCCTGATGGGCCAGGGCGGCG
ACGATACCGTGCGCGGCGGCGACGGCGATGATCTGCTGTTCGGCGGCGACGGCAACGACATGCTGTATGG
CGACGCCGGCAACGACACCCTCTACGGGGGGCTGGGCGACGATACCCTTGAAGGCGGCGCGGGCAACGAT
TGGTTCGGCCAGACGCAGGCGCGCGAGCATGACGTGCTGCGCGGCGGAGATGGGGTGGATACCGTCGATT

Fig. 1C (*B. pertussis*/continued)
ACAGCCAGACCGGCGCGCATGCCGGCATTGCCGCGGGTCGCATCGGGCTGGGCATCCTGGCTGACCTGGG
CGCCGGCCGCGTCGACAAGCTGGGCGAGGCCGGCAGCAGCGCCTACGATACGGTTTCCGGTATCGAGAAC
GTGGTGGGCACGGAACTGGCCGACCGCATCACGGGCGATGCGCAGGCCAACGTGCTGCGCGGCGCGGGTG
GCGCCGACGTGCTTGCGGGCGGCGAGGGCGACGATGTGCTGCTGGGCGGCGACGGCGACGACCAGCTGTC
GGGCGACGCCGGACGCGATCGCTTGTACGGCGAAGCCGGTGACGACTGGTTCTTCCAGGATGCCGCCAAT
GCCGGCAATCTGCTCGACGGCGGCGACGGCCGCGATACCGTGGATTTCAGCGGCCCGGGCCGGGGCCTCG
ACGCCGGCGCAAAGGGCGTATTCCTGAGCTTGGGCAAGGGGTTCGCCAGCCTGATGGACGAACCCGAAAC
CAGCAACGTGTTGCGCAATATCGAGAACGCCGTGGGCAGCGCGCGTGATGACGTGCTGATCGGCGACGCA
GGCGCCAACGTCCTCAATGGCCTGCGGGCAACGACGTGCTGTCCGGCGGCGCTGGCGACGATGTGCTGC
TGGGCGACGAGGGCTCGGACCTGCTCAGCGGCGATGCGGGCAACGACGATCTGTTCGGCGGGCAGGGCGA
TGATACTTATCTGTTCGGGGTCGGGTACGGGCACGACACGATCTACGAATCGGGCGGCGGCCATGACACC
ATCCGCATCAACGCGGGGGCGGACCAGCTGTGGTTCGCGCGCCAGGGCAACGACCTGGAGATCCGCATTC
TCGGCACCGACGATGCACTTACCGTGCACGACTGGTATCGCGACGCCGATCACCGGGTGGAAATCATCCA
TGCCGCCAACCAGGCGGTAGACCAGGCAGGCATCGAAAAGCTGGTCGAGGCAATGGCGCAGTATCCGGAC
CCCGGCGCGGCGGCGGCTGCCCCGCCGGCGGCGCGCGTGCCGGACACGCTGATGCAGTCCCTGGCTGTCA
ACTGGCGCTGA (SEQ ID NO :4)

*B. parapertussis*
GTGCTGGATGTTTGGTTCTTGCAGAAGGATGAGGTTCTGAGCGCTACACACCGGTTGCGTCGGTGCGAAT
CCGTTCAATCGACTACTTATCGACAGATCCACATGCAGCAATCGCATCAGGCTGGTTACGCAAACGCCGC
CGACCGGGAGTCTGGCATCCCCGCAGCCGTACTCGATGGCATCAAGGCCGTGGCGAAGGAAAAAAACGCC
ACATTGATGTTCCGCCTGGTCAACCCCCATTCCACCAGCCTGATTGCCGAAGGGGTGGCCACCAAAGGAT
TGGGCGTGCACGCCAAGTCGTCCGATTGGGGGTTGCAGGCGGGCTACATTCCCGTCAACCCGAATCTTTC
CAAACTGTTCGGCCGTGCGCCCGAGGTGATCGCGCGGGCCGACAACGACGTCAACAGCAGCCTGGCGCAT
GGCCATACCGCGGTCGACCTGACGCTGTCGAAAGAGCGGCTTGACTATCTGCGGCAAGCGGGCCTGGTCA
CCGGCATGGCCGATGGCGTGGTCGCGAGCAACCACGCAGGCTACGAGCAGTTCGAGTTTCGCGTGAAGGA
AACCTCGGACGGGCGCTATGCCGTGCAGTATCGCCGCAAGGGCGGCGACGATTTCGAGGCGGTCAAGGTG
ATCGGCAATGCCGCCGGTATTCCACTGACGGCGGATATCGACATGTTCGCCATCATGCCGCATCTGTCCA
ACTTCCGCGACTCGGCGCGCAGTTCGGTGACCAGCGGCGATTCGGTGACCGATTACCTGGCGCGCACGCG
GCGGGCCGCCAGCGAGGCCACGGGCGGCCTGGATCGCGAACGCATCGACTTGTTGTGGAAAATCGCTCGC
GCCGGCGCCCGTTCCGCAGTGGGCACCGAGGCGCGTCGCCAGTTCCGCTACGACGGCGACATGAATATCG
GCGTGATCACCGATTTCGAGCTGGAAGTGCGCAATGCGCTGAACAGGCGGGCGCACGCCGTCGGCGCGCA
GGACGTGGTCCAGCATGGCACTGAGCAGAACAATCCTTTCCCGGAGGCAGATGAGAAGATTTTCGTCGTA
TCGGCCACCGGTGAAAGCCAGATGCTCACGCGCGGGCAACTGAAGGAATACATTGGCCAGCAGCGCGGCG
AGGGCTATGTCTTCTACGAGAACCGTGCATACGGCGTGGCGGGGAAAAGCCTGTTCGACGATGGGCTGGG
AGCCGCGCCCGGCGTGCCGGGCGGACGTTCGAAGTCCTCGCCGGATGTACTGGAAACGGTGCCGGCGTCA
CCCGGATTGCGGCGGCCGTCGCTGGGCGCAGTGGAACGCCAGGATTCCGGCTATGACAGCCTTGATGGGG
TGGGATCGCGATCGTTCTCGTTGGGCGAGGTGTCCGACATGGCCGCCGTGGAAGCGGCGGAACTGGAAAT
GACCCGGCAAGTCTTGCACGCCGGGGCGCGGCAGGACGATGCCGAGCCGGGCGTGAGCGGTGCGTCGGCG
CACTGGGGGCAGCGGGCGCTGCAGGGCGCCCAGGCGGTGGCGGCGGCGCAGCGGCTGGTTCATGCCATTG
CCCTGATGACGCAATTCGGCCGGGCCGGTTCCACCAACACGCCGCAGGAAGCGGCCTCGTTGTCGGCGGC
CGTGTTCGGCTTGGGCGAGGCCAGCAGCGCCGTGGCCGAAACCGTGAGCGGTTTTTTCCGCGGGTCTTCG
CGCTGGGCCGGCGGTTTCGGCGTGGCTGGCGGCGCGATGGCGCTGGGAGGCGGCATCGCCGCGGCCGTTG
GCGCCGGGATGTCGTTGACCGATGACGCGCCGGCCGGACAGAAGGCCGCCGTCGGCGCCGAGATCGCGCT
GCAGTTGACAGGTGGAACGGTCGAGCTGGCTTCTTCCATCGCGTTGGCGCTGGCCGCGGCGCGCGGCGTG
ACCAGCGGCTTGCAGGTGGCGGGGGCGTCGGCCGGGCGGCTGCCGGCGCATTGGCCGCGGCGCTCAGTC
CCATGGAGATCTACGGCCTGGTGCAGCAATCGCACTATGCGGATCAGCTGGACAAGCTGGCGCAGGAATC
GAGCGCATACGGTTACGAGGGCGACGCCTTGCTGGCCCAGCTGTATCGCGACAAGACGGCCGCCGAGGGC
GCCGTCGCCGGCGTCTCCGCCGTCCTGAGCACGGTGGGGCGGCGGTGTCGATCGCCGCGGCGGCCAGCG
TGGTAGGCGCCCCGGTGGCGGTGGTCACTTCCTTGTTGACCGGGGCTCTCAACGGCATCCTGCGCGGCGT
GCAGCAGCCCATCATCGAAAAGCTGGCCAATGATTACGCTCGCAAGATCGACGAGCTGGGCGGGCCGCAA
GCGTACTTCGAGAAAAACCTGCAGGCGCGTCACGAACAACTGGCCAATTCGGACGGCCTACGGAAAATGC
TGGCTGACCTGCAGGCCGGGTGGAACGCCAGCAGCGTGATCGGGGTGCAGACGACAGAGATTTCCAAGTC
GGCGCTCGAACTGGCCGCCATTACCGGCAACGCGGACAACCTGAAATCCGCCGACGTGTTCGTGGACCGC
TTCATCCAGGGCGAGCGGGTGGCCGGCCAGCCGGTGGTACTCGACGTCGCCGCCGGCGGCATCGATATCG
CCAGCCGCAAGGGCGAGCGGCCGGCGCTGACGTTCATCACGCCGCTGGCCGCGCCAGGAGAAGAGCAGCG
CCGGCGCACGAAGACGGGCAAGAGCGAATTCACCACATTCGTCGAGATCGTGGGCAAGCAGGACCGCTGG

Fig. 1D (*B. parapertussis*/continued)
CGCATCCGGGACGGCGCGGCCGACACCACCATCGATCTGGCCAAGGTGGTGTCGCAACTGGTCGACGCCA
ATGGCGTGCTCAAGCACAGCATCAAACTGGAGGTGATCGGCGGAGATGGCGATGATGTCGTGCTTGCCAA
TGCTTCGCGCATCCATTACGACGGCGGCGCGGGAACCAACACGGTCAGCTATGCCGCCCTGGGCCGACAG
GATTCCATTACCGTGTCCGCCGACGGGGAACGTTTCAACGTGCGCAAGCAGTTGAACAACGCCAACGTGT
ATCGCGAAGGCGTGGCTACCCAGAAAACCGCCTACGGCAAGCGCACGGAGAATGTCCAATACCGCCATGT
CGAGCTGGCCCGTGTCGGGCAACTGGTGGAGGTCGACACGCTCGAGCATGTGCAGCACATCATCGGCGGG
GCCGGCAACGATTCGATCACCGGCAATGCGCACGACAACTTCCTGGCCGGCGGGCGGGCGACGACAGGC
TGGATGGCGGCGCCGGCAACGACACACTGGTCGGCGGCGAGGGCCACAACACGGTCGTCGGCGGCGCTGG
CGACGACGTATTCCTGCAGGACCTGGGGGTATGGAGCAACCAGCTCGATGGCGGCGCGGGCGTCGATACC
GTGAAGTACAACGTGCACCAGCCTTCCGAGGAACGCCTCGAACGCATGGGCGACACGGGCATCCATGCCG
ATCTTCAAAAGGGCACGGTCGAGAAGTGGCCGGCCCTGAACCTGTTCAGCGTCGACCATGTCAAGAATAT
CGAGAATCTGCACGGCTCCAGCCTGAACGACAGCATCGCCGGCGACGACCGGGACAACGAGCTCTGGGGC
GACGATGGCAACGACACGATACACGGCCGGGGCGGCGACGATATCCTGCGCGGCGGCCTGGGCCTGGACA
CGCTGTATGGCGAGGACGGCAACGACATCTTCCTGCAGGACGACGAGACCGTCAGCGATGACATCGACGG
CGGCGCGGGGCTGGACACCGTCGACTATTCCGCCATGATCCATGCAGGCAAGATCGTTGCGCCGCATGAA
TACGGCTTCGGGATCGAGGCGGACCTGTCCGAAGGGTGGGTGCGCAAGGCGGCCCGGCGCGGCATGGGCT
ACTACGACAGTGTCCGCAGTGTCGAAAACGTCATCGGCACGAGCATGAAGGATGTGCTCATCGGCGACGC
GCAAGCCAATACCCTGATGGGCCAGGGCGGCGACGATACCGTGCGCGGCGGCGACGGCGATGATCTGCTG
TTCGGCGGCGACGGCAACGACATGCTGTATGGAGACGCCGGCAACGACACCCTCTACGGAGGGCTGGGCG
ACGATACCCTTGAAGGCGGCGCGGGCAACGATTGGTTCGGCCAGACGCCGGCGCGCGAGCATGACGTGCT
GCGCGGCGGGGCTGGGGTGGATACCGTGGATTACAGCCAGGCGGGCGCGCATGCCGGCGTTGCCACGGGT
CGCATCGGGCTGGGTATTCTGGCGGACCTGGGCGCCGGCCGCGTCGACAAGCTGGGCGAGGCCGGCAGCA
GCGCCTACGATACGGTTTCCGGCATCGAAAATGTGGTGGGCACGGAACTGGCCGACCGCATCACGGGCGA
TGCGCAGGCCAACGTACTGCGCGGCGCGGGTGGTGCCGACGTGCTTGCGGGCGGCGAGGGCGACGATGTG
CTGCTGGGCGGCGAGGGCGATGACCAGCTGTCGGGCGACGCCGGACGCGACCGCTTGTACGGCGAAGCCG
GTGACGACTGGTTCTTCCAGGATGCCGCCAATGCCGGCAATCTGCTCGACGGTGGTGACGGCAACGATAC
CGTGGATTTCAGCGGCCCGGGCCGGGGCCTCGACGCCGGCGCAAAGGGCGTATTCCTGAGCCTGGGCAAG
GGGTTCGCCAGCCTGATGGACGAACCCGAAACCAGCAACGTGTTGCGCCATATCGAGAACGCCGTGGGCA
GCGTGCGTGATGACGTGCTGATCGGCGACGCAGGCGCCAACGTCCTCAATGGCCTGGCGGGCAACGACGT
GTTGTCCGGCGGCGCCGGCGACGATGTGCTGCTGGGCGACGAGGGCTCGGACCTGCTCAGCGGCGATGCG
GGCAACGACGATCTGTTCGGCGGGCAGGGCGATGATACCTATCTGTTCGGGGCCGGGTACGGACATGACA
CGATCTACGAATCGGGCGGCGGCCATGACACCATCCGTATCAACGCGGGGGCGGACCAGCTGTGGTTTGC
GCGCCAGGGCAACGACCTGGAGATCCGCATTCTTGGCACCGACGATGCACTTACCGTGCACGACTGGTAT
CGCGACGCCGATCACCGGGTGGAAGCCATCCATGCCGCCAACCAGGCCATAGACCCGGCCGGCATCGAAA
AGCTGGTCGAGGCAATGGCGCAGTACCCGGACCCCGGCGCGGCGGCGGCTGCCCCGCCGGCGGCGCGCGT
GCCGGACACGCTGATGCAGTCCCTGGCTGTCAACTGGCGCTGA (SEQ ID NO :5)

*B. bronchiseptica*
GTGCTGGATGTTTGGTTCTTGCAGAAGGATGAGGTTCTGAGCGCTACACACCGGTTGCGTCGGTGCGAAT
CCGTTCAATCGACTACTTATCGACAGATCCACATGCAGCAATCGCATCAGGCTGGTTACGCAAACGCCGC
CGACCGGGAGTCTGGCATCCCCGCAGCCGTACTCGATGGCATCAAGGCCGTGGCGAAGGAAAAAAACGCC
ACATTGATGTTCCGCCTGGTCAACCCCCATTCCACCAGCCTGATTGCCGAAGGGGTGGCCACCAAAGGAT
TGGGCGTGCACGCCAAGTCGTCCGATTGGGGGTTGCAGGCGGGCTACATTCCCGTCAACCCGAATCTTTC
CAAACTGTTCGGCCGTGCGCCCGAGGTGATCGCGCGGGCCGACAACGACGTCAACAGCAGCCTGGCGCAT
GGCCATACCGCGGTCGACCTGACGCTGTCGAAAGAGCGGCTTGACTATCTGCGGCAAGCGGGCCTGGTCA
CCGGCATGGCCGATGGCGTGGTCGCGAGCAACCACGCAGGCTACGAGCAGTTCGAGTTTCGCGTGAAGGA
AACCTCGGACGGGCGCTATGCCGTGCAGTATCGCCGCAAGGGCGGCGACGATTTCGAGGCGGTCAAGGTG
ATCGGCAATGCCGCCGGTATTCCACTGACGGCGGATATCGACATGTTCGCCATCATGCCGCATCTGTCCA
ACTTCCGCGACTCGGCGCGCAGTTCGGTGACCAGCGGCGATTCGGTGACCGATTACCTGGCGCGCACGCG
GCGGGCCGCCAGCGAGGCCACGGGCGGCCTGGATCGCGAACGCATCGACTTGTTGTGGAAAATCGCTCGC
GCCGGCGCCCGTTCCGCAGTGGGCACCGAGGCGCGTCGCCAGTTCCGCTACGACGGCGACATGAATATCG
GCGTGATCACCGATTTCGAGCTGGAAGTGCGCAATGCGCTGAACAGGCGGGCGCACGCCGTCGGCGCGCA
GGACGTGGTCCAGCATGGCACTGAGCAGAACAATCCTTTCCCGGAGGCAGATGAGAAGATTTTCGTCGTA
TCGGCCACCGGTGAAAGCCAGATGCTCACGCGCGGGCAACTGAAGGAATACATTGGCCAGCAGCGCGGCG
AGGGCTATGTCTTCTACGAGAACCGTGCGTACGGCGTGGCGGGGAAAAGCCTGTTCGACGATGGGCTGGG
AGCCGCGCCCGGCGTGCCGGGCGGACGTTCGAAGTCCTCGCCGGATGTACTGGAAACGGTGCCGGCGTCA

Fig. 1E (B. bronchiseptica/continued)
CCCGGATTGCGGCGGCCGTCGCTGGGCGCAGTGGAACGCCAGGATTCCGGCTATGACAGCCTTGATGGGG
TGGGATCGCGATCGTTCTCGTTGGGCGAGGTGTCCGACATGGCCGCCGTGGAAGCGGCGGAACTGGAAAT
GACCCGGCAAGTCTTGCACGCCGGGGCGCGGCAGGACGATGCCGAGCCGGGCGTGAGCGGTGCGTCGGCG
CACTGGGGGCAGCGGGCGCTGCAGGGCGCCCAGGCGGTGGCGGCGGCGCAGCGGCTGGTTCATGCCATTG
CCCTGATGACGCAATTCGGCCGGGCCGGTTCCACCAACACGCCGCAGGAAGCGGCCTCGTTGTCGGCGGC
CGTGTTCGGCTTGGGCGAGGCCAGCAGCGCCGTGGCCGAAACCGTGAGCGGTTTTTTCCGCGGGTCTTCG
CGCTGGGCCGGCGGTTTCGGCGTGGCTGGCGGCGCGATGGCGCTGGGAGGCGGCATCGCCGCGGCCGTTG
GCGCCGGGATGTCGTTGACCGATGACGCGCCGGCCGGACAGAAGGCCGCCGCCGGCGCCGAGATCGCGCT
GCAGTTGACAGGTGGAACGGTCGAGCTGGCTTCTTCCATCGCGTTGGCGCTGGCCGCGGCGCGCGGCGTG
ACCAGCGGCTTGCAGGTGGCGGGGGCGTCGGCCGGGGCGGCTGCCGGCGCATTGGCCGCGGCGCTCAGTC
CCATGGAGATCTACGGCCTGGTGCAGCAATCGCACTATGCGGATCAGCTGGACAAGCTGGCGCAGGAATC
GAGCGCATACGGTTACGAGGGCGACGCCTTGCTGGCCCAGCTGTATCGCGACAAGACGGCCGCCGAGGGC
GCCGTCGCCGGCGTCTCCGCCGTCCTGAGCACGGTGGGGGCTGCGGTGTCGATCGCCGCGGCGGCCAGCG
TGGTAGGCGCCCCGGTGGCGGTGGTCACTTCCTTGTTGACCGGGGCTCTCAACGGCATCCTGCGCGGCGT
GCAGCAGCCCATCATCGAAAAGCTGGCCAATGATTACGCTCGCAAGATCGACGAGCTGGGCGGGCCGCAA
GCGTACTTCGAGAAAAACCTGCAGGCGCGTCACGAACAACTGGCCAATTCGGACGGCCTACGGAAAATGC
TGGCCGACCTGCAGGCCGGGTGGAACGCCAGCAGCGTGATCGGGGTGCAGACGACAGAGATTTCCAAGTC
GGCGCTCGAACTGGCCGCCATTACCGGCAACGCGGACAACCTGAAATCCGCCGACGTGTTCGTGGACCGC
TTCATCCAGGGCGAGCGGGTGGCCGGCCAGCCGGTGGTACTCGACGTCGCCGCCGGCGGCATCGATATCG
CCAGCCGCAAGGGCGAGCGGCCGGCGCTGACGTTCATCACGCCGCTGGCCGCGCCAGGAGAAGAGCAGCG
CCGGCGCACGAAAACGGGCAAGAGCGAATTCACCACATTCGTCGAGATCGTGGGCAAGCAGGACCGCTGG
CGCATCCGGGACGGCGCGGCCGACACCACCATCGATCTGGCCAAGGTGGTGTCGCAACTGGTCGACGCCA
ATGGCGTGCTCAAGCACAGCATCAAACTGGAGGTGATCGGCGGAGATGGCGATGATGTCGTGCTTGCCAA
TGCTTCGCGCATCCATTACGACGGCGGCGCGGGAACCAACACGGTCAGCTATGCCGCCCTGGGCCGACAG
GATTCCATTACCGTGTCCGCCGACGGGGAACGTTTCAACGTGCGCAAGCAGTTGAACAACGCCAACGTGT
ATCGCGAAGGCGTGGCTACCCAGAAAACCGCCTACGGCAAGCGCACGGAGAATGTCCAATACCGCCATGT
CGAGCTGGCCCGTGTCGGGCAACTGGTGGAGGTCGACACGCTCGAGCATGTGCAGCACATCATCGGCGGG
GCCGGCAACGATTCGATCACCGGCAATGCGCACGACAACTTCCTGGCCGGCGGGGCGGGCGACGACAGGC
TGGATGGCGGCGCCGGCAACGACACACTGGTCGGCGGCGAGGGCCACAACACGGTCGTCGGCGGCGCTGG
CGACGACGTATTCCTGCAGGACCTGGGGGTATGGAGCAACCAGCTCGATGGCGGCGCGGGCGTCGATACC
GTGAAGTACAACGTGCACCAGCCTTCCGAGGAACGCCTCGAACGCATGGGCGACACGGGCATCCATGCCG
ATCTTCAAAAGGGCACGGTCGAGAAGTGGCCGGCCCTGAACCTGTTCAGCGTCGACCATGTCAAGAATAT
CGAGAATCTGCACGGCTCCAGCCTGAACGACAGCATCGCCGGCGACGACCGGGACAACGAGCTCTGGGGC
GACGATGGCAACGACACGATACACGGCCGGGGCGGCGACGATATCCTGCGCGGCGGCCTGGGCCTGGACA
CGCTGTATGGCGAGGACGGCAACGACATCTTCCTGCAGGACGACGAGACCGTCAGCGATGACATCGACGG
TGGCGCGGGACTGGACACCGTCGACTATTCCGCCATGATCCATGCAGGCAAGATCGTTGCGCCGCATGAA
TACGGCTTCGGGATCGAGGCGGACCTGTCCGAAGGGTGGGTGCGCAAGGCGGCCCGGCGCGGCATGGACT
ACTACGACAGTGTCCGCAGTGTCGAAAACGTCATCGGCACGAGCATGAAGGATGTGCTCATCGGCGACGC
GCAAGCCAATACCCTGATGGGCCAGGGCGGCGACGATACCGTGCGCGGCGGCGACGGCGATGATCTGCTG
TTCGGCGGCGACGGCAACGACATGCTGTATGGAGACGCCGGCAACGACACCCTCTACGAGGGCTGGGCG
ACGATACCCTTGAAGGCGGCGCGGGCAACGATTGGTTCGGCCAGACGCCGGCGCGCGAGCATGACGTGCT
GCGCGGCGGGGCTGGGGTGGATACCGTGGATTACAGCCAGGCGGGCGCGCATGCCGGCGTTGCCACGGGT
CGCATCGGGCTGGGTATTCTGGCGGACCTGGGCGCCGGCCGCGTCGACAAGCTGGGCGAGGCCGGCAGCA
GCGCCTACGATACGGTTTCCGGCATCGAAAATGTGGTGGGCACGGAACTGGCCGACCGCATCACGGGCGA
TGCGCAGGCCAACGTACTGCGCGGCGCGGGTGGCGCCGACGTGCTTGCGGGCGGCGAGGGCGACGATGTG
CTGCTGGGCGGCGACGGCGACGACCAGCTGTCGGGCGACGCCGGACGCGACCGCTTGTACGGCGAAGCCG
GTGACGACTGGTTCTTCCAGGATGCCGCCAATGCCGGCAATCTGCTCGACGGTGGTGACGGCAACGATAC
CGTGGATTTCAGCGGCCCGGGCCGGGGCCTCGACGCCGGCGCAAAGGGCGTATTCCTGAGCCTGGGCAAG
GGGTTCGCCAGCCTGATGGACGAACCCGAAACCAGCAACGTGTTGCGCCATATCGAGAACGCCGTGGGCA
GCGTGCGTGATGACGTGCTGATCGGCGACGCAGGCGCCAACGTCCTCAATGGCCTGCGGGCAACGACGT
GCTGTCCGGCGGCGCCGGCGACGATGTGCTGCTGGGCGACGAGGGCTCGGACCTGCTCAGCGGCGATGCG
GGCAACGACGATCTGTTCGGCGGGCAGGGCGATGATACCTATCTGTTCGGGGCCGGGTACGGACATGACA
CGATCTACGAATCGGGCGGCGGCCATGACACCATCCGTATCAACGCGGGGGCGGACCAGCTGTGGTTTGC
GCGCCAGGGCAACGACCTGGAGATCCGCATTCTTGGCACCGACGATGCACTTACCGTGCACGACTGGTAT
CGCGACGCCGATCACCGGGTGGAAGCCATCCATGCCGCCAACCAGGCCATAGACCCGGCCGGCATCGAAA
AGCTGGTCGAGGCAATGGCGCAGTACCCGGACCCCGGCGCGGCGGCGGCTGCCCCGCCGGCGGCGCGCGT
GCCGGACACGCTGATGCAGTCCCTGGCTGTCAACTGGCGCTGA (SEQ ID NO :6)

Fig. 1F

| | | |
|---|---|---|
| parapertussis | MLDVWFLQKDEVLSATHRLRRCESVQSTTYRQIHMQQSHQAGYANAADRESGIPAAVLDG | 60 |
| bronchiseptica | MLDVWFLQKDEVLSATHRLRRCESVQSTTYRQIHMQQSHQAGYANAADRESGIPAAVLDG | 60 |
| pertussis | ----------------------------------MQQSHQAGYANAADRESGIPAAVLDG | 26 |
| | ************************************ | |
| parapertussis | IKAVAKEKNATLMFRLVNPHSTSLIAEGVATKGLGVHAKSSDWGLQAGYIPVNPNLSKLF | 120 |
| bronchiseptica | IKAVAKEKNATLMFRLVNPHSTSLIAEGVATKGLGVHAKSSDWGLQAGYIPVNPNLSKLF | 120 |
| pertussis | IKAVAKEKNATLMFRLVNPHSTSLIAEGVATKGLGVHAKSSDWGLQAGYIPVNPNLSKLF | 86 |
| | ************************************************************ | |
| parapertussis | GRAPEVIARADNDVNSSLAHGHTAVDLTLSKERLDYLRQAGLVTGMADGVVASNHAGYEQ | 180 |
| bronchiseptica | GRAPEVIARADNDVNSSLAHGHTAVDLTLSKERLDYLRQAGLVTGMADGVVASNHAGYEQ | 180 |
| pertussis | GRAPEVIARADNDVNSSLAHGHTAVDLTLSKERLDYLRQAGLVTGMADGVVASNHAGYEQ | 146 |
| | ************************************************************ | |
| parapertussis | FEFRVKETSDGRYAVQYRRKGGDDFEAVKVIGNAAGIPLTADIDMFAIMPHLSNFRDSAR | 240 |
| bronchiseptica | FEFRVKETSDGRYAVQYRRKGGDDFEAVKVIGNAAGIPLTADIDMFAIMPHLSNFRDSAR | 240 |
| pertussis | FEFRVKETSDGRYAVQYRRKGGDDFEAVKVIGNAAGIPLTADIDMFAIMPHLSNFRDSAR | 206 |
| | ************************************************************ | |
| parapertussis | SSVTSGDSVTDYLARTRRAASEATGGLDRERIDLLWKIARAGARSAVGTEARRQFRYDGD | 300 |
| bronchiseptica | SSVTSGDSVTDYLARTRRAASEATGGLDRERIDLLWKIARAGARSAVGTEARRQFRYDGD | 300 |
| pertussis | SSVTSGDSVTDYLARTRRAASEATGGLDRERIDLLWKIARAGARSAVGTEARRQFRYDGD | 266 |
| | ************************************************************ | |
| parapertussis | MNIGVITDFELEVRNALNRRAHAVGAQDVVQHGTEQNNPFPEADEKIFVVSATGESQMLT | 360 |
| bronchiseptica | MNIGVITDFELEVRNALNRRAHAVGAQDVVQHGTEQNNPFPEADEKIFVVSATGESQMLT | 360 |
| pertussis | MNIGVITDFELEVRNALNRRAHAVGAQDVVQHGTEQNNPFPEADEKIFVVSATGESQMLT | 326 |
| | ************************************************************ | |
| parapertussis | RGQLKEYIGQQRGEGYVFYENRAYGVAGKSLFDDGLGAAPGVPGGRSKSSPDVLETVPAS | 420 |
| bronchiseptica | RGQLKEYIGQQRGEGYVFYENRAYGVAGKSLFDDGLGAAPGVPGGRSKSSPDVLETVPAS | 420 |
| pertussis | RGQLKEYIGQQRGEGYVFYENRAYGVAGKSLFDDGLGAAPGVPSGRSKFSPDVLETVPAS | 386 |
| | ****************************************.*.************ | |
| parapertussis | PGLRRPSLGAVERQDSGYDSLDGVGSRSFSLGEVSDMAAVEAAELEMTRQVLHAGARQDD | 480 |
| bronchiseptica | PGLRRPSLGAVERQDSGYDSLDGVGSRSFSLGEVSDMAAVEAAELEMTRQVLHAGARQDD | 480 |
| pertussis | PGLRRPSLGAVERQDSGYDSLDGVGSRSFSLGEVSDMAAVEAAELEMTRQVLHAGARQDD | 446 |
| | ************************************************************ | |
| parapertussis | AEPGVSGASAHWGQRALQGAQAVAAAQRLVHAIALMTQFGRAGSTNTPQEAASLSAAVFG | 540 |
| bronchiseptica | AEPGVSGASAHWGQRALQGAQAVAAAQRLVHAIALMTQFGRAGSTNTPQEAASLSAAVFG | 540 |
| pertussis | AEPGVSGASAHWGQRALQGAQAVAAAQRLVHAIALMTQFGRAGSTNTPQEAASLSAAVFG | 506 |
| | ************************************************************ | |
| parapertussis | LGEASSAVAETVSGFFRGSSRWAGGFGVAGGAMALGGGIAAAVGAGMSLTDDAPAGQKAA | 600 |
| bronchiseptica | LGEASSAVAETVSGFFRGSSRWAGGFGVAGGAMALGGGIAAAVGAGMSLTDDAPAGQKAA | 600 |
| pertussis | LGEASSAVAETVSGFFRGSSRWAGGFGVAGGAMALGGGIAAAVGAGMSLTDDAPAGQKAA | 566 |
| | ************************************************************ | |
| parapertussis | VGAEIALQLTGGTVELASSIALALAAARGVTSGLQVAGASAGAAAGALAAALSPMEIYGL | 660 |
| bronchiseptica | AGAEIALQLTGGTVELASSIALALAAARGVTSGLQVAGASAGAAAGALAAALSPMEIYGL | 660 |
| pertussis | AGAEIALQLTGGTVELASSIALALAAARGVTSGLQVAGASAGAAAGALAAALSPMEIYGL | 626 |
| | ************************************************************ | |
| parapertussis | VQQSHYADQLDKLAQESSAYGYEGDALLAQLYRDKTAAEGAVAGVSAVLSTVGAAVSIAA | 720 |
| bronchiseptica | VQQSHYADQLDKLAQESSAYGYEGDALLAQLYRDKTAAEGAVAGVSAVLSTVGAAVSIAA | 720 |
| pertussis | VQQSHYADQLDKLAQESSAYGYEGDALLAQLYRDKTAAEGAVAGVSAVLSTVGAAVSIAA | 686 |
| | ************************************************************ | |

Fig. 2A

```
parapertussis    AASVVGAPVAVVTSLLTGALNGILRGVQQPIIEKLANDYARKIDELGGPQAYFEKNLQAR  780
bronchiseptica   AASVVGAPVAVVTSLLTGALNGILRGVQQPIIEKLANDYARKIDELGGPQAYFEKNLQAR  780
pertussis        AASVVGAPVAVVTSLLTGALNGILRGVQQPIIEKLANDYARKIDELGGPQAYFEKNLQAR  746
                 ************************************************************ parapertussis    HEQLANSDGLRKMLADLQAGWNASSVIGVQTTEISKSALELAAITGNADNLKSADVFVDR  840
bronchiseptica   HEQLANSDGLRKMLADLQAGWNASSVIGVQTTEISKSALELAAITGNADNLKSADVFVDR  840
pertussis        HEQLANSDGLRKMLADLQAGWNASSVIGVQTTEISKSALELAAITGNADNLKSVDVFVDR  806
                 ***************************************************.**** parapertussis    FIQGERVAGQPVVLDVAAGGIDIASRKGERPALTFITPLAAPGEEQRRRTKTGKSEFTTF  900
bronchiseptica   FIQGERVAGQPVVLDVAAGGIDIASRKGERPALTFITPLAAPGEEQRRRTKTGKSEFTTF  900
pertussis        FVQGERVAGQPVVLDVAAGGIDIASRKGERPALTFITPLAAPGEEQRRRTKTGKSEFTTF  866
                 *:********************************************************** parapertussis    VEIVGKQDRWRIRDGAADTTIDLAKVVSQLVDANGVLKHSIKLEVIGGDGDDVVLANASR  960
bronchiseptica   VEIVGKQDRWRIRDGAADTTIDLAKVVSQLVDANGVLKHSIKLEVIGGDGDDVVLANASR  960
pertussis        VEIVGKQDRWRIRDGAADTTIDLAKVVSQLVDANGVLKHSIKLDVIGGDGDDVVLANASR  926
                 ****************************************:*************** parapertussis    IHYDGGAGTNTVSYAALGRQDSITVSADGERFNVRKQLNNANVYREGVATQKTAYGKRTE  1020
bronchiseptica   IHYDGGAGTNTVSYAALGRQDSITVSADGERFNVRKQLNNANVYREGVATQKTAYGKRTE  1020
pertussis        IHYDGGAGTNTVSYAALGRQDSITVSADGERFNVRKQLNNANVYREGVATQTTAYGKRTE  986
                 *************************************************.****** parapertussis    NVQYRHVELARVGQLVEVDTLEHVQHIIGGAGNDSITGNAHDNFLAGGAGDDRLDGGAGN  1080
bronchiseptica   NVQYRHVELARVGQLVEVDTLEHVQHIIGGAGNDSITGNAHDNFLAGGAGDDRLDGGAGN  1080
pertussis        NVQYRHVELARVGQLVEVDTLEHVQHIIGGAGNDSITGNAHDNFLAGGSGDDRLDGGAGN  1046
                 **********************************************:********* parapertussis    DTLVGGEGHNTVVGGAGDDVFLQDLGVWSNQLDGGAGVDTVKYNVHQPSEERLERMGDTG  1140
bronchiseptica   DTLVGGEGHNTVVGGAGDDVFLQDLGVWSNQLDGGAGVDTVKYNVHQPSEERLERMGDTG  1140
pertussis        DTLVGGEGQNTVIGGAGDDVFLQDLGVWSNQLDGGAGVDTVKYNVHQPSEERLERMGDTG  1106
                 ******:*:************************************************ parapertussis    IHADLQKGTVEKWPALNLFSVDHVKNIENLHGSSLNDSIAGDDRDNELWGDDGNDTIHGR  1200
bronchiseptica   IHADLQKGTVEKWPALNLFSVDHVKNIENLHGSSLNDSIAGDDRDNELWGDDGNDTIHGR  1200
pertussis        IHADLQKGTVEKWPALNLFSVDHVKNIENLHGSRLNDRIAGDDQDNELWGHDGNDTIRGR  1166
                 ********************************* ***** ******.******:**

parapertussis    GGDDILRGGLGLDTLYGEDGNDIFLQDDETVSDDIDGGAGLDTVDYSAMIHAGKIVAPHE  1260
bronchiseptica   GGDDILRGGLGLDTLYGEDGNDIFLQDDETVSDDIDGGAGLDTVDYSAMIHAGKIVAPHE  1260
pertussis        GGDDILRGGLGLDTLYGEDGNDIFLQDDETVSDDIDGGAGLDTVDYSAMIHPGRIVAPHE  1226
                 ***************************************************.*:****** parapertussis    YGFGIEADLSEGWVRKAARRGMGYYDSVRSVENVIGTSMKDVLIGDAQANTLMGQGGDDT  1320
bronchiseptica   YGFGIEADLSEGWVRKAARRGMDYYDSVRSVENVIGTSMKDVLIGDAQANTLMGQGGDDT  1320
pertussis        YGFGIEADLSREWVRKASALGVDYYDNVRNVENVIGTSMKDVLIGDAQANTLMGQGGDDT  1286
                 ********. ***:  *:.*..****************************** parapertussis    VRGGDGDDLLFGGDGNDMLYGDAGNDTLYGGLGDDTLEGGAGNDWFGQTPAREHDVLRGG  1380
bronchiseptica   VRGGDGDDLLFGGDGNDMLYGDAGNDTLYGGLGDDTLEGGAGNDWFGQTPAREHDVLRGG  1380
pertussis        VRGGDGDDLLFGGDGNDMLYGDAGNDTLYGGLGDDTLEGGAGNDWFGQTQAREHDVLRGG  1346
                 ********************************************** ******** parapertussis    AGVDTVDYSQAGAHAGVATGRIGLGILADLGAGRVDKLGEAGSSAYDTVSGIENVVGTEL  1440
bronchiseptica   AGVDTVDYSQAGAHAGVATGRIGLGILADLGAGRVDKLGEAGSSAYDTVSGIENVVGTEL  1440
pertussis        DGVDTVDYSQTGAHAGIAAGRIGLGILADLGAGRVDKLGEAGSSAYDTVSGIENVVGTEL  1406
                 ********:.*****:*:******************************************
```

Fig. 2B

```
parapertussis    ADRITGDAQANVLRGAGGADVLAGGEGDDVLLGGEGDDQLSGDAGRDRLYGEAGDDWFFQ  1500
bronchiseptica   ADRITGDAQANVLRGAGGADVLAGGEGDDVLLGGDGDDQLSGDAGRDRLYGEAGDDWFFQ  1500
pertussis        ADRITGDAQANVLRGAGGADVLAGGEGDDVLLGGDGDDQLSGDAGRDRLYGEAGDDWFFQ  1466
                 **********************************:********************* parapertussis    DAANAGNLLDGGDGNDTVDFSGPGRGLDAGAKGVFLSLGKGFASLMDEPETSNVLRHIEN  1560
bronchiseptica   DAANAGNLLDGGDGNDTVDFSGPGRGLDAGAKGVFLSLGKGFASLMDEPETSNVLRHIEN  1560
pertussis        DAANAGNLLDGGDGRDTVDFSGPGRGLDAGAKGVFLSLGKGFASLMDEPETSNVLRNIEN  1526
                 ************.*************************************:* parapertussis    AVGSVRDDVLIGDAGANVLNGLAGNDVLSGGAGDDVLLGDEGSDLLSGDAGNDDLFGGQG  1620
bronchiseptica   AVGSVRDDVLIGDAGANVLNGLAGNDVLSGGAGDDVLLGDEGSDLLSGDAGNDDLFGGQG  1620
pertussis        AVGSARDDVLIGDAGANVLNGLAGNDVLSGGAGDDVLLGDEGSDLLSGDAGNDDLFGGQG  1586
                 **.***************************************************** parapertussis    DDTYLFGAGYGHDTIYESGGGHDTIRINAGADQLWFARQGNDLEIRILGTDDALTVHDWY  1680
bronchiseptica   DDTYLFGAGYGHDTIYESGGGHDTIRINAGADQLWFARQGNDLEIRILGTDDALTVHDWY  1680
pertussis        DDTYLFGVGYGHDTIYESGGGHDTIRINAGADQLWFARQGNDLEIRILGTDDALTVHDWY  1646
                 *****.************************************************** parapertussis    RDADHRVEAIHAANQAIDPAGIEKLVEAMAQYPDPGAAAAAPPAARVPDTLMQSLAVNWR  1740
bronchiseptica   RDADHRVEAIHAANQAIDPAGIEKLVEAMAQYPDPGAAAAAPPAARVPDTLMQSLAVNWR  1740
pertussis        RDADHRVEIIHAANQAVDQAGIEKLVEAMAQYPDPGAAAAAPPAARVPDTLMQSLAVNWR  1706
                 ******** ******:* *******************************************
```

Fig. 2C

MQQSHQAGYANAADRESGIPAAVLDGIKAVAKEKNATLMFRLVNPHSTSL
IAEGVATKGLGVHAKSSDWGLQAGYIPVNPNLSKLFGRAPEVIARADNDV
NSSLAHGHTAVDLTLSKERLDYLRQAGLVTGMADGVVASNHAGYEQFEFR
VKETSDGRYAVQYRRKGGDDFEAVKVIGNAAGIPLTADLQIDMFAIMPHL
SNFRDSARSSVTSGDSVTDYLARTRRASTFPDLESEFQAALSRKVAELVH
FLLLKYRAREPVTKAEMLGSVVGNWQYFFPVIFSKASSSLQLVFGIELME
VDPIGHLYIFGTRARLKLLWKIARAGARSAVGTEARRQFRYDGDMNIGVI
TDFELEVRNALNRRAHAVGAQDVVQHGTEQNNPFPEADEKIFVVSAT**GLG
DNQIMPKAGLLIIVLAIIAREGDCAPEEKIPKKLLTQHFVQENYLEYRQV
PGSDPACYEFLWGPRALVETSYVKVLHHMVKISG**TSESQMLTRGQLKEYI
GQQRGEGYVFYENRAYGVAGKSLFDDGLGAAPGVPSGRSKFSPDVLETVP
ASPGLRRPSLGAVERQDSGYDSLDGVGSRSFSLGEVSDMAAVEAAELEMT
RQVLHAGARQDDAEPGVSGASAHWGQRALQGAQAVAAAQRLVHAIALMTQ
FGRAGSTNTPQEAASLSAAVFGLGEASSAVAETVSGFFRGSSRWAGGFGV
AGGAMALGGGIAAAVGAGMSLTDDAPAGQKAAAGAEIALQLTGGTVELAS
SIALALAAARGVTSGLQVAGASAGAAAGALAAALSPMEIYGLVQQSHYAD
QLDKLAQESSAYGYEGDALLAQLYRDKTAAEGAVAGVSAVLSTVGAAVSI
AAAASVVGAPVAVVTSLLTGALNGILRGVQQPIIEKLANDYARKIDELGG
PQAYFEKNLQARHEQLANSDGLRKMLADLQAGWNASSVIGVQTTEISKSA
LELAAITGNADNLKSVDVFVDRFVQGERVAGQPVVLDVAAGGIDIASRKG
ERPALTFITPLAAPGEEQRRRTKTGKSEFTTFVEIVGKQDRWRIRDGAAD
TTIDLAKVVSQLVDANGVLKHSIKLDVIGGDGDDVVLANASRIHYDGGAG
TNTVSYAALGRQDSITVSADGERFNVRQLNNANVYREGVATQTTAYGKR
TENVQYRHVELARVGQLVEVDTLEHVQHIIGGAGNDSITGNAHDNFLAGG
SGDDRLDGGAGNDTLVGGEGQNTVIGGAGDDVFLQDLGVWSNQLDGGAGV
DTVKYNVHQPSEERLERMGDTGIHADLQKGTVEKWPALNLFSVDHVKNIE
NLHGSRLNDRIAGDDQDNELWGHDGNDTIRGRGGDDILRGGLGLDTLYGE
DGNDIFLQDDETVSDDIDGGAGLDTVDYSAMIHPGRIVAPHEYGFGIEAD
LSREWVRKASALGVDYYDNVRNVENVIGTSMKDVLIGDAQANTLMGQGGD
DTVRGGDGDDLLFGGDGNDMLYGDAGNDTLYGGLGDDTLEGGAGNDWFGQ
TQAREHDVLRGGDGVDTVDYSQTGAHAGIAAGRIGLGILADLGAGRVDKL
GEAGSSAYDTVSGIENVVGTELADRITGDAQANVLRGAGGADVLAGGEGD
DVLLGGDGDDQLSGDAGRDRLYGEAGDDWFFQDAANAGNLLDGGDGRDTV
DFSGPGRGLDAGAKGVFLSLGKGFASLMDEPETSNVLRNIENAVGSARDD
VLIGDAGANVLNGLAGNDVLSGGAGDDVLLGDEGSDLLSGDAGNDDLFGG
QGDDTYLFGVGYHDTIYESGGGHDTIRINAGADQLWFARQGNDLEIRIL
GTDDALTVHDWYRDADHRVEIIHAANQAVDQAGIEKLVEAMAQYPDPGAA
AAAPPAARVPDTLMQSLAVNWR (SEQ ID NO:7)

Fig. 4C

CYAA-CARRIED POLYPEPTIDE(S) AND USE TO INDUCE BOTH THERAPEUTIC AND PROPHYLACTIC IMMUNE RESPONSES

FIELD OF THE INVENTION

The invention is directed to means, based on CyaA-carried polypeptide(s), for use in the immunotherapeutic treatment of first determined pathological condition(s) diagnosed in a mammalian host by eliciting a T cell immune response against a first group of epitopes contained in said polypeptide(s) and in the prophylaxis against second determined pathological condition(s) in the same mammalian host by eliciting a T cell memory immune response against a second group of epitopes contained in said polypeptide(s), said immune responses being obtained after administration of said vector-carried polypeptide(s) into said host, wherein said prophylaxis against second determined pathological condition(s) is not observed when said second group of epitopes is not contained in said administered vector-carried polypeptide(s). In a particular embodiment, the invention is directed to means, based on CyaA-carried polypeptide(s), for use (i) in the immunotherapeutic treatment of first determined pathological condition(s) diagnosed in a mammalian host, by eliciting a T cell immune response against a first group of epitopes contained in said polypeptide(s), (ii) in the prophylaxis against second determined pathological condition(s) in the same mammalian host, by eliciting a T cell memory immune response against a second group of epitopes contained in said polypeptide(s) and (iii) in the prevention against the re-occurrence of said first determined pathological condition(s), by eliciting a T cell memory immune response against said first group of epitopes contained in said polypeptide(s), said immune responses being obtained after administration of said vector-carried polypeptide(s) into said host, wherein said prophylaxis against second determined pathological condition(s) is not observed when said second group of epitopes is not contained in said administered vector-carried polypeptide(s).

BACKGROUND OF THE INVENTION

One of the key toxins produced by *Bordetella pertussis*, the pathogen responsible for the whooping cough, is its Adenylate Cyclase (CyaA). It was shown using a murine model that CyaA is required by the bacteria during the early phase of lung colonization (Goodwin and Weiss 1990). CyaA exhibits a unique mechanism of eukaryotic cell invasion by delivering in a dedicated fashion its catalytic domain into cell cytosol (Simsova, Sebo et al. 2004). Detoxified and recombinant CyaA used as a vaccine vector displays the exquisite ability to target CD11b/CD18-expressing antigen presenting cells (APC), as for example dendritic cells or Langerhans cells (Guermonprez et al. 2001). These residents APC are key innate cells in the initiation of antigen-specific T-cell responses following intradermal immunization approaches (Merad, Ginhoux et al. 2008). After specific binding to CD11b$^+$ APC, CyaA carrying either a viral or tumour antigen can deliver its antigenic cargo in a dedicated manner (Preville, Ladant et al. 2005). Based on this unique technology, the Applicant has developed a clinical stage bivalent vaccine to cure HPV infected patients: ProCervix. ProCervix is a bivalent therapeutic vaccine prepared with a mixture of two different CyaA vaccines: one embedding the HPV16 E7 protein and the other one carrying the HPV18 E7 protein.

Indeed Human papillomavirus (HPV) infections are generally long lasting and a compromised host immune response can lead to the development of cervical cancer, especially with high-risk HPV such as HPV18 and HPV16. E7 oncoproteins of HPV are expressed all along the replicative cycle of the virus, thus making them chosen targets for T-cell mediated immunotherapy (Iwasaki 2010). B-cell mediated immunity to the viral capsid proteins has been shown to be sufficient for a prophylactic protection against HPV infection (Stanley 2010). However, innate and T-cell mediated immunities are critical to cure patients that are already infected by the virus (Frazer 2009). Besides, available HPV prophylactic vaccines are not efficient to treat already HPV-infected patients and to cure the disease, thus highlighting the importance to develop therapeutic vaccines that would elicit antigen-specific T cell responses against HPV antigens (Trimble and Frazer 2009).

Prophylactic vaccines are based on the development of a B-cell mediated immunity. By contrast, therapeutic vaccines aim to develop strong and robust pro-inflammatory CD4$^+$ and CD8$^+$ T cell responses for an efficient treatment of chronic infection (virus, bacteria, etc.) or of cancer (Bachmann and Jennings 2010). Many studies have described both in mouse model and in human patients that induction of an antigen-specific T cell immunity can be correlated with a protection against diseased cells, either infected cells or tumour cells (Pulendran, Li et al. 2010; Sallusto, Lanzavecchia et al. 2010). By measuring qualitative and quantitative aspects of the CD8$^+$ T cell response induced post-therapeutic vaccination in tumour bearing mice, it is possible to predict the therapeutic outcome, i.e., the progression or the regression of the tumour in individual animals (Rosato, Zoso et al. 2006). After a successful therapeutic vaccination that leads to a complete elimination of diseased cells, a key aspect of this immunotherapy would be its potential to generate long-term memory T lymphocytes in order to protect the patient against secondary pathogen infection. Memory T lymphocytes can be classified in two main cellular subsets: $T_{EM}$ (Effector Memory) and $T_{CM}$ (Central Memory). $T_{EM}$ are the first memory T cells to be generated following the clonal contraction phase of the immune response which fit with the elimination of the pathogen. $T_{EM}$ are CD62L$^-$ CCR7$^-$ and preferentially reside in peripheral tissues, such as the skin, gut and lungs, where they provide a first line of defence for the host (Woodland and Kohlmeier 2009). Over time, $T_{EM}$ progressively differentiate towards a $T_{CM}$ phenotype: CD62L$^+$ CCR7$^-$. These T lymphocytes are preferentially localized in secondary lymphoid organs (Kaech, Hemby et al. 2002; Ahmed, Bevan et al. 2009). Nevertheless both $T_{EM}$ and $T_{CM}$ are found in the circulation. A critical aspect of CD8 memory response efficacy is the speed at which CD8$^+$ memory T lymphocyte acquire lytic potential and thus eliminate infected cells upon a novel infection by the same pathogen in order to prevent the spread of the infection and in turn the associated disease development. It has been shown that mice, that have been able to clear Lymphocytic choriomeningitis virus (LCMV) acute infection via the development of antigen-specific CD8$^+$ T-cell responses, also developed memory CD8$^+$ T-cells able to rapidly eliminate infected cells (Barber et al., 2003).

Based on this knowledge, the inventors have extended the approach of therapeutic vaccination involving T cell mediated immune response to devise a new concept of therapeutic and prophylactic treatment of pathological condition(s) by way of combining the administration of active ingredients in a designed multivalent immunogenic composition involving vectorized epitopes.

In particular, the inventors designed multivalent therapeutic vaccines suitable to induce, in a single patient, an immunotherapeutic treatment against a diagnosed pathology while mounting a robust prophylactic response against antigens or epitopes that are not related to said treated pathology, and optionally mounting a protective and preventive response against the re-occurrence of said treated pathology.

Indeed, the use of CyaA-based multivalent therapeutic approaches highlights the potential of CyaA-carried polypeptide(s) to treat and possibly eradicate a determined infection or a cancer while providing in the same patient a strong immune response, preferably protective T-cell memory response, against targeted epitopes contained in said polypeptide(s) against which a prophylactic protection is sought, and optionally a protective and preventive response against the re-occurrence of said determined infection or cancer.

BRIEF DESCRIPTION OF THE DRAWINGS

FIG. 1A. Protein sequence of the adenylate cyclase (CyaA) of *B. pertussis* and *B. parapertussis* SEQ ID NOs: 1 and 2, nucleotide sequence of CyaA of *B. pertussis* and *B. parapertussis* (SEQ ID NOs: 4 and 5).

FIG. 1B Protein sequence of the adenylate cyclase (CyaA) of *B. Bronchiseptica* (SEQ ID NO: 3).

FIG. 1C Nucleotide sequence of CyaA of *B. pertussis* (SEQ ID NOs: 4).

FIG. 1D. Nucleotide sequence of CyaA of *B. pertussis* and *B. parapertussis* (SEQ ID NOs: 4 and 5).

FIG. 1E. Nucleotide sequence of CyaA of *B. parapertussis* (SEQ ID No.5) and *B. Bronchiseptica* (SEQ ID NO: 6).

FIG. 1F. Nucleotide sequence of CyaA of B. *Bronchiseptica* (SEQ ID NO: 6).

FIG. 2A, FIG. 2C and FIG. 2C. Protein alignment of the CyaA proteins of *B. pertussis, B. parapertussis* and *B. Bronchiseptica*.

FIG. 4C. Protein sequence of the CyaA-MAGEA3 vector (SEQ ID NO:7). The MAGEA3 sequence is underlined. The restrictions sites are in bold: NheI (AS), KpnI (GT), AgeI (TG) and SpeI (TS).

DETAILED DESCRIPTION

Figure 3A:
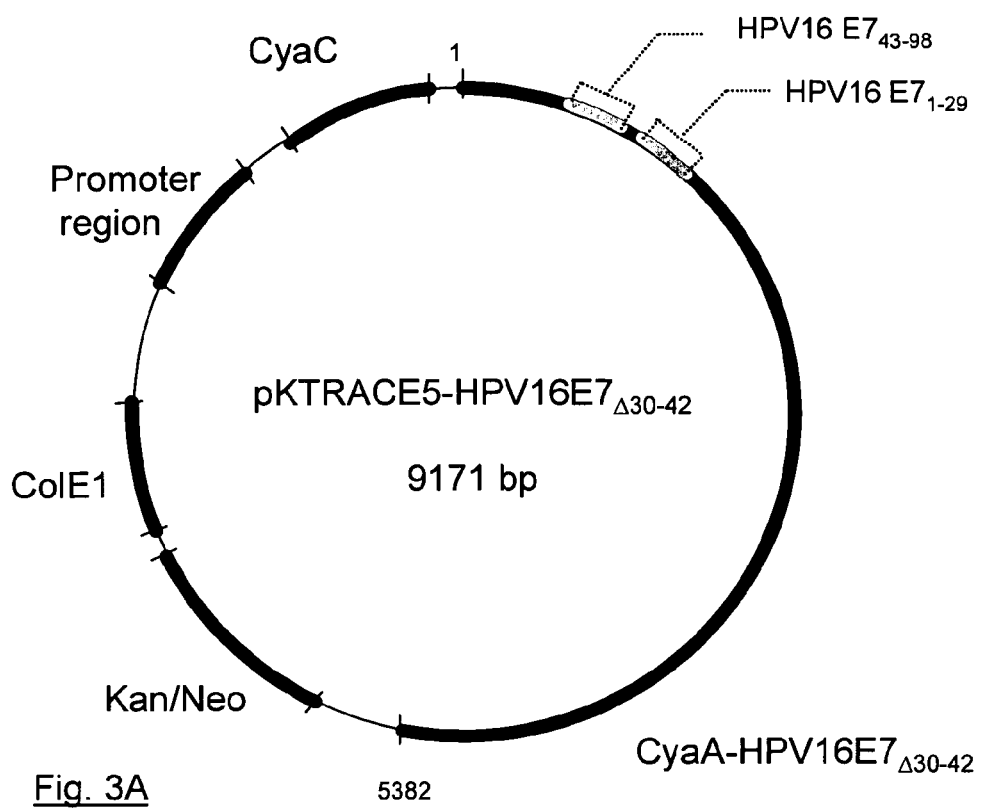
FIG. 3A. Schematic map of pkTRACE5 in which relevant restriction sites and inserted sequences are indicated for CyaA-HPV16E7$_{D30-42}$.

The invention is directed to means for use (i) in the immunotherapeutic treatment of first determined pathological condition(s) diagnosed in a mammalian host and (ii) in the prophylaxis against second determined pathological condition(s) in the same mammalian host, and (iii) optionally in the prevention of the re-occurrence of said first determined pathological condition(s). The immune response is obtained by (i) eliciting a T cell immune response against a first group of epitopes contained in polypeptide(s) designed as active ingredient(s) to treat said diagnosed pathological condition(s) and (ii) by eliciting a T cell memory immune response against a second group of epitopes contained in polypeptide(s) designed as active ingredient(s) to prevent the onset or the development of said second determined condition(s), and (iii) optionally by eliciting a T cell memory immune response against said first group of epitopes to prevent the re-occurrence of said first determined pathological condition(s), said immune responses being obtained after administration of said vector-carried polypeptide(s) into said host, wherein said prophylaxis against second determined pathological condition(s) is not observed when said second group of epitopes is not contained in said administered vector-carried polypeptide(s). These means include:

(1) as active ingredients, vector-carried polypeptide(s), wherein said vector carrying the polypeptide(s) consists in a CyaA protein or a fragment thereof suitable to present said polypeptide(s) to the immune system in a mammalian host;

(2) a composition comprising or containing such active ingredients including a composition comprising the vector-carried polypeptide(s) as defined in (1) in combination with a pharmaceutically acceptable vehicle or formulation; and (3) a composition comprising a first vector-carried polypeptide(s) containing a first group of epitopes and a second separate vector-carried polypeptide(s) containing the second group of epitopes.

Thus, in a first embodiment the invention concerns vector-carried polypeptide(s), wherein said vector carrying the polypeptide(s) consists in a CyaA protein or a fragment thereof suitable to present said polypeptide(s) to the immune system in a mammalian host, for use (i) in the immunotherapeutic treatment of first determined pathological condition(s) diagnosed in said mammalian host by eliciting a T cell immune response against a first group of epitopes contained in said polypeptide(s) and (ii) in the prophylaxis against second determined pathological condition(s) in the same mammalian host by eliciting a T cell memory immune response against a second group of epitopes contained in said polypeptide(s), and (iii) optionally in the prevention against the re-occurrence of said first determined pathological condition(s) by eliciting a T cell memory immune response against said first group of epitopes contained in said polypeptide(s), said immune responses being obtained after administration of said vector-carried polypeptide(s) into said host, wherein said prophylaxis against second determined pathological condition(s) is not observed when said second group of epitopes is not contained in said administered vector-carried polypeptide(s).

The invention also concerns a composition comprising, in combination with a pharmaceutically acceptable vehicle, a vector-carried polypeptide(s), wherein said vector carrying the polypeptide(s) consists in a CyaA protein or a fragment thereof suitable to present said polypeptide(s) to the immune system in a mammalian host, for use (i) in the immunotherapeutic treatment of first determined pathological condition(s) diagnosed in said mammalian host by eliciting a T cell immune response against a first group of epitopes contained in said polypeptide(s) and (ii) in the prophylaxis against second determined pathological condition(s) in the same mammalian host by eliciting a T cell memory immune response against a second group of epitopes contained in said polypeptide(s), and (iii) optionally in the prevention against the re-occurrence of said first determined pathological condition(s) by eliciting a T cell memory immune response against said first group of epitopes contained in said polypeptide(s) said immune responses being obtained after administration of said composition into said host, wherein said prophylaxis against second determined pathological condition(s) is not observed when said second group of epitopes is not contained in the vector-carried polypeptide(s) of said administered composition.

The invention also relates to a composition comprising, optionally in combination with a pharmaceutically acceptable vehicle:
- (a) a first vector-carried polypeptide(s), wherein said first vector carrying the polypeptide(s) consists in a CyaA protein or a fragment thereof suitable to present said polypeptide(s) to the immune system in a mammalian host, and wherein a first group of epitopes is contained in said polypeptide(s) of said first vector;
- (b) a second separate vector-carried polypeptide(s), wherein said second vector carrying the polypeptide(s) consists in a CyaA protein or a fragment thereof suitable to present said polypeptide(s) to the immune system in a mammalian host, and wherein a second group of epitopes is contained in said polypeptide(s) in said second vector; and
- (c) optionally, one or more additional vector-carried polypeptide(s) distinct from those in (a) and (b), for use in (i) combined immunotherapeutic treatment against pathology associated with said first group of epitopes and (ii) immunoprophylaxis treatment associated with said second group of epitopes and (iii) optionally prevention against the re-occurrence of said first determined pathological condition(s), wherein said prophylaxis against second determined pathological condition(s) is not observed when said second group of epitopes is not contained in the vector-carried polypeptide(s) of said administered composition.

In a specific embodiment, said composition with (a), (b) and (c) is for use (i) in the immunotherapeutic treatment of first determined pathological condition(s) diagnosed in said mammalian host by eliciting a T cell immune response against the first group of epitopes and (ii) in the prophylaxis against second determined pathological condition(s) in the same mammalian host by eliciting a T cell memory immune response against the second group of epitopes contained in said polypeptide(s), and (iii) optionally in the prevention against the re-occurrence of said first determined pathological condition(s) by eliciting a T cell memory immune response against said first group of epitopes contained in said polypeptide(s), said immune responses being obtained after administration of said composition into said host.

The term "CyaA" means an Adenylate Cyclase (or adenylcyclase) of a *Bordetella* species, in particular a CyaA from *Bordetella pertussis*, *Bordetella parapertussis* or *Bordetella bronchiseptica*. The adenylate cyclase protein of *Bordetella pertussis* is a toxin of 1706 residues (SEQ ID NO:1), comprising a N-terminal catalytic domain of 400 amino acid residues and a C-terminal part of 1306 residues. The C-terminal part is responsible for the binding of the toxin to target cell membrane and subsequent delivery of the catalytic moiety into the target cell cytosol. The sequence of *Bordetella pertussis* CyaA is provided in FIG. 1. The CyaA protein of *B. parapertussis* and of *B. bronchiseptica* has 1740 amino acids, and their respective sequence (SEQ ID NO:2 and SEQ ID NO:3) is disclosed in FIG. 1.

The expression "CyaA fragment" means a part of the CyaA protein, optionally encompassing all or part of the C-terminal part of the full-length CyaA protein, provided said fragment is able to present said polypeptide(s) to the immune system in a mammalian host, i.e., is able to lead to the induction of specific immune response(s) against epitopes contained in the vector-carried polypeptide(s) or to favour said response. In particular, said CyaA fragment is able to specifically bind to CD11b-expressing cells and optionally to deliver said polypeptide(s) into the cell cytosol. Said fragment encompasses a CyaA protein which has been truncated (deletion from the N-terminal and/or C-terminal extremities) or a full-length protein with internal deletion of amino acid residue(s). Thus, a particular fragment of CyaA protein according to the invention consists of amino acid residues 372 to 1706 of *B. pertussis* CyaA protein (truncation of the first 371 residues). Another particular fragment is the *B. pertussis* CyaA protein wherein amino acid residues 225 to 234 have been deleted, thus providing a CyaA fragment consisting of residues 1 to 224 and 235 to 1706 (internal deletion). The term "specifically" means within the context of the present invention that the adenylate cyclase or its fragment, when used as a vector molecule, is preferentially directed to CD11b-expressing cells, thereby offering means to target the polypeptide(s) at the surface of said cells or within said cells in a selective way with respect to other cells (not expressing CD11b).

The term "CyaA" also encompasses a CyaA protein or its fragments which is modified, preferably by one or more amino acid substitution(s), internal insertion of amino acid(s) or internal deletion of amino acid(s), in order to give rise to a detoxified or a non-toxic product or a product devoid of enzymatic (invasive and cytotoxic) activity. Thus, such a CyaA protein (or its fragments) has no catalytic activity, but the capacity to present said polypeptide(s) to the immune system in a mammalian host, and optionally the specific binding to CD11b/CD18 receptor and/or the process of translocation of the catalytic domain of the original CyaA protein, is(are) not affected. An example of a well-known non-toxic CyaA protein is a *Bordetella pertussis* CyaA in which the dipeptide Leu-Gln has been inserted in-frame between residues Asp188 and 11e189 (essential part of the catalytic site). The absence of toxicity or enzymatic activity of this CyaA protein (or its fragments) may be assayed as disclosed in Ladant et al. (1992). The capacity of the CyaA protein (or its fragments) to target CD11b/CD18 cells can be assayed especially according to the methods disclosed in EP03291486 or in WO02/22169. Furthermore, the capacity of the CyaA protein (or its fragments) to translocate the antigenic polypeptide into the cytosol of target cell can be assayed by applying the method described in WO02/22169.

In a further particular embodiment, the term "CyaA" also encompasses, the CyaA protein (or its fragments) which has been modified by post-translational modifications, for example by post translational palmitoyation of at least one of its residues, in particular the two internal lysine residues (lysines 860 and 983). This (these) post translational modification(s) may be obtained by co-expression of the cyaA and cyaC genes. Thus, the CyaA protein or a fragment thereof, within the vector-carried polypeptide(s), may be a CyaA protein or a fragment thereof which is the result of the co-expression in a cell, especially in a recombinant cell, of both cyaA and cyaC genes.

The term "vector" or "vector molecule" used in the present application encompasses the full-length CyaA protein, or fragments thereof, modified or not, as detailed herein.

By "CD11b-expressing cells", it is meant cells that express the CD11b/CD18 receptor on their surface (CD11b+). In particular, these cells are granulocytes/neutrophils, macrophages, NK cells, subsets of T CD8$^+$, subsets of B cells, Langerhans cells, dendritic cells and myeloid dendritic cells.

The expression "vector-carried polypeptide(s)" means that the CyaA protein (or its fragments) carries at least one polypeptide which is heterologous with respect to CyaA, in particular which is not a CyaA fragment as defined herein, and especially does not immunologically cross-react with CyaA. The expression "at least one" means one polypeptide or more, in particular 1, 2, 3, 4, 5, 6, 7, 8, 9 or 10 polypeptide(s), preferably 1, 2 or 3 polypeptide(s).

The term "carries" encompasses various structures associating the CyaA protein or a fragment thereof in accordance with the present invention and the polypeptide(s). Such structures may be obtained as a result of:

chemical coupling of at least one polypeptide(s) according to the invention to CyaA or its fragments. Methods for chemically coupling a polypeptide to CyaA or its fragments are well known in the art and comprise for example disulfide linkage(s), preferably by using N-pyridyl sulfonyl-activated sulfhydryl. Since the native CyaA protein has no cysteine residue in its primary sequence, a cysteine residue is genetically introduced into the CyaA protein, in particular in its catalytic domain, preferably into a permissive site as defined below (such as position 235) or at one of the CyaA extremities; and genetic link or genetic fusion of at least one polypeptide(s) to CyaA or its fragments. The genetic link or fusion includes the genetic insertion of the nucleic acid encoding the at least one polypeptide(s) according to the invention in frame into the nucleic acid encoding the CyaA protein or fragment thereof (i.e., without shifting the framework of the CyaA protein), preferably into the region of the catalytic domain of the CyaA protein, resulting in a recombinant protein. Thus, the at least one polypeptide(s) can be inserted into any permissive site of the CyaA protein (see WO 93/21324). As used herein, the term "permissive site" relates to a site where the polypeptide(s) can be inserted without substantially affecting the desired functional properties of the adenylate cyclase, i.e., without affecting the capacity of the CyaA protein to present said polypeptides to the immune system of the mammalian host, in particular without affecting the specific binding to CD11b/CD18 receptor and optionally without affecting the process of translocation of the polypeptide(s) into the cytosol of the target cell. Permissive sites of the Bordetella pertussis adenylate cyclase include, but are not limited to, residues 107-108 (Gly-His), 132-133 (Met-Ala), 137-138 (Val-Ala), 224-225 (Arg-Ala), 228-229 (Glu-Ala), 232-233 (Gly-Leu), 235-236 (Arg-Glu), 317-318 (Ser-Ala) and 335-336 (Gly-Gln) (Sebo et al., 1985; Glaser et al., 1988). For other Bordetella species, corresponding permissive sites can be defined by comparison of sequences and determination of corresponding residues (FIG. 2). According to another embodiment, the genetic link also includes the fusion of the nucleic acid encoding the at least one polypeptide(s) at one and/or other extremities of CyaA protein or its fragments.

When a CyaA protein (or its fragments) carries more than one polypeptide, these polypeptides may be either all carried by chemical coupling, all carried by genetic link (preferably all genetically inserted), or one(s) of them is(are) carried by chemical coupling whereas the other(s) is(are) carried by genetic link. In a particular embodiment, when all the polypeptides are genetically inserted into CyaA, preferably into permissive sites of CyaA, the polypeptides are inserted into different sites, preferably different permissive sites. In another embodiment, when all the polypeptides are genetically inserted into CyaA, preferably into permissive sites of CyaA, the polypeptides are inserted into the same site, preferably into the same permissive site.

The term "polypeptide" refers to a concatenation of amino acids, and is at least 9 amino acids residues and is in particular from 9 to 500 residues, 9 to 200, from 9 to 100, from 9 to 50 residues, or from 30 or 50 to 500 or to 200 residues, or from 100 to 500 or from 100 to 200 residues in length. Within the invention, the term "polypeptide" means a polypeptide which is able, once carried by the vector molecule, to induce an immune response, in particular a T cell immune response, against epitope(s) contained in this polypeptide. The polypeptide(s) contained in the vector molecule(s) may be derived from a tumor antigen, i.e., a peptide expressed by tumor or by cancerous cells, whether the tumor is self or induced by a pathogen; the tumor antigen may be self (in particular of human origin) or from the pathogen inducing the tumor.

The term "tumor antigen" encompasses the following groups of tumor antigens, and the polypeptide(s) contained in the vector molecule(s) of the invention may be chosen in at least one of the following groups: (a) oncofetal tumor antigens, (b) oncoviral tumor antigens, (c) overexpressed/accumulated tumor antigens, expressed in a wide variety of normal tissues and overexpressed in tumors, (d) shared tumor-specific antigens or cancer-Testis antigens, expressed in many tumors but not in normal tissues (including BAGE family, GAGE family, MAGE family, SAGE family and XAGE family), (e) lineage-restricted tumor antigens, (f) mutated tumor antigens, resulting from point mutations in genes that are ubiquitously expressed; and (g) differentiation tumor antigens, expressed in the normal tissue of origin of the tumors but which are not tumor-specific.

In a particular embodiment, when more than one polypeptide is used in a single vector molecule for elicitation of immunotherapeutic response or a single vector molecule for elicitation of an immunoprophylactic response, all the polypeptides are derived from tumor antigens.

In another embodiment, the polypeptide(s) contained in the vector molecule(s) may also or alternatively be derived from an antigen of pathogen, i.e., an antigen which is produced by the pathogen in the infected mammalian host, and possibly processed in the cells of said infected mammalian host or a component of said pathogen. Examples of pathogen antigens are a bacterial antigen, a viral antigen, a fungus antigen or a parasite antigen. In these examples, as a particular embodiment, one can distinguish pathogens involved in tumorigenesis (oncopathogens) and pathogens which are not involved in tumorigenesis. Examples of pathogens are intracellular pathogens, in particular pathogens inducing T-cell immune response(s) in their host. Thus, the polypeptide(s) may be derived from, but not limited to, Chlamydia, Plasmodium, Leishmania, Mycobacterium tuberculosis, HIV, HPV, HBV, HCV, adenoviruses, EBV, herpes virus, HTLV.1 virus and CMV. In a particular embodiment, the polypeptide(s) contained in the vector molecule(s) may be derived from a surface protein of the pathogen (such as the envelope protein of HIV) or derived from a polypeptide interacting with the machinery of the infected cell (such as E6 or E7 of HPV).

In a particular embodiment, when more than one polypeptide is used, in a single vector molecule or in a combination of vectors, all the polypeptides are derived from antigens of pathogens, possibly of distinct pathogens, genus or species.

In a particular embodiment, the polypeptides contained in the vector molecule(s) are all derived from bacterial antigens, are all derived from viral antigens, are all derived from fungus antigens or are all derived from parasite antigens. In another embodiment, the distinct polypeptides contained in the vector molecule(s) described herein are derived independently from a bacterial antigen, a viral antigen, a fungus antigen or a parasite antigen. In another embodiment, the polypeptides, in a single vector molecule or in a combination of vectors, are derived from tumor and derived from a pathogen.

The expression "derived from", with respect to a polypeptide carried by a vector molecule, means either the full-length antigenic protein, or a fragment of this antigenic protein, or a synthetic, non-natural polypeptide carries epitope(s) consisting of several parts of the antigenic protein fused together or a synthetic, non-natural polypeptide consisting of one or several part(s) of several proteins fused together, provided that the fragment or the synthetic, non-natural polypeptide is able to induce, once carried by the vector molecule(s), an immune response, in particular a T cell immune response, against an antigenic determinant contained in this fragment or polypeptide. According to this definition, the polypeptide(s) carried by the vector molecule(s) is or comprises a unique epitope, or is or comprises a group of epitopes. The expression "group of epitopes" encompasses at least one epitope, i.e., one epitope or more, in particular between 10 and 500 epitopes, between 50 and 200 epitopes and between 80 and 150 epitopes. In a particular embodiment, the expression "group of epitopes" means 1, 2, 3, 4, 5, 6, 7, 8, 9 or 10 epitopes. In a particular embodiment, the polypeptide(s) carried by the vector molecule(s) is or comprises a polyepitope, i.e., a polypeptide with at least two epitopes, in particular at least two T-cell epitopes. Epitopes within the present invention are, either linear or conformational, preferably linear, and are any amino acid sequence involved in the induction of a cell-mediated immune response, especially a T cell immune response. Accordingly, epitopes in the vector-carried polypeptide(s) described herein include those which are processed by APC (Antigen Presenting Cells) in a host, especially T epitopes recognized in association with class I MHC (Major Histocompatibility Complex) molecules, such as epitopes which target cells are $CD8^+$ T lymphocytes or T epitopes recognized in association with class II MHC molecules, such as those which target cells are CD4+ T lymphocytes. In a particular embodiment, the polypeptide(s) also contains B epitope(s) involved in humoral response. In a particular embodiment, the polypeptide(s) carried by the vector molecule(s) consists or comprises several different or several identical epitopes.

According to the invention, the vector-carried polypeptide(s) contain(s) at least two different groups of epitopes, i.e., one group of epitopes is able to elicit a T cell immune response to enable an immunotherapeutic treatment of first determined pathological condition(s) diagnosed in a mammalian host, whereas the second group of epitopes is able to elicit a T cell memory immune response to enable the prophylaxis against second determined pathological condition(s) in the same mammalian host. In a particular embodiment, the first group of epitopes is optionally able to elicit, in addition to a T cell response providing immunotherapeutic treatment of first determined pathological condition(s) diagnosed in a mammalian host, a T cell memory immune response against said first group of epitopes contained in said polypeptide(s) to enable the prevention against the re-occurrence of said first determined pathological condition(s).

According to the invention, in the absence of said second group of epitopes in said vector-carried polypeptide(s), the prophylaxis against second determined pathological condition(s) is not observed. This means that the second group of epitopes as defined herein is necessary to obtain the prophylaxis against second determined pathological condition(s).

In a particular embodiment, the second group of epitopes [within the vector-carried polypeptide(s)] is necessary and sufficient to obtain the prophylaxis against second determined pathological condition(s); in this embodiment, the contribution of the sole second group of epitopes, in the elicited immune reponse, is sufficient to obtain the prophylaxis against second determined pathological condition(s). In other words, there is causal relationship between the administration of said second group of epitopes and said prophylactic response.

In another embodiment, the second group of epitopes [within the vector-carried polypeptide(s)] is necessary to obtain the prophylaxis against second determined pathological condition(s), but is not sufficient or benefits from the contribution of the first group, meaning that the prophylaxis against second determined pathological condition(s) is obtained following a synergy between the immune response elicited against the second group of epitopes and the immune response elicited against the first group of epitopes. In this later case, the contribution of both groups of epitopes is necessary to obtain the prophylaxis against second determined pathological condition(s).

The necessary contribution of the second group of epitopes in the prophylaxis against second determined pathological condition(s) may be put in evidence by comparing the effect of the administration of the vector-carried polypeptide(s) of the invention on said second determined pathological condition(s) [the term prophylaxis is defined below] in the two following groups of mammals, in particular in two following groups of mice: (1) mammals administered with vector-carried polypeptide(s) of the invention that do(es) not bear a second group of epitopes as defined in the application and (2) mammals administered with vector-carried polypeptide(s) of the invention that bear(s) a second group of epitopes as defined in the application.

As understood by the expression "wherein said prophylaxis against second determined pathological condition(s) is not observed when said second group of epitopes is not contained in said administered vector-carried polypeptide(s)", it is excluded that the first group of epitopes as defined herein be sufficient (i.e., alone) to obtain the prophylaxis against second determined pathological condition(s).

Thus, in a particular embodiment, the amino acid sequence of the first group of epitopes (or polypeptide(s) consisting of this first group of epitopes) is different from the amino acid sequence of the second group of epitopes (or polypeptide(s) consisting of this second group of epitopes). The term "different" means that both sequences differ by at least 50%, at least 60%, at least 70%, at least 80%, at least 90%, or at least 95%, calculated over the entire length of the sequence of the polypeptides (global alignment calculated for example by the Needleman and Wunsch algorithm). In an alternative definition or in a particular embodiment of said "different sequences", at least 50%, at least 60%, at least 70%, at least 80%, at least 90% of the epitopes of the first group have a sequence which is different from the sequence of the epitopes of the second group. In a further particular embodiment, the first and second groups of epitopes (or the polypeptide(s) consisting of the first group of epitopes and the polypeptide(s) consisting of the second group of epitopes) have no epitope sequence in common. In a particular embodiment, the T-cell immune response obtained against the first group of epitopes is effective against the pathological condition(s) associated with said first group of epitopes and is not effective or not specifically effective against a pathological condition(s) associated with the second group of epitopes. Hence, in a particular embodiment, the T-cell immune response obtained against a group of epitopes is specific for this group, i.e., the T cells involved in the immune response against this group of epitopes does not recognize the other group of epitopes.

In a particular embodiment, the polypeptide(s) contain at least one epitope from HPV strains, especially HPV strains selected among the genus Alpha-papillomavirus, Beta-papillomavirus, Gamma-papillomavirus, Delta-papillomavirus, Epsilon-papillomavirus, Zeta-papillomavirus, Eta-papillomavirus, Theta-papillomavirus, Iota-papillomavirus, Kappa-papillomavirus, Lambda-papillomavirus, Mu-papillomavirus, Nu-papillomavirus, Xi-papillomavirus, Omikron-papillomavirus and Pi-papillomavirus. In a particular embodiment, papillomaviruses having a human tropism, such as strains from genus Alpha-papillomavirus, Beta-papillomavirus, Gamma-papillomavirus, Mu-papillomavirus or Nu-papillomavirus, are preferred. In a more particular embodiment, the polypeptide(s) contain at least one epitope from HPV strains from the Alpha-papillomavirus genus, especially strain from HPV species 7 and 9 of the Alpha-papillomavirus genus (de Villiers et al. Virology 2004). Thus, the polypeptide(s) contain at least one epitope from HPV highly oncogenic type species such as HPV16, HPV18, HPV31, HPV33, HPV35, HPV45, HPV52 or HPV58. Among these type species, HPV18 and HPV16 are of particular interest. In an embodiment, the polypeptides carried by the vector molecule(s) described herein are from different HPV strains or different HPV type species chosen among the ones disclosed above. In another particular embodiment, and whatever the HPV strains or HPV type species, the polypeptides are derived from the L1, L2, E1, E2, E4, E5, E6 or E7 proteins, with a particular interest for polypeptides bearing epitopes from E6 or E7 proteins of HPV strains or HPV type species. In a particular embodiment, the polypeptides carried by the vector molecule(s) described herein are from the same HPV protein but from different HPV strains or different HPV type species chosen among the ones disclosed above. In a particular embodiment of the invention, E6 or E7 proteins of HPV16 and E6 or E7 proteins of HPV18 are used for the design of polypeptides, more preferably the E7 protein of HPV16 and HPV18 HPV type species. According to a particular embodiment of the invention, a vector molecule carries several polypeptides, preferably by genetic insertion, each of them containing or consisting of one or several epitopes of one or several HPV proteins of at least two distinct HPV strains or two distinct HPV type species. Thus, a particular embodiment is vector-carried polypeptides consisting of a CyaA protein or fragment thereof carrying a polypeptide or several polypeptides encompassing epitopes derived from the E6 or the E7 protein from both HPV16 and HPV18 HPV type species. In another embodiment, the invention concerns a composition comprising a first vector molecule carrying a polypeptide or several polypeptides encompassing epitopes derived from the E6 or the E7 protein from HPV16 (the first vector-carried polypeptides with a first group of epitopes) and a separate vector molecule carrying a polypeptide or several polypeptides encompassing epitopes derived from the E6 or the E7 protein from HPV18 (the separate vector-carried polypeptides with a second group of epitopes). When several polypeptides are carried by a single vector molecule, these polypeptides may consist of different fragments of the same protein, for example of an E7 or E6 protein, which are inserted in different sites, in particular permissive sites, of the vector molecule.

Thus, a composition used within the present invention comprises a vector-carried polypeptide(s) whose polypeptide(s) is/are derived from the E7 protein of HPV16 and a vector-carried polypeptide(s) whose polypeptide(s) is/are derived from the E7 protein of HPV18. An example of such composition comprises:

(a) a first vector molecule carrying a first polypeptide which is a fragment comprising residues 1 to 29 or a fragment consisting of residues 1 to 29 of E7 of HPV16 and carrying a second polypeptide which is a fragment comprising residues 43 to 98 or a fragment consisting of residues 43 to 98 of E7 protein of HPV16. In a preferred embodiment, the first polypeptide is the first 29 amino acid residues of HPV16-E7 and is inserted between codons 319 and 320 of CyaA, and the second polypeptide consists of residues 43 to 98 of HPV16-E7 and is inserted between codons 224 and 235 of CyaA (exemplified in the pKTRACE5-HPV16E7$_{\Delta30\text{-}42}$ vector); and (b) a separate vector molecule carrying a first polypeptide which is a fragment comprising residues 1 to 31 of E7 of HPV18 or a fragment consisting of residues 1 to 31 of E7 of HPV18, and a second polypeptide which is a fragment comprising residues 43 to 105 of E7 of HPV18 or a fragment consisting of residues 43 to 105 of E7 of HPV18. In a preferred embodiment, the first polypeptide is the first 31 amino acid residues of HPV18-E7 and is inserted between codons 319 and 320 of CyaA, and the second polypeptide consists of residues 43 to 105 of HPV18-E7 and is inserted between codons 224 and 235 of CyaA (exemplified in the pKTRACE5-HPV18E7$_{\Delta32\text{-}42}$ vector).

In another embodiment, the polypeptide(s) contain at least one epitope derived from the MAGE A3 tumor antigen, such as a polypeptide consisting of residues 97 to 178 of MAGE A3 (SEQ ID NO:8), or such as a polypeptide consisting of residues 190 to 221 fused to residues 242 to 295 of MAGE A3 (SEQ ID NO:9). In a particular embodiment, a vector-carried polypeptide(s) of the invention (or a composition contained it) consists of a CyaA protein, preferably B. pertussis CyaA, in which two polypeptides derived from MAGE A3 have been inserted in two different sites. Such a vector-carried polypeptide(s) consists of the B. pertussis CyaA, wherein (1) a first polypeptide consisting of residues 97 to 178 of MAGE A3 has been inserted between codons 319 and 320 of CyaA and (2) a second polypeptide consisting of residues 190 to 221 fused to residues 242 to 295 of MAGE A3 has been inserted between codons 234 and 235 of CyaA. A particular example of a CyaA-MAGE A3 vector is provided in FIG. 4C (SEQ ID NO:7).

The vector-carried polypeptide(s) as defined herein, as such or in a composition, is/are used to obtain in a same mammalian host, especially in a human host, (i) an immunotherapeutic treatment of first determined pathological condition(s) diagnosed in said mammalian host by eliciting a T cell immune response against a first group of epitopes contained in said polypeptide(s) and (ii) the prophylaxis against second determined pathological condition(s) by eliciting a T cell memory immune response against a second group of epitopes contained in said polypeptide(s), and (iii) optionally the prevention against the re-occurrence of said first determined pathological condition(s) by eliciting a T cell memory immune response against said first group of epitopes contained in said polypeptide(s), said immune responses being obtained after administration of said vector-carried polypeptide(s) into said host, wherein said prophylaxis against second determined pathological condition(s) is not observed when said second group of epitopes is not contained in said administered vector-carried polypeptide(s). According to an embodiment of the invention, the polypeptide(s), as defined herein, carried by the vector molecule(s), are chosen according to the groups of epitopes which is sought and may be classified according to two groups:

the first group of epitopes concerns polypeptide(s) which is/are derived from an antigen that is known to be expressed by or presented to the immune system in a mammalian host infected by a particular pathogen, developing a particular tumor or presenting with first determined pathological condition(s), said mammalian host having been diagnosed with said particular infection, said particular tumor or said first determined pathological condition(s) before administration of the vector-carried polypeptide(s) or composition defined herein; and the second group of epitopes concerns polypeptide(s) which is/are derived from an antigen that is known to be expressed by or presented to the immune system in a mammalian host infected by another particular pathogen, developing another particular type of tumor or presenting second determined pathological condition(s), said mammalian host not being or not having been infected by said another particular pathogen, not having developed said another particular type of tumour or not having presented said second determined pathological condition(s) before administration of the vector-carried polypeptide(s) or composition defined herein.

The invention lies from the observations that:

(i) an immunotherapeutic treatment of first determined pathological condition(s) diagnosed in a mammalian host can be obtained by eliciting a T cell immune response against a first group of epitopes contained in polypeptide(s) carried by a vector molecule;

(ii) the prophylaxis against second determined pathological condition(s) in the same mammalian host can be obtained by eliciting a T cell memory immune response against a second group of epitopes contained in polypeptide(s); and (iii) optionally, the prevention against the re-occurrence of said first determined pathological condition(s) can be obtained by eliciting a T cell memory immune response against said first group of epitopes contained in said polypeptide(s) carried by a vector molecule;

said second group of epitopes being either carried by the same vector molecule, or carried by a separate vector molecule, and administered in the same composition as and simultaneously with the first vector molecule.

Therefore, the vector molecule as such as defined herein or in a composition, or the vector molecules of a composition as defined herein carries at least one, preferably one, polypeptide comprising epitope(s) of the first group and at least one polypeptide comprising epitope(s) of the second group. In other embodiments, the vector molecule as such as defined herein or in a composition or the vector molecules of a composition as defined herein carries/carry (a) one polypeptide comprising epitope(s) of the first group and at least one polypeptide comprising epitope(s) of the second group, (b) one polypeptide comprising epitope(s) of the first group and at least one polypeptide comprising epitope(s) of the second group selected among 1, 2, 3, 4, 5 or 6 polypeptides, (c) at least one polypeptide comprising epitope(s) of the first group selected among 2 or 3 polypeptides and at least one polypeptide comprising epitope(s) of the second group and (d) at least one polypeptide comprising epitope(s) of the first group selected among 2 or 3 polypeptides and at least one polypeptide comprising epitope(s) of the second group selected among 1, 2, 3, 4, 5 or 6 polypeptides.

When one vector-carried polypeptide(s) is used as such or in a composition, the vector may carries one polypeptide comprising epitope(s) of the first group and epitope(s) of the second group, i.e., that said second group of epitopes is contained in the same polypeptide as the first group of epitopes.

In another embodiment, said first and second group of epitopes are contained in different polypeptides. The polypeptide comprising epitope(s) of the first group and the polypeptide comprising epitope(s) of the second group may be carried by the same vector molecule. In another embodiment, the polypeptide comprising epitope(s) of the first group and the polypeptide comprising epitope(s) of the second group may be carried by different vector molecules and included in a same composition. When a composition, containing a first and a second, separate, vector-carried polypeptide(s), is used, the first vector molecule-carries at least one polypeptide comprising epitope(s) of the first group, meaning that one polypeptide comprising epitope(s) of the first group at the minimum is carried by said first vector molecule. In the same composition, the second vector molecule carries at least one polypeptide comprising epitope(s) of the second group, meaning that one polypeptide comprising epitope(s) of the second group at the minimum is carried by said second separate vector molecule. Finally, optional one or more (e.g. 1, 2, 3, 4, 5 or 6) vector-carried polypeptide(s) may also be included in said composition, whatever the group of epitopes contained in this/these vector-carried polypeptide(s).

By "immune response", it is meant a cell-mediated immune response, especially a T-cell mediated immune response. In a particular embodiment, said T-cell mediated immune response is a cell-mediated cytotoxic immune response CTL, especially a $CD8^+$ immune response. In the case of polypeptide(s) derived from tumor antigen, the immune response is preferably a tumor-specific cytotoxic immune response, involving tumor-specific cytotoxic lymphocytes. In a particular embodiment, said T-cell mediated immune response is a $CD4^+$ immune response, especially a T-helper immune response. In a particular embodiment, the immune response, in particular the immune response(s) induced against the epitopes of the second group (as defined herein), following the administration of the vector-carried polypeptide(s) or composition defined herein, is a memory T cell immune response. The expression "immune response" may also encompass, in addition to a cell-mediated immune response as defined above, a humoral immune response (production of antibodies). The immune responses discussed within the present application are obtained after administration, into the host, of the vector-carried polypeptide(s) of the invention, as such or within a composition.

The expression "immunotherapeutic treatment" refers to the treatment of a (first) determined pathological condition(s) diagnosed in a mammalian host, by eliciting especially a T-cell immune response against a first group of epitopes contained in the polypeptide(s) carried by the administered vector molecule(s) as defined herein. The use of the vector-carried polypeptide(s) or composition as defined herein aims at improving the clinical condition(s) of a mammalian host, in need thereof, who has been diagnosed as infected by a pathogen or as suffering from a pathological state, such as tumor, or aims at the elimination of the causative agent or organism of the disease, or at lowering said agent or organism. In a situation of pathogen infection, the immunotherapeutic treatment results in a significant decrease in the pathogen load at the site of infection or at the site of replication of this pathogen, in particular in the plasma or in the mucosa of the host, and possibly results in a pathogen load, such as plasma load, which is less than what can be detected when measured or, at lowering the size or the development of the tumor if any.

The expression "immunoprophylaxis" or "prophylaxis" refers to a response that prevents or protects against the exposure, infection, onset or the development of a second determined pathological condition(s) or disease or clinical consequences thereof in the same mammalian host by eliciting especially a T cell memory immune response against a second group of epitopes contained in the polypeptide(s) carried by the administered vector molecule(s) as defined herein. The use of the vector-carried polypeptide(s) or composition as defined herein results in a prophylactic immune response against future infection, future malignant events or diseases and accordingly prevents the occurrence of a pathological state in said mammalian host.

The efficacy of the response in conferring prophylaxis can be assayed by detecting marker of the pathological state. In a particular embodiment, the efficacy criteria are selected to reach statistical relevancy.

The expression "prevention against the re-occurrence" refers to the elicitation of an immune response to prevent a novel future exposure, novel future infection, novel future onset or novel future development of the first determined pathological condition(s), conditions which have been previously diagnosed and have been treated following the administration of the vector-carried polypeptide(s) or composition as defined herein.

The expression "mammalian host" encompasses all mammals, in particular primates and humans (e.g., patient).

It is understood that, following the administration(s) of the vector-carried polypeptide(s) or composition as defined herein, both the T cell immune response against a first group of epitopes and the T cell memory immune response against a second group of epitopes and optionally response against said first group of epitopes, are induced in the same mammalian host, within a particular window of time. Thus, the at least one administration of the vector-carried polypeptide(s) or composition as defined herein leads to the induction of a T cell immune response against a first group of epitopes and a T cell memory immune response against a second group of epitopes and optionally a T cell memory immune response against said first group of epitopes, which can be put in evidence and/or measured from 1 month to 12 months or more post administration (in particular at 2, 3, 6, 9 or 12 months), though T-cell involved in one of these or in these both immune responses may still be put in evidence several years post administration. The expression "at least one administration" or "administering once" means that the vector-carried polypeptide(s) or composition as defined herein is administered into the mammalian host, especially the patient, once or more, preferably once or twice. Each administration consists in at least one vector-carried polypeptide(s), provided that a first group of epitopes and a second group of epitopes contained in at least one polypeptide(s) carried by at least one vector molecule(s), with at least one epitope of said second group of epitopes, are administered to the mammalian host at the same time. If appropriate, the second and possible subsequently administrations (prime-boost) are carried out with the same vector-carried polypeptide(s) or with the same composition, regarding the polypeptide(s), as the first administration. The experiments reported hereinafter show that an immunotherapeutic treatment and prophylaxis, and optionally prevention against the re-occurrence, may be obtained following a single administration of the vector-carried polypeptide(s) or composition as defined herein.

In a particular embodiment, the invention relates to the vector-carried polypeptide(s) or composition as defined herein for use (i) in the immunotherapeutic treatment of first pathological condition(s) consecutive to a pathogen infection, in particular consecutive to a bacterial or viral infection, diagnosed in a mammalian host and (ii) in the prophylaxis against second pathological condition(s) consecutive to an infection by a different pathogen, in particular consecutive to an infection by a different bacteria or different virus (or different strain thereof) and (iii) optionally in the prevention against the re-occurrence of said first pathological condition(s), wherein said prophylaxis against said second determined pathological condition(s) is not observed when the second group of epitopes linked to said different pathogen (e.g., different bacteria or different virus) is not contained in said administered vector-carried polypeptide(s). In the particular case of pathological condition(s) consecutive to different virus strains, especially different HPV strains or different HPV type species, the invention relates to the vector-carried polypeptide(s) or composition as defined herein for use (i) in the immunotherapeutic treatment of first pathological condition(s) consecutive to the infection by a first virus, first HPV strain or first HPV type strains, diagnosed in a mammalian host and (ii) in the prophylaxis against second pathological condition(s) consecutive to the infection by a second different virus, second different HPV strain or second different HPV type strain, and (iii) optionally in the prevention against the re-occurrence of said first pathological condition(s), wherein said prophylaxis against second determined pathological condition(s) is not observed when the second group of epitopes linked to said second different virus, second different HPV strain or second different HPV type strain is not contained in said administered vector-carried polypeptide(s). In a preferred embodiment, the invention relates to vector-carried polypeptide(s) or composition as defined herein, comprising a polypeptide which is derived from the E7 protein of HPV16 and a polypeptide which is derived from the E7 protein of HPV18, for use either: (1) (i) in the immunotherapeutic treatment of first pathological condition(s) consecutive to the infection by HPV16, diagnosed in a mammalian host and (ii) in the prophylaxis against second pathological condition(s) consecutive to the infection by HPV18 and (iii) optionally in the prevention against the re-occurrence of said first pathological condition(s), wherein said prophylaxis against second determined pathological condition(s) is not observed when the polypeptide derived from the E7 protein of HPV18 is not contained in said administered vector-carried polypeptide(s); or (2) (i) in the immunotherapeutic treatment of first pathological condition(s) consecutive to the infection by HPV18, diagnosed in a mammalian host and (ii) in the prophylaxis against second pathological condition(s) consecutive to the infection by HPV16 and (iii) optionally in the prevention against the re-occurrence of said first pathological condition(s), wherein said prophylaxis against second determined pathological condition(s) is not observed when the polypeptide derived from the E7 protein of HPV16 is not contained in said administered vector-carried polypeptide(s).

In a particular embodiment, the invention relates to the vector-carried polypeptide(s) or composition as defined herein for use (i) in the immunotherapeutic treatment of first pathological condition(s) consecutive to first tumor cells, diagnosed in a mammalian host and (ii) in the prophylaxis against second pathological condition(s) consecutive to second tumor cells, whose origin and/or histology is different from the first tumor cells, and (iii) optionally in the prevention against the re-occurrence of said first pathological condition(s), wherein said prophylaxis against second determined pathological condition(s) is not observed when the second group of epitopes linked to said second tumor cells is not contained in said administered vector-carried polypeptide(s).

In a particular embodiment, the invention relates to the vector-carried polypeptide(s) or composition as defined herein for use (i) in the immunotherapeutic treatment of first pathological condition(s) consecutive to a pathogen infection, in particular consecutive to a bacterial or viral infection, diagnosed in a mammalian host and (ii) in the prophylaxis against second pathological condition(s) consecutive to the development of tumor cells and (iii) optionally in the prevention against the re-occurrence of said first pathological condition(s), wherein said prophylaxis against second determined pathological condition(s) is not observed when the second group of epitopes linked to said tumor cells is not contained in said administered vector-carried polypeptide(s).

In a particular embodiment, the invention relates to the vector-carried polypeptide(s) or composition as defined herein for use (i) in the immunotherapeutic treatment of first pathological condition(s) consecutive to the development of tumor cells, diagnosed in a mammalian host and (ii) in the prophylaxis against second pathological condition(s) consecutive to a pathogen infection, in particular consecutive to a bacterial or viral infection, and (iii) optionally in the prevention against the re-occurrence of said first pathological condition(s), wherein said prophylaxis against second determined pathological condition(s) is not observed when the second group of epitopes linked to said different pathogen (e.g., different bacteria or different virus) is not contained in said administered vector-carried polypeptide(s).

The invention also relates to a method to obtain in a same mammalian host, both (i) an immunotherapeutic treatment of first determined pathological condition(s) diagnosed in a mammalian host, especially by eliciting a T cell immune response against a first group of epitopes, and (ii) the prophylaxis against second determined pathological condition(s), especially by eliciting a T cell memory immune response against a second group of epitopes, wherein said prophylaxis against second determined pathological condition(s) is not observed when said second group of epitopes is not contained in said administered vector-carried polypeptide(s), said method comprising administering, at least once, to said mammalian host either:

(1) a vector-carried polypeptide(s), wherein said vector carrying the polypeptide(s) consists in a CyaA protein or a fragment thereof suitable to present said polypeptide(s) to the immune system in a mammalian host, said first group of epitopes and second group of epitopes being contained in at least one polypeptide(s) carried by said vector, and at least one epitope of said second group of epitopes being different from the epitopes of the first group of epitopes;

(2) a composition comprising the vector-carried polypeptide(s) as defined in (1) in combination with a pharmaceutically acceptable vehicle; or (3) a composition comprising (a) a first vector-carried polypeptide(s) wherein said first vector carrying the polypeptide(s) consists in a CyaA protein or a fragment thereof suitable to present said polypeptide(s) to the immune system in a mammalian host, said first group of epitopes being contained in at least one polypeptide(s) carried by said first vector and (b) a second, separate, vector-carried polypeptide(s) wherein said second vector molecule carrying the polypeptide(s) consists in a CyaA protein or a fragment thereof suitable to present said polypeptide(s) to the immune system in a mammalian host, said second group of epitopes being contained in at least one polypeptide(s) carried by said second vector.

In an embodiment, the invention also relates to a method to obtain in a same mammalian host, (i) an immunotherapeutic treatment of first determined pathological condition(s) diagnosed in a mammalian host, especially by eliciting a T cell immune response against a first group of epitopes, (ii) the prophylaxis against second determined pathological condition(s), especially by eliciting a T cell memory immune response against a second group of epitopes and (iii) optionally the prevention against the re-occurrence of said first determined pathological condition(s), especially by eliciting a T cell memory immune response against said first group of epitopes, wherein said prophylaxis against second determined pathological condition(s) is not observed when said second group of epitopes is not contained in said administered vector-carried polypeptide(s), said method comprising administering at least once to said patient either:

(1) a vector-carried polypeptide(s), wherein said vector carrying the polypeptide(s) consists in a CyaA protein or a fragment thereof suitable to present said polypeptide(s) to the immune system in a mammalian host, said first group of epitopes and second group of epitopes being contained in at least one polypeptide(s) carried by said vector, and at least one epitope of said second group of epitopes being different from the epitopes of the first group of epitopes;

(2) a composition comprising the vector-carried polypeptide(s) as defined in (1) in combination with a pharmaceutically acceptable vehicle; or (3) a composition comprising (a) a first vector-carried polypeptide(s) wherein said first vector carrying the polypeptide(s) consists in a CyaA protein or a fragment thereof suitable to present said polypeptide(s) to the immune system in a mammalian host, said first group of epitopes being contained in at least one polypeptide(s) carried by said first vector and (b) a second, separate, vector-carried polypeptide(s) wherein said second vector molecule carrying the polypeptide(s) consists in a CyaA protein or a fragment thereof suitable to present said polypeptide(s) to the immune system in a mammalian host, said second group of epitopes being contained in at least one polypeptide(s) carried by said second vector.

The compositions as defined herein may, in a particular embodiment, comprise a pharmaceutically acceptable vehicle or formulation, or physiologically acceptable diluent, which is chosen among buffering agents, saline, phosphate buffered saline, dextrose, glycerol, water, ethanol and the like and combinations thereof.

Moreover, the vector-carried polypeptide(s) or the composition as defined herein as means to obtain an immunotherapeutic treatment and the prophylaxis may be combined or mixed with, or the composition as defined herein as means to obtain an immunotherapeutic treatment and the prophylaxis may further comprise, at least one immunopotentiator, such as at least one adjuvant, preferably one adjuvant, and/or a surfactant and/or immunomodulatory substances (such as cytokines or chemokines). Various adjuvants are known in the art and include Complete Freund's Adjuvant (CFA), Incomplete Freund's Adjuvant (IFA), montanide ISA (incompletre seppic adjuvant), muramyl peptides such as muramyl dipeptide (MDP) MDP-Lys (L18) (N$^\alpha$-acetylemuramyl-L-alanyl-D-isoglutaminyl-N$^e$steoroyl-L-lysine), zinc sulphate, colloidal iron hydroxide, calcium phosphate or calcium chloride, CpG oligodeoxynucleotides (CPG ODN) such as CPG ODN 1826 and CPG ODN 2007, MF59 which is a detergent stabilized oil-in water emulsion containing 5% squalene (w/v), 0.5% Tween® 80 (w/v) and 0.5% Span (w/v) in water, TLR4 ligands (such as MPL, GLA) TLR3 ligands (such as Hiltonol®), polysaccharides (such as Inulin) and liposomes (such as cationic liposomes, ISCOMs).

In a particular embodiment, the at least one adjuvant is chosen among molecules which have the capacity to activate T-cell immune response, in particular T-cell memory response. Preferred adjuvants are the ones that bind or are agonist to TLR (Toll like receptor) 3, 4, 7, 8 and/or 9 into immune cells (such as APC). In a particular embodiment, the adjuvant is a TLR ligand, in particular a TLR ligand selected from the group consisting of TLR ligands of class 3, such as poly-ICLC, TLR ligands of class 4, TLR ligands of class 9, such as CpG, and TLR ligands of class 7/8, such as Imiquimod. Examples of adjuvants are Imiquimod sold as a cream containing 5% Imiquimod (Aldara™) and Poly-ICLC sold by Oncovir (Inc, WA, US) as Hiltonal®.

By "combined", it is meant that the vector-carried polypeptide(s) or the composition as defined herein and the immunopotentiator are both put in contact with the host, at different times and/or by different modes of administration, preferably at the same site of contact. In a particular embodiment, the vector-carried polypeptide(s) or the composition as defined herein is injected into the host and the immunopotentiator (such as an adjuvant) is applied topically, e.g., cutaneously (onto the skin), to the host. For example, the vector-carried polypeptide(s) or the composition as defined herein is injected into the host and the immunopotentiator (such as an adjuvant) is applied onto the skin of the host following the injection, at the site of injection. In contrast, "mixed" means that the vector-carried polypeptide(s) or the composition as defined herein and the immunopotentiator are in the same formulation when administered.

It is noteworthy that in the present application, when an immunopotentiator (such as an adjuvant) is mixed or combined with the vector-carried polypeptide(s) or the composition as defined herein, the immunopotentiator is used, at least, each time the vector-carried polypeptide(s) or the composition of the invention is administered into the host. In a particular embodiment, the vector-carried polypeptide(s) or the composition of the invention is administered twice, and the immunopotentiator is applied (either mixed or combined, preferably cutaneously), at the site of administration of the vector-carried polypeptide(s) or the composition of the invention, the day of each administration. In another particular embodiment, the vector-carried polypeptide(s) or the composition of the invention is administered twice, and the immunopotentiator is applied (either mixed or combined, preferably cutaneously), at the site of administration of the vector-carried polypeptide(s) or the composition of the invention, the day of each administration and the day following the day of each administration. In a particular embodiment, the vector-carried polypeptide(s) or the composition of the invention is administered twice, and the adjuvant (preferably Imiquimod, such as Aldara™) is applied cutaneously at the site of administration of the vector-carried polypeptide(s) or the composition of the invention, the day of each administration and the day following the day of each administration.

The vector-carried polypeptide(s) as defined herein or the composition as defined herein as means to obtain an immunotherapeutic treatment and the prophylaxis and optionally the prevention against the re-occurrence, may additionally be combined or mixed, in administration regimens, with other active compounds suitable to treat pathogen infection, tumor cells or pathological condition(s) associated with this infection or tumor, such as antitumoral or antiviral active compounds.

The vector-carried polypeptide(s) or compositions defined herein can be injected in a patient via different routes: subcutaneous (s.c.), intradermal (i.d.), intramuscular (i.m.) or intravenous (i.v.) injection, oral administration and mucosal administration, especially intranasal administration or inhalation. In a particular embodiment, the vector-carried polypeptide(s) or compositions defined herein is/are administered intradermally.

In a particular embodiment, the vector-carried polypeptide(s) or compositions defined herein, either mixed or combined with at least one immunopotentiator or not, whatever the administration routes, is administered at a site, independent upon the (first) determined pathological condition(s) diagnosed in the mammalian host, i.e., for a tumor, at a site other than the one of the tumor development (for example other than mucosa), and for a pathogen, at a site other than the pathogen replication site.

The vector-carried polypeptide(s) or compositions defined herein may be in a solid form (cachet, powder, gelule, pill, suppository, quick release tablet, gastro-resistant tablet, delayed release tablet), a powder form, preferably after lyophilization (lyophilized form or lyophilized powder form) which needs to be reconstituted for example with diluents(s) before injection, or in a liquid form, such as an injectable solution or injectable suspension.

The quantity of vector-carried polypeptide(s) to be administered (dosage) depends upon the subject to be treated, including considering the condition of the patient, the state of the individual's immune system, the route of administration and the size of the host. The conventional dosages range from 1 to 1200 µg, 100 to 1000 µg, 200 to 1000 µg, 500 to 1000 µg. A particular dosage is chosen from the group consisting of 100, 200, 300, 400, 500, 600, 700, 800, 900 and 1000 µg. In another embodiment, conventional dosages range from 1 to 100 µg, 1 to 50 µg and 1 to 10 µg of vector-carried polypeptide(s). These examples can be modified by one skilled in the art, depending on circumstances.

Each specific embodiment may be combined with any particular embodiment.

EXAMPLES

A. Material and Methods

Mice

Six weeks-old female C57BL/6 mice (H-2$^b$) are purchased from Charles River Laboratories. Mice are housed under pathogen-free conditions with water and food ad libitum. Procedures involving animals and their care are conformed to Genticel guidelines that comply with national and international laws and policies and that are reviewed by the local ethical committee.

Tumour Cell Lines

TC-1 (tissue culture number one) tumour cells (Lin, Guarnieri et al. 1996) were prepared by transformation of C57BL/6 primary mouse lung cells with HPV16 E6 and E7 oncogenes and activated human c-Ha-Ras oncogene. The cells used in this study have been obtained from the ATCC.

TC1 cells are thawed before each experiment and are then cultured and expanded in vitro during at least 10 days before injection.

EG7, the OVA-transfected EL4 lymphoma murine cell line (C57BL/6 genetic background), are used to induce solid tumour expressing the Ovalbumin protein. This model is widely described and used as a murine tumour model of cancer (Schreiber, Deyev et al. 2009). EG7 cells are thawed before each experiment and are then cultured and expanded in vitro during at least 10 days before injection.

Tumour Cells Inoculation

On day 0, C57BL/6 mice are injected with TC-1 cells ($0.5 \times 10^6$ cells per mouse for HPV_TUR008, $1 \times 10^6$ cells per mouse for the others studies) diluted in 100 μL of PBS 1× via the subcutaneous route in the flank. In some experiments mice are injected at day 60 with EG7 cells diluted in 100 μL of PBS 1× via the subcutaneous route in the flank.

Vector Preparation

Figure 3B:
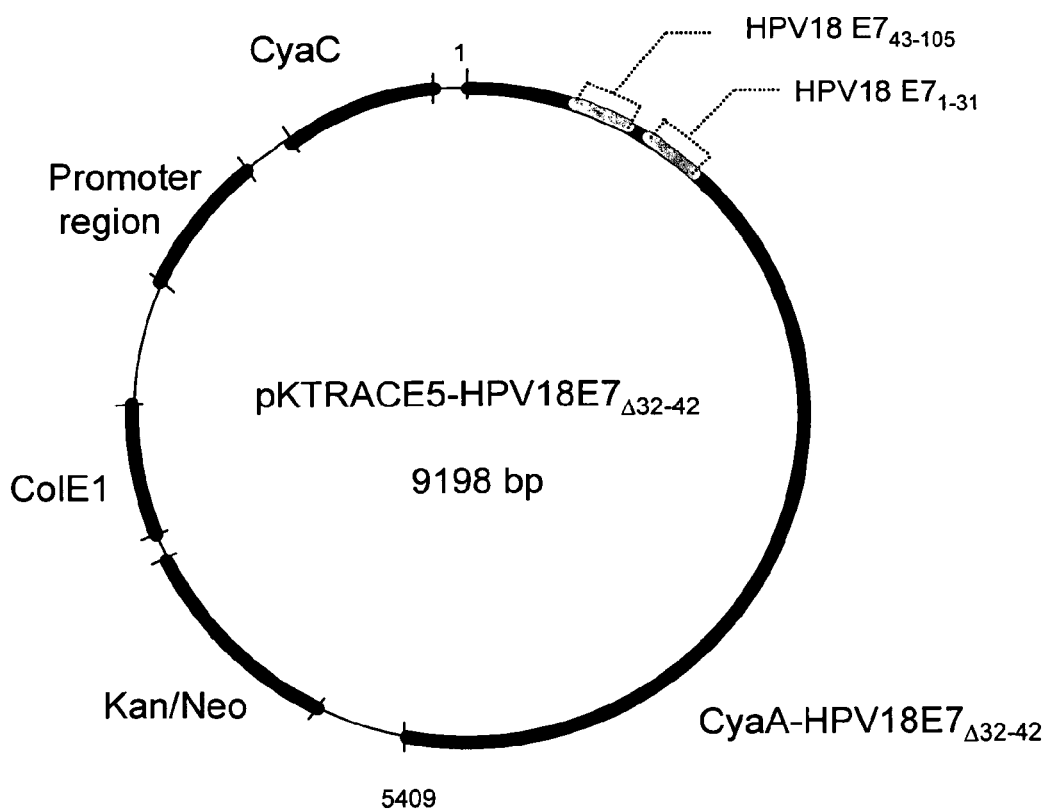
FIG. 3B. Schematic map of pkTRACE5 in which relevant restriction sites and inserted sequences are indicated for CyaA-HPV18E7$_{D32-42}$.

Construction and purification of recombinant CyaA-HPV16E7$_{\Delta 30-42}$ (C16-1) and CyaA-HPV18E7$_{\Delta 32-42}$ (C18-1) (FIGS. 3A and 3B) are already described in EP1576967B1. The two final bulks of CyaA-HPV16E7$_{\Delta 30-42}$ (C16-1) and CyaA-HPV18E7$_{\Delta 32-42}$ (C18-1) were mixed in Genticel at a 1:1 ratio in order to produce the ProCervix which is then stored at −80° C. in aliquots.

Figure 4A:
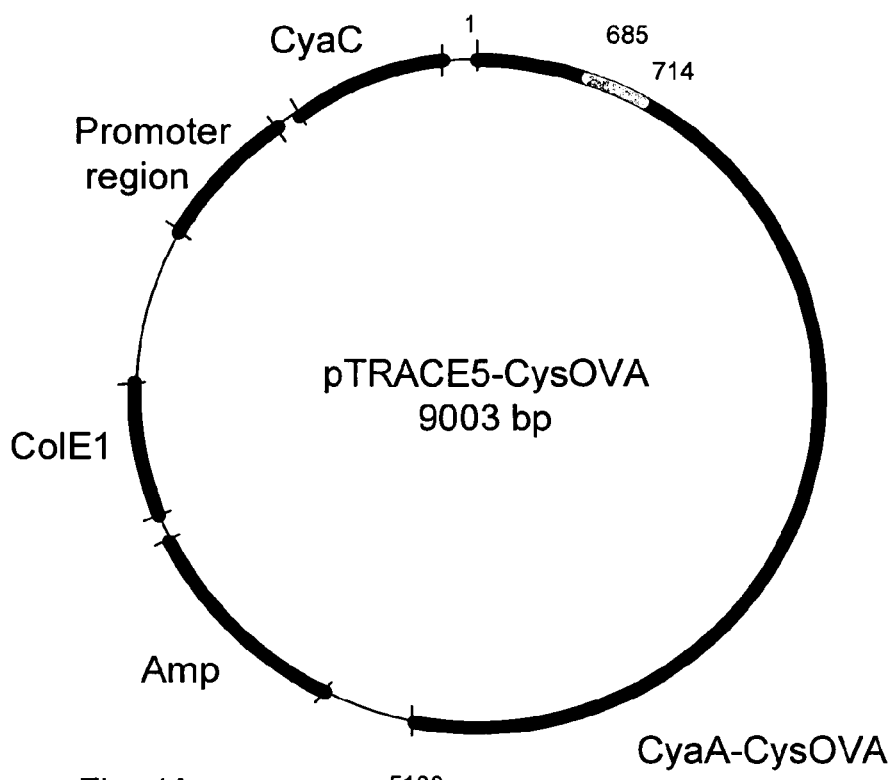
FIG. 4A. Schematic map of pTRACE5 in which relevant restriction sites and inserted sequences are indicated for CyaA-CysOVA.
Figure 4B:
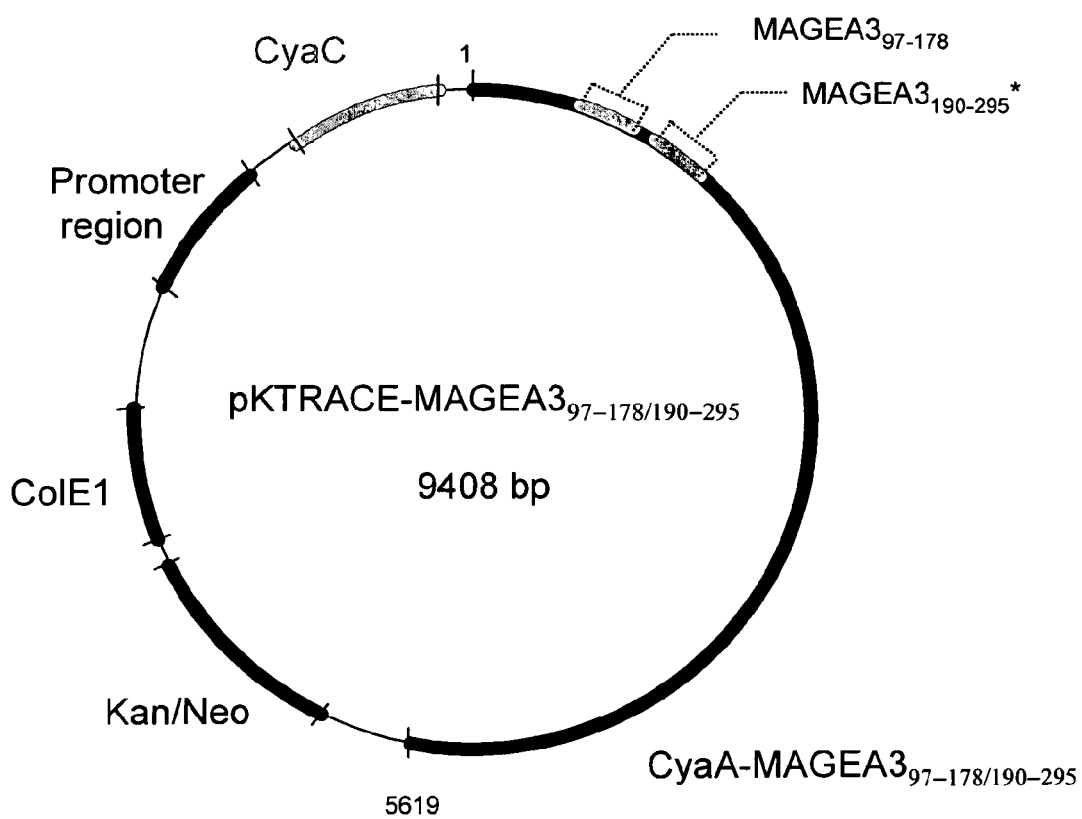
FIG. 4B. Schematic map of pkTRACE5 in which relevant restriction sites and inserted sequences are indicated for CyaA-MAGEA3$_{97-178/190-295}$. *MAGE-A3$_{190-295}$ represents residues 190 to 221 fused to residues 242 to 295 of MAGE A3. The numbers 97, 178, 190, 221, 242 and 295 indicate the position of the amino acid residues of the entire MAGE-A3 sequence.

CyaA-CysOVA embeds the OVA$_{257-264}$ (SIINFEKL) H-2$^b$ restricted epitope of the ovalbumin (OVA) protein. It is coded as BTpr_103, batch HPV043_Cova_PB_8M purified at Genticel. This batch of CyaA-CysOVA was characterized for its immunogenicity in mice at Genticel (internal results) (FIG. 4).

the CyaA-MAGEA3$_{97-178/193-295}$ vector (FIG. 4C and SEQ ID NO:7) encompasses two polypeptides:

(1) the MAGE A3$_{97-178}$ epitope inserted between residues 319 and 320 of B. pertussis CyaA: LGDNQIMPKAGLLI-IVLAIIAREGDCAPEEKIPKKLLTQHFVQENY LEY-RQVPGSDPACYEFLWGPRALVETSYVKVLHHM-VKISG (SEQ ID NO: 8); and (2) the MAGE-A3$_{190-295^*}$ epitope corresponding to residues 190-221 fused to residues 242-295 of the MAGE A3 sequence, inserted between residues 224 and 235 of CyaA: TFPDLESEFQAALSRKVAELVHFLLLKYRAREPVT-KAEMLGSVVGN WQYFFPVIFSKASSSLQLVF-GIELMEVDPIGHLYIF (SEQ ID NO:9).

Vaccine Administration

On day 11, after tumour measurement, mice with detectable solid tumours are vaccinated by intradermal (id) injection into ears dermis (both ears are injected). In some experiments, mice are receiving a two-shot vaccination at day 11 and day 39 post-TC-1 tumour cells inoculation. Regarding ProCervix, mice were administered with 5 μg of CyaA-HPV16E7$_{\Delta 30-42}$ and 5 μg of CyaA-HPV18E7$_{\Delta 32-42}$.

Adjuvant Molecules

Aldara™ is a pharmaceutical formulation of a molecule activating innate immunity via a preferential binding on TLR7 into immune cells as for example APC. This active molecule is Imiquimod, a small synthetic compound. Aldara™ is marketed as a cream containing 5% Imiquimod in 250 mg single-dose use packets (12.5 mg of active Imiquimod). The dose inducing an adjuvant effect for ProCervix mouse vaccination is 25 mg of Aldara™ per immunisation site so respectively 1.25 mg of active Imiquimod per site of injection (50 mg for one mouse). A topical (cutaneous) application of Aldara™ is done the day of the immunisation and 24 h after the immunisation. Individual tubes are prepared, each containing 25 mg of Aldara™ for application on ear skin (2 tubes for one mouse). In order to finely evaluate the real quantity of Aldara™ cream applied on each ProCervix injection site (corresponding to each ear for an individual mouse); each eppendorf tube is weighted before and after deposit of the cream inside. After Aldara™ cream application on ear skin, the weight of eppendorf tubes is re-evaluated to calculate approximately the quantity of cream rubbed into the skin. For each tube, all the cream content is rubbed for at least 15 seconds and until complete skin penetration.

Poly-ICLC (TLR3 agonist) was provided by Oncovir (Inc, WA, US) in vials containing 1 mL of 2 mg/mL opalescent sterile solution. The Poly-ICLC is left in the original recipient and stored at +4° C. Poly-ICLC for injection contains 2 mg/mL of poly-IC stabilized with 1.5 mg/mL poly-L-Lysine and 5 mg/mL sodium carboxymethylcellulose in 0.9% sodium chloride solution and adjusted to pH 7.6-7.8 with sodium hydroxide.

Tumour Measurement

Different parameters are taken into account to evaluate tumour development in mice:

Tumour size: Tumours are measured manually using a calliper twice a week starting 5 days post-tumour cells inoculation and until day 60. Tumour volume is then calculated as follow: volume=(Length×width$^2$)/2;

Mice survival: for ethical reasons mouse developing abnormally important (limit size: 2000 mm$^3$) and/or necrotic tumours, or with tumour-induced impaired mobility are euthanized; and Number of tumour-free mice: This information indicates when therapeutic vaccination has induced a full tumour regression (absence of palpable tumour).

Measurement of CD8 T Cell Memory Cytototoxic Responses

The method for measuring cytotoxicity of CD8$^+$ T cells in vivo has been extensively described (Barchet, Oehen et al. 2000; Ingulli 2007). Briefly, syngeneic splenocytes from naive mice are labeled with different concentrations of CFSE (Carboxyfluorescein succinimidyl ester, Molecular Probes Invitrogen) and either pulsed in vitro with relevant H-2$^b$ restricted peptides or let unpulsed. Both peptide-pulsed and unpulsed target cells populations are adoptively transferred intravenously into syngeneic vaccinated hosts and the loss of peptide-pulsed targets is measured by flow cytometry (BD FACSCalibur) into the spleen. The percentage of killing is estimated from the reduction in the ratio of the percentage of pulsed target cells to unpulsed cells, corrected by the initial ratio (see below). Cellular preparations are analyzed by flow cytometry before injection to check-CFSE loading of the different target cells and get reference values (real percentage of each cellular population) for the calculation of the in vivo killing. The three target cells populations are then injected intravenously at a 1:1:1 ratio to each vaccinated mice. The percentage of in vivo killing is calculated as described elsewhere with the following formula (Barber, Wherry et al. 2003)

PERCENT KILLING=100−([(% peptide pulsed in vaccinated/% unpulsed in vaccinated)/(% peptide pulsed before injection/% unpulsed before injection))×100)

IFN-γ ELISpot (Enzyme-Linked-Immunospot) Assay

Frequencies of HPV16 E7$_{49-57}$ and HPV18 E7$_{AS43-49}$ IFN-γ producing specific CD8$^+$ T cells are evaluated on ex-vivo restimulated splenocytes by an IFN-γ ELISpot assay:

ELISpot are performed on individual mice, not on pooled spleen.

Mice have received the day before intravenous infusion of syngeneic CFSE-loaded target splenocytes (due to the in vivo killing assay, see above).

Briefly, total splenocytes obtained from vaccinated mice are let unstimulated or restimulated for 20 h at 37° C., 5% CO2 with 1 μg/ml of each peptide as described below:

1×10$^6$ cells/well with the HPV16 E7$_{49-57}$ peptide (H-2$^b$ restricted relevant epitope)

1×10$^6$ cells/well with OVA$_{257-264}$ (H-2$^b$ restricted irrelevant epitope).

0.25×10$^6$ cells/well with HPV18E7$_{AS43-49}$ (H-2$^b$ restricted relevant epitope).

IFN-γ secretion is monitored by a sandwich based ELISpot revealed by BCIP/NBT using streptavidin-AKP. Data were analyzed on a Bioreader 5000-Pro S (Biosys).

Therapeutic/Prophylactic Vaccinations

Figure 8:
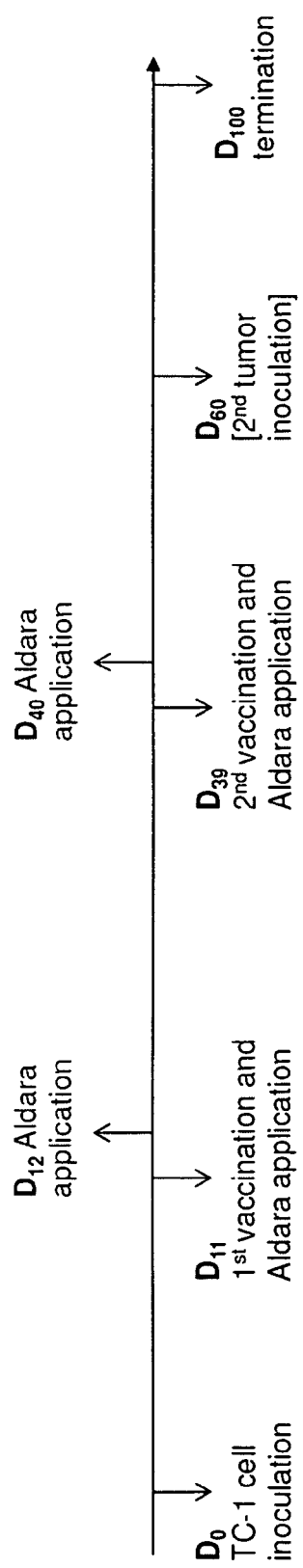
FIG. 8. General scheme of vaccination (D means day); the table summarized the nature and the site of the cell inoculations and vaccinations (/: no inoculation).

The therapeutic scheme, detailed below, is summarized in FIG. 8.

At day 0, two groups of mice (groups 1 and 2) were inoculated on the right flank with TC-1 cells (1×10$^6$ cells per mouse). Then, mice received two vaccinations, the first one at day 11 and the second one at day 39, with Placebo (PBS 1×+urea) (group 1) or with Placebo+Aldara™ (group 2). Groups 1 and 2 are negative control.

Figure 9:
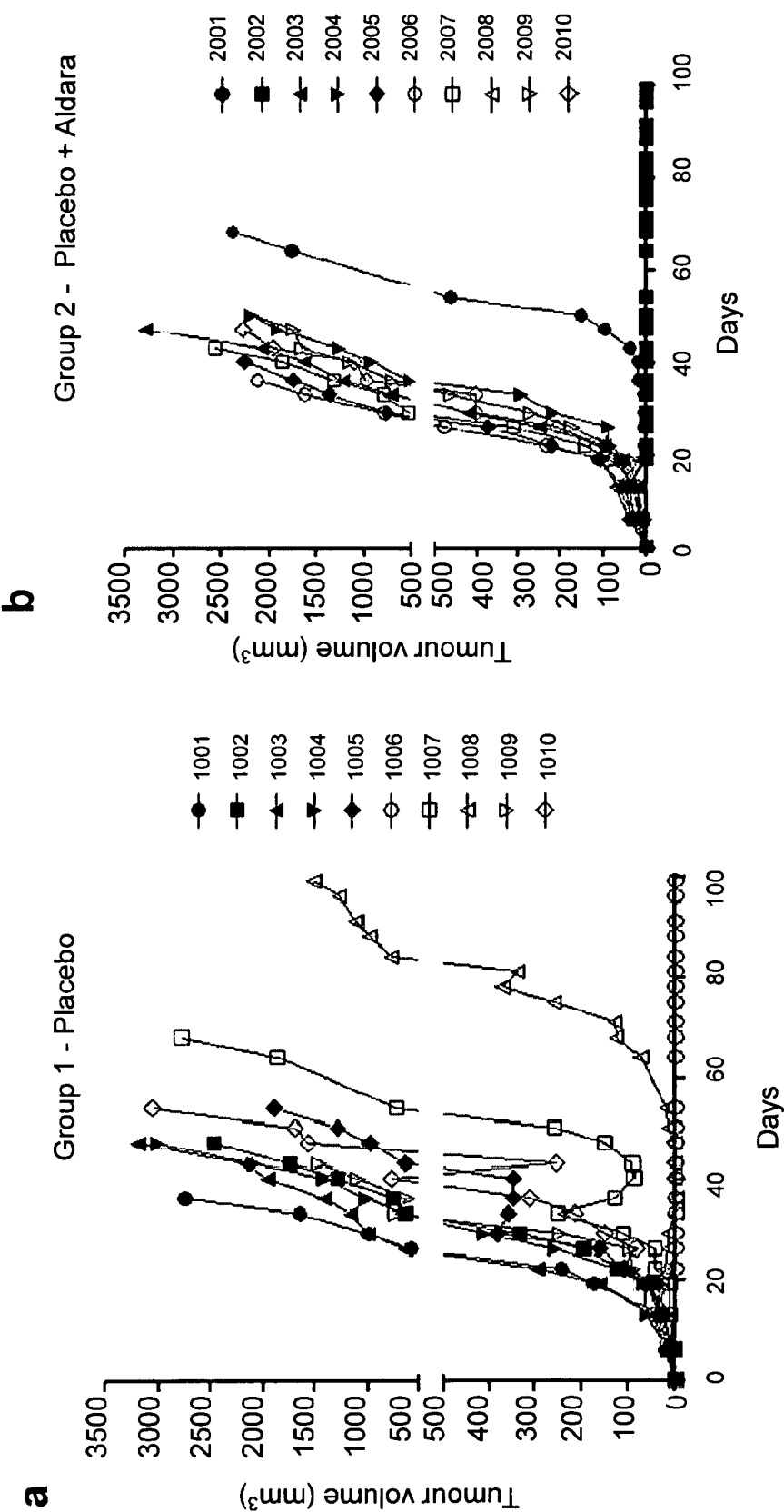
FIG. 9a. Therapeutic vaccination by Aldara™-adjuvanted CyaA-bivalent vaccines embedding the HPV16 E7 antigen lead to TC-1 induced solid tumour clearance. The volume of tumoral TC1 cells (mm$^3$) was followed up from day 0 (D$_0$) until day 100 (D$_{100}$), in the right flank of 10 mice by group. Mice of group 1 were vaccinated with placebo. The number on the right of the graph corresponds to the number assigned to each mouse of the group.
FIG. 9b. Therapeutic vaccination by Aldara™-adjuvanted CyaA-bivalent vaccines embedding the HPV16 E7 antigen lead to TC-1 induced solid tumour clearance. The volume of tumoral TC1 cells (mm$^3$) was followed up from day 0 (D$_0$) until day 100 (D$_{100}$), in the right flank of 10 mice by group. Mice of group 2 were vaccinated with Placebo+Aldara™. The number on the right of the graph corresponds to the number assigned to each mouse of the group.
FIG. 9c. Therapeutic vaccination by Aldara™-adjuvanted CyaA-bivalent vaccines embedding the HPV16 E7 antigen lead to TC-1 induced solid tumour clearance. The volume of tumoral TC1 cells (mm$^3$) was followed up from day 0 (D$_0$) until day 100 (D$_{100}$), in the right flank of 10 mice by group. Mice of group 3 were vaccinated with Aldara™-adjuvanted CyaA-MAGEA3$_{97-178/190-295}$/CyaA-HPV16 E7. The number on the right of the graph corresponds to the number assigned to each mouse of the group.
FIG. 9d. Therapeutic vaccination by Aldara™-adjuvanted CyaA-bivalent vaccines embedding the HPV16 E7 antigen lead to TC-1 induced solid tumour clearance. The volume of tumoral TC1 cells (mm$^3$) was followed up from day 0 (D$_0$) until day 100 (D$_{100}$), in the right flank of 10 mice by group. Mice of group 4 were vaccinated with Aldara™-adjuvanted CyaA-cysOVA/CyaA-HPV16 E7. The number on the right of the graph corresponds to the number assigned to each mouse of the group.
FIG. 9e. Therapeutic vaccination by Aldara™-adjuvanted CyaA-bivalent vaccines embedding the HPV16 E7 antigen lead to TC-1 induced solid tumour clearance. The volume of tumoral TC1 cells (mm$^3$) was followed up from day 0 ($D_0$) until day 100 ($D_{100}$), in the right flank of 10 mice by group. Mice of groups 5 were vaccinated with Aldara™-adjuvanted ProCervix. The number on the right of the graph corresponds to the number assigned to each mouse of the group.
FIG. 9f. Therapeutic vaccination by Aldara™-adjuvanted CyaA-bivalent vaccines embedding the HPV16 E7 antigen lead to TC-1 induced solid tumour clearance. The volume of tumoral TC1 cells (mm$^3$) was followed up from day 0 ($D_0$) until day 100 ($D_{100}$), in the right flank of 10 mice by group. Mice of group 6 were vaccinated with Aldara™-adjuvanted ProCervix. The number on the right of the graph corresponds to the number assigned to each mouse of the group.
Figure 9:
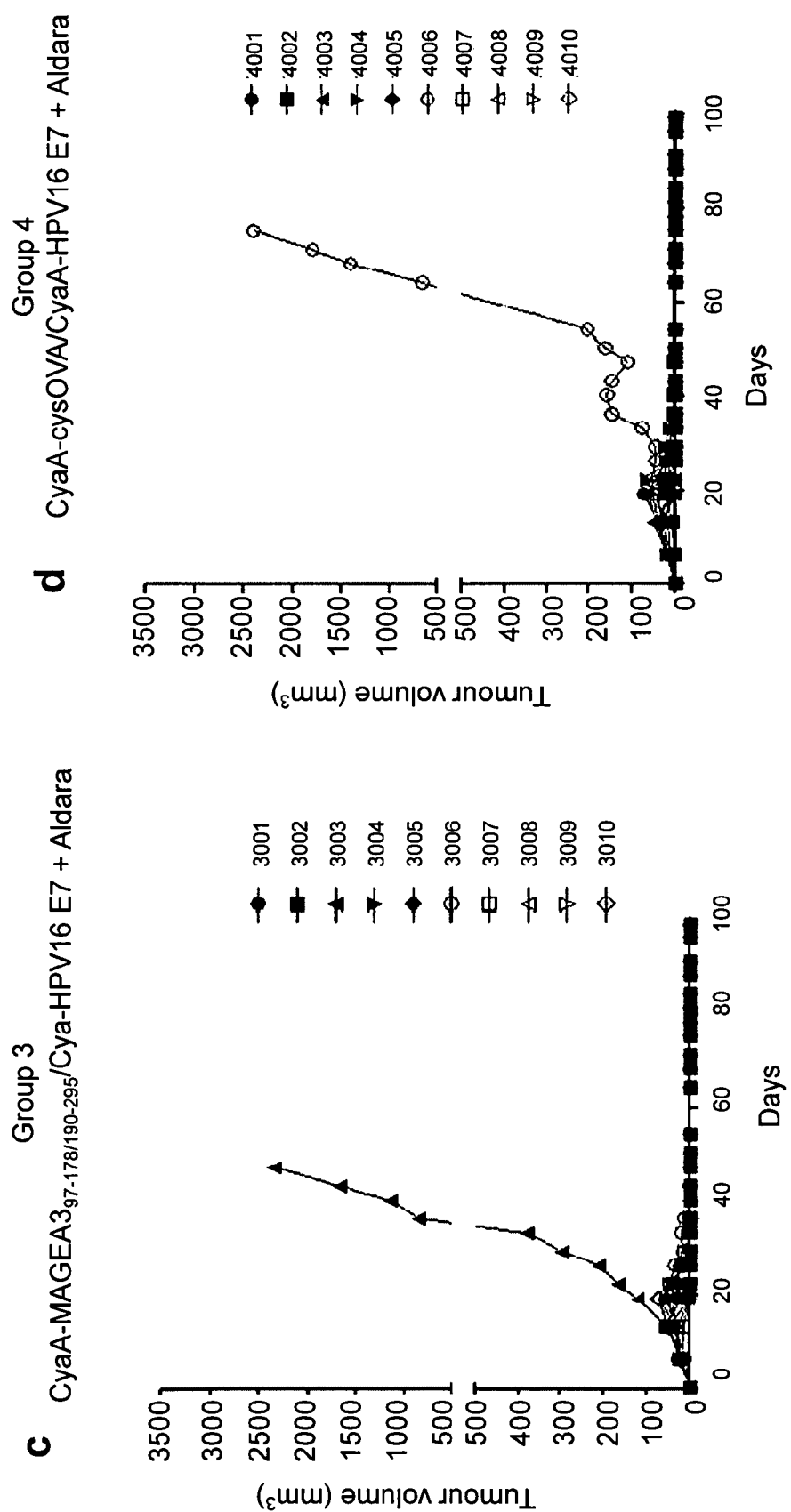
Figure 9:
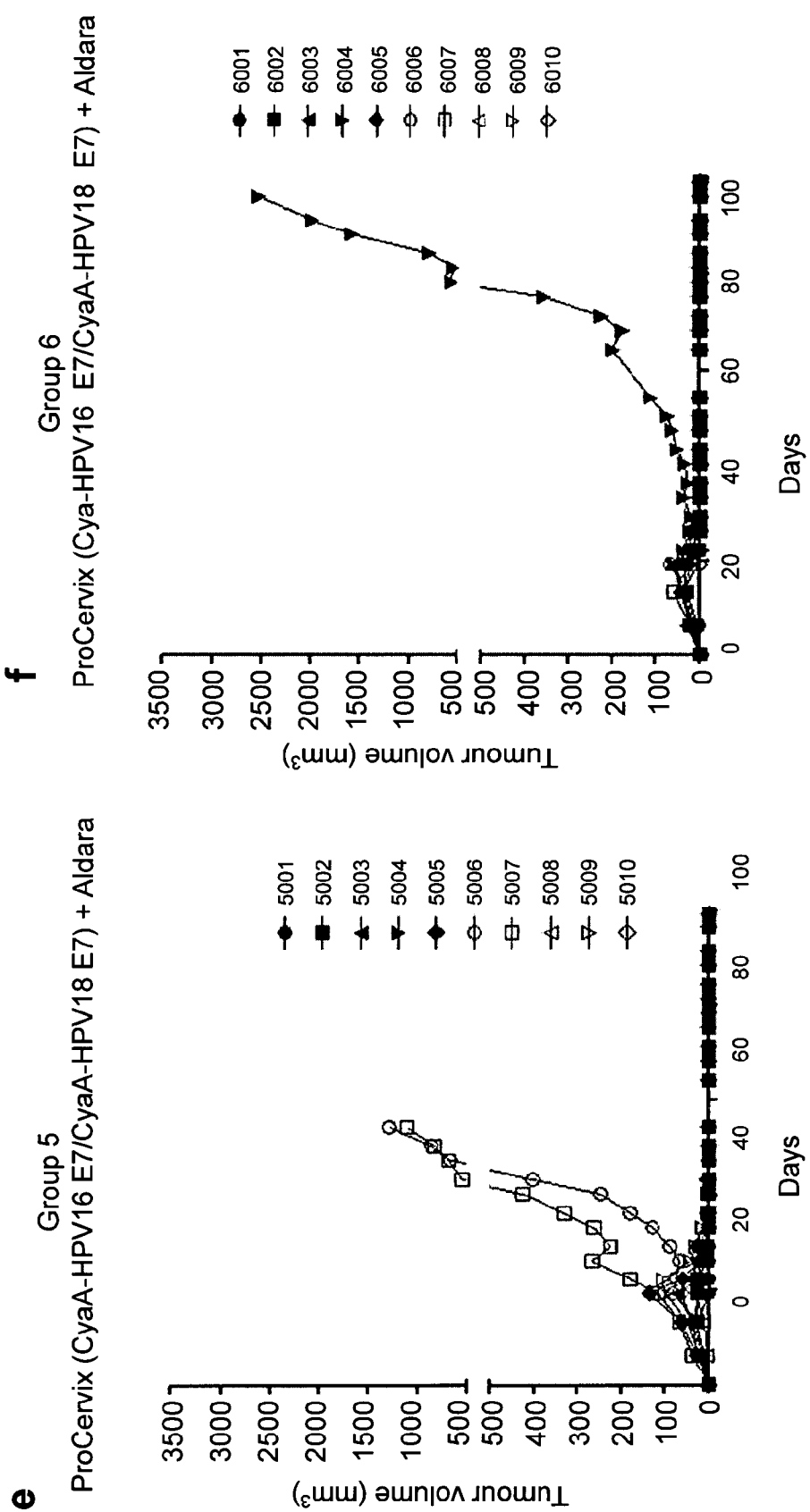

At day 0, four groups of mice (groups 3 to 6) were inoculated on the right flank, with TC-1 cells (1×10$^6$ cells per mouse) (groups 3 to 6); then, mice received two vaccinations, the first one at day 11 and the second one at day 39, with CyaA-MAGEA3$_{97-178/193-295}$/CyaA-HPV16 E7 (5 μg of each CyaA-based vector) in presence of Aldara™ (group 3), with CyaA-cysOVA/CyaA-HPV16 E7 (5 μg of each CyaA-based vector) in presence of Aldara™ (group 4) or with Aldara™-adjuvanted ProCervix (groups 5 and 6, as positive control for TC-1 tumour elimination). The right flank of these mice was monitored until day 100 (FIG. 9). At day 60, survival mice were inoculated with a second tumor cell line, either B16-tumour cells expressing the MAGE A3 protein (groups 3 and 5) or EG7 tumour cells (malignant syngeneic cells expressing the ovalbumin protein) (groups 4 and 6). The left flank of these mice was monitored until day 100.

When it is used, Aldara™ is applied topically (cutaneously), at the site of vaccination, the day of vaccination and the day following the vaccination (i.e., at days 12 and 40).

B. Results

Figure 5:
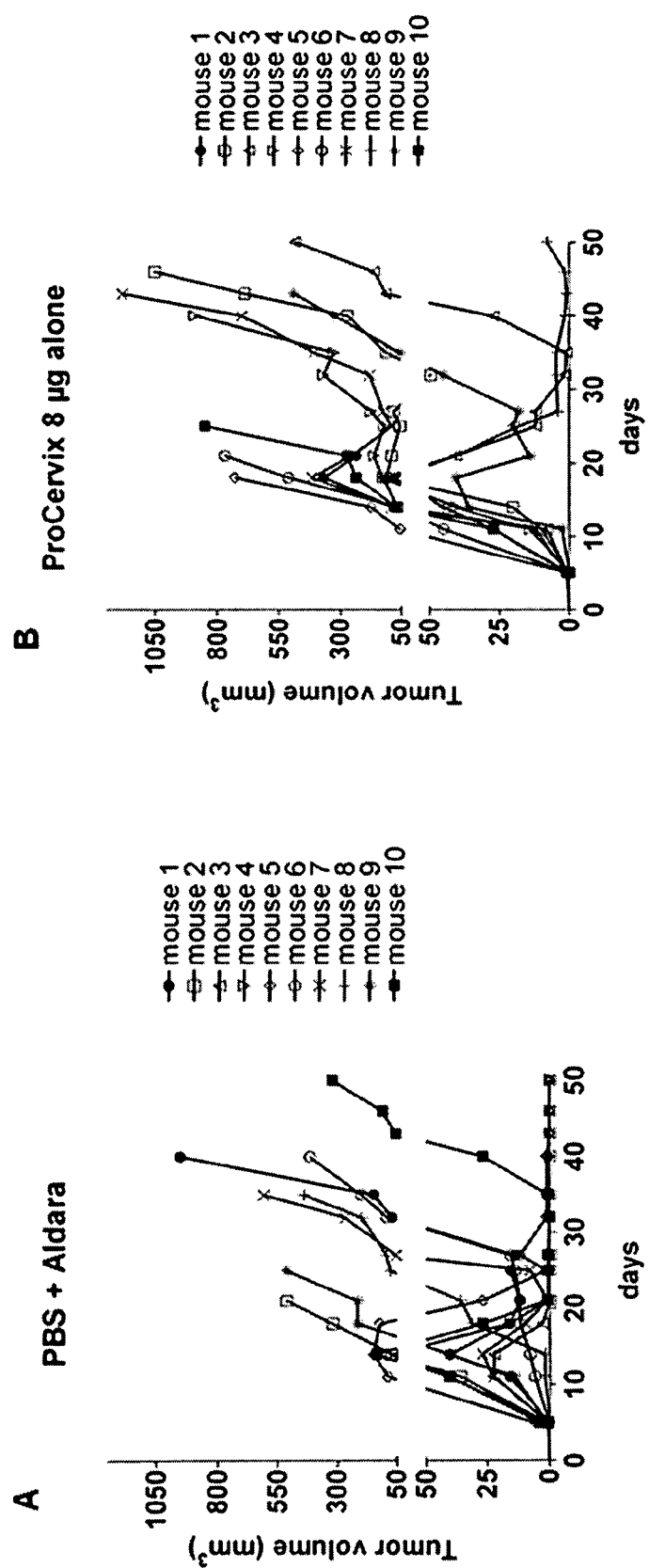
FIG. 5A. Therapeutic vaccination by adjuvanted ProCervix at day 11 eradicates established solid TC-1-induced tumours. At the end of the monitoring: the group of mice vaccinated with PBS+Aldara™ display 3/10 mice under tumour regression.
FIG. 5B. Therapeutic vaccination by ProCervix. The group of mice vaccinated with ProCervix 8 µg alone display 0/10 mice under tumour regression.
FIG. 5C. Mice vaccinated with ProCervix adjuvanted with Aldara™ (topical Imiquimod) display 7/10 mice under tumour regression.
FIG. 5D. Mice vaccinated with either ProCervix adjuvanted with Poly-ICLC display 7/10 mice under tumour regression.
Figure 5:
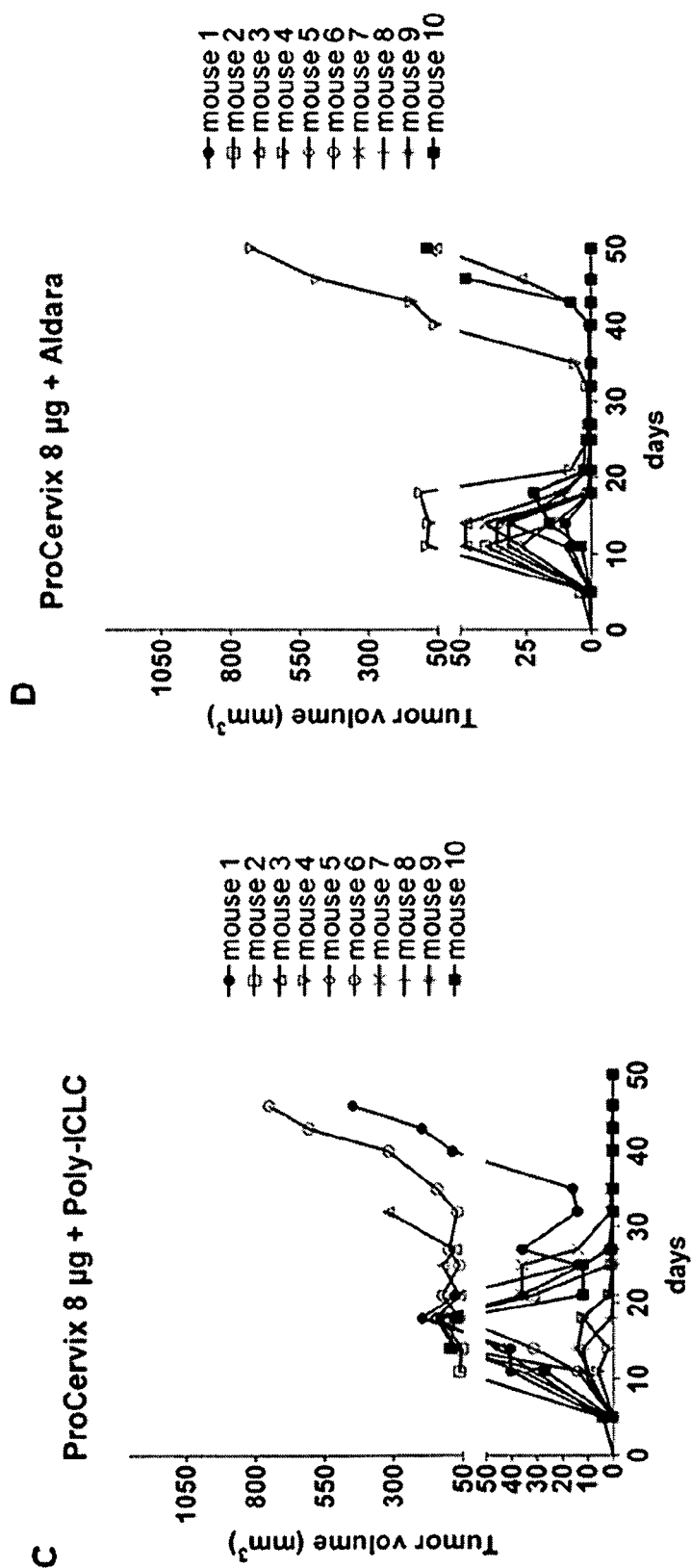

Mice Bearing HPV16 E7-Expressing Solid Tumours Vaccinated by ProCervix Display High Tumour Regression Rate and Improved Survival Mice vaccinated at day 11 with PBS and which received Aldara™ application did not display inhibition of tumour growth with the exception of 2 mice out of 10 that fully eliminated the tumor before day 50 (FIGS. 5A and 6A). Four mice were alive in this group at day 50 (FIG. 6B; end of the tumour size monitoring). No PBS-only treated group was included in this study and it is thus difficult to have a clear idea of the impact of Aldara™ as compared to natural response of mice against tumour. However, it is obvious that the effect observed with Aldara™ alone is far weaker than those observed with Aldara™-adjuvanted ProCervix (see thereafter). This indicates that even if Aldara™ may have some bystander effect on tumour progression, probably due to innate immune activation and resulting inflammatory processes (pro-inflammatory cytokines, etc. (Schon and Schon 2008)), it is not potent enough to be used alone with this therapeutic scheme as a treatment of solid HPV-induced tumours.

Figure 6:
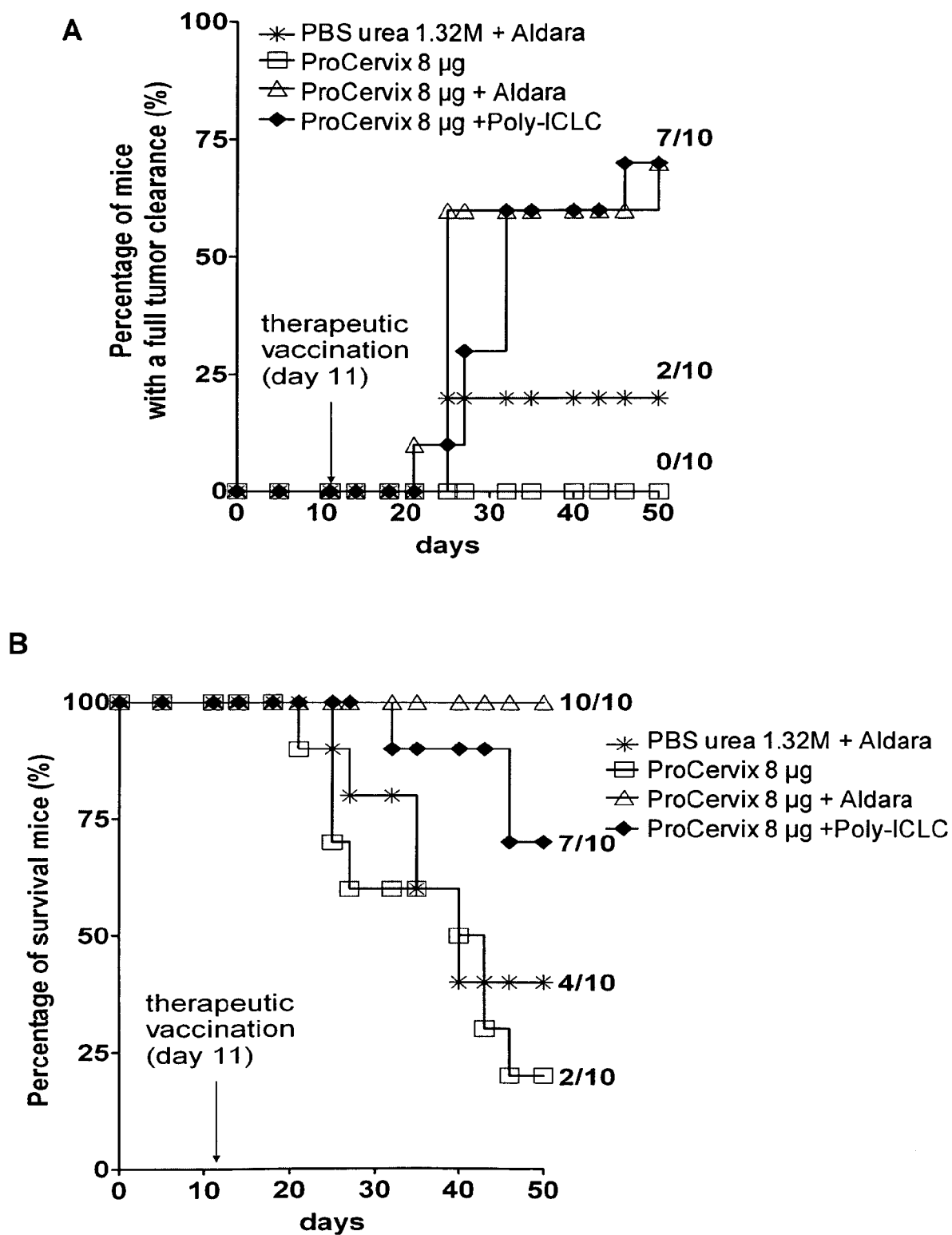
FIG. 6A. Therapeutic vaccination by adjuvanted ProCervix induces both high survival rate and high percentage of tumour free mice at day 50. At day 50, mice vaccinated either by ProCervix+Aldara™ or ProCervix+Poly-ICLC do not display tumour.
FIG. 6B. Survival rate of mice vaccinated according to FIG. 6A, at day 50: 100% and 70% of mice that have received at day 11 respectively ProCervix+Aldara™ and ProCervix+Poly-ICLC are alive (B).

Mice vaccinated at day 11 with unadjuvanted ProCervix also displayed important tumour outgrowth without tumour-free mice at day 50 (FIGS. 5B and 6A). Only two mice were alive at day 50 in this group (FIG. 6B). Therapeutic vaccination with ProCervix adjuvanted by topical Imiquimod (Aldara™) induced a significant tumour regression (FIG. 5D) leading to high survival rates (FIG. 6B) and a majority of tumour free mice at the end of the study (FIG. 6A). For Aldara™-adjuvanted ProCervix group we observed a tumour escape after a period of apparent control (size decreased to less than 50 mm$^3$) in 3 mice out of 10. The escape occurred between day 30 and day 40 with an important growth until day 50. This phenomenon could be due to escape mechanisms developed by tumours and should in this case be taken into account for therapeutic scheme refinements but it is more probably due to the loss of MHC-class I molecules at the surface of tumour cells as previously described for TC-1 cells (Zwaveling, Ferreira Mota et al. 2002). Therapeutic vaccination with Poly-ICLC-adjuvanted ProCervix gave comparable results of tumour regression and survival rate (FIGS. 5C and 6). These results show that therapeutic vaccination of mice bearing HPV16 E7-expressing solid tumours with ProCervix either adjuvanted by Poly-ICLC or topical Imiquimod (Aldara™) results in a strong therapeutic effect.

ProCervix Therapeutic Vaccination Promotes the Development of Both HPV16 E7 and HVP18 E7 Specific Functional Memory CTL It was described by Rafi Ahmed and colleagues in a murine model of acute viral infection with LCMV that memory CD8+ T cells are able to exhibit rapid lytic potential in vivo (Barber, Wherry et al. 2003). Based on these observations, we decided to investigate if mice that have fully cleared the TC-1-induced solid tumours, following administration of ProCervix at day 11, display functional antigen-specific memory CD8$^+$ T cells after eradication of the tumour.

Figure 7:
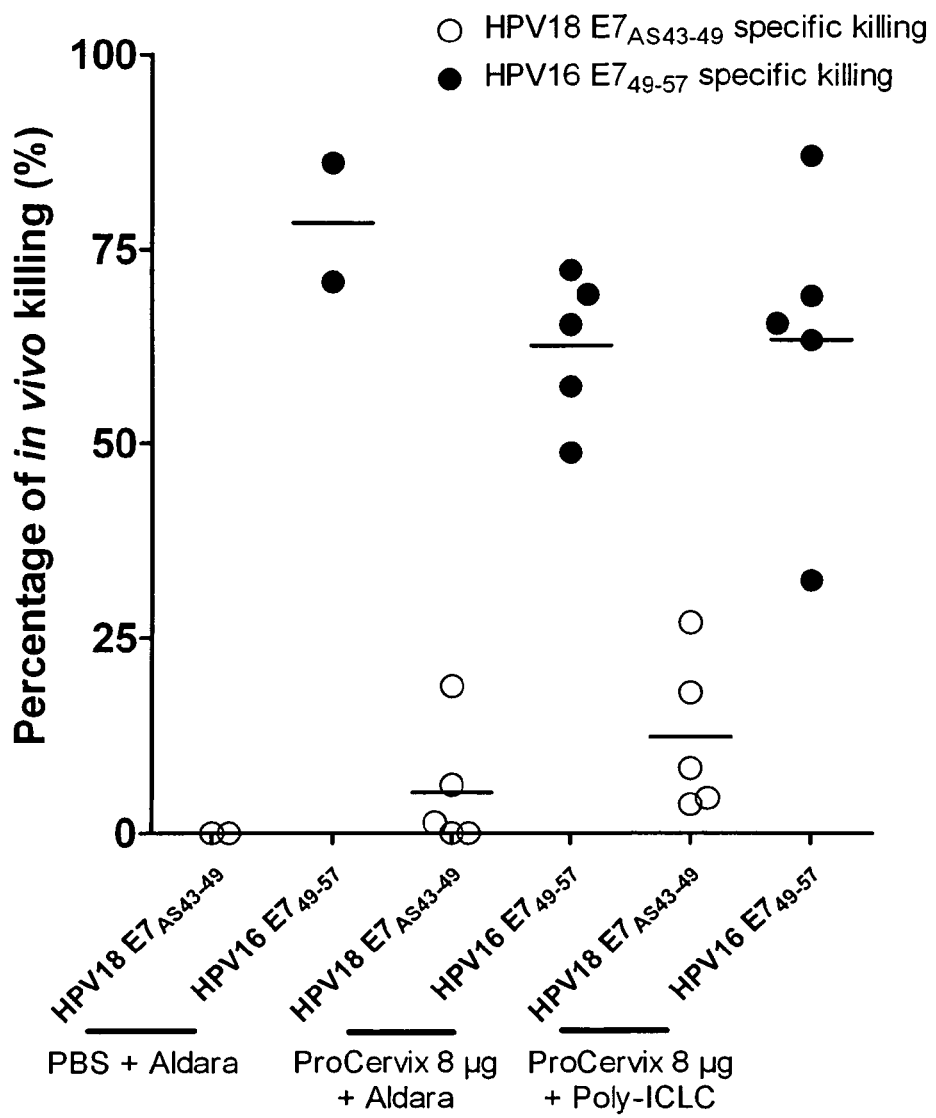
FIG. 7. Sixty days post-therapeutic vaccination by adjuvanted ProCervix tumour-free mice exhibit functional HPV16 E7$_{49-57}$ and HPV18 E7$_{AS43-49}$ specific memory CD8$^+$ T cells. At day 60 tumour free mice in the different groups were iv injected with CFSE$^{hi}$ HPV16$_{E749-57}$ pulsed target cells, CFSE$^{im}$ unpulsed target cells and CFSE$^{lo}$ HPV18E7$_{AS43-49}$ pulsed target cells at a 1:1:1 ratio. After overnight, mice were euthanatized, spleen collected and antigen-specific in vivo cytotoxicity was measured by FACS analysis. Each dot represents results obtained from an individual mouse; open circles represent the percentage of killing of HPV18 E7$_{AS43-49}$ pulsed target cells and black circles represent the percentage of killing of HPV16 E7$_{49-57}$ pulsed target cells. Bars represent the mean value for a group of mice.

To this end, at day 60 post-TC-1 cells inoculation, remaining tumour free mice in each group were adoptively transferred with CFSE-loaded syngeneic splenocytes in order to measure in parallel the in vivo cytotoxicity (as described above in the Material and Methods section) of memory CD8$^+$ T cells against the two following H-2$^b$ restricted epitopes: HPV16 E7$_{49-57}$ and HPV18 E7$_{AS43-49}$. In the groups of mice vaccinated by ProCervix either adjuvanted by Aldara™ or adjuvanted by Poly-ICLC, 5 tumour-free mice were taken (randomly selected in the group) to perform the in vivo killing assay. In all tested mice, which have all fully eradicated the tumour, we detected strong cytotoxicity against HPV16 E7$_{49-57}$-pulsed target cells (FIG. 7). No differences can be observed between groups. The detection of HPV16E7-specific cytotoxic response in placebo with Aldara™ vaccinated group is due to the use for this test of the two tumour-free mice (all the others mice were dead due to the tumour outgrowth at day 60). This data indicates that these two mice have been able to develop an HPV16 E7 specific immune response strong enough to clear the TC-1 induced solid tumours. Interestingly only mice vaccinated with adjuvanted ProCervix also displayed HPV18E7-pulsed target cell. These data are more informative as TC-1 cells do not express HPV18 antigens, thus indicating that the HPV18-specific cytotoxicity reported was only due to vaccine-induced memory T cells. In fact, no in vivo cytotoxicity against HPV18E7-pulsed target cells was observed in Aldara™ only treated mice (FIG. 7).

Taken together, our data demonstrate the exquisite efficiency of ProCervix at inducing, with only one injection, functional CD8-dependent memory response against both HPV16 E7 and HPV18 E7 antigens. A one shot ProCervix vaccination is able to induce the differentiation of a pool of antigen-specific memory CD8$^+$ T lymphocytes that confer to vaccinated mice, both a long term protection against a secondary challenge with syngeneic grafted cells expressing HPV16 E7 (antigen expressed by tumours) and in parallel a protection against a new challenge with HPV18 E7 expressing syngeneic grafted cells (antigen which is not expressed by tumours and which is only delivered by the CyaA-HPV18E7$_{\Delta 32\text{-}42}$ vector).

Bivalent CyaA-HPV16E7$_{\Delta 30\text{-}42}$/CyaA-MAGE A3 Therapeutic Vaccination Provides Eradication of HPV16 E7-Expressing Solid Tumours and Protection Against the Development of MAGE-A3 Induced-Tumours Mice vaccinated with CyaA-HPV16E7$_{\Delta 30\text{-}42}$/CyaA-MAGE A3+Aldara as transcutaneous adjuvant (group 3) and mice vaccinated with Aldara-adjuvanted ProCervix (groups 5 and 6) cleared TC1-induced solid tumours within 40 days: 9 out of 10 mice in group 3 (FIG. 9c); 8 out of 10 mice in group 5, and 9 out of 10 in group 6 (FIGS. 9 e and f). The strong clearance of tumors was confirmed until day 100. In contrast, mice that were vaccinated with the Placebo, with or without adjuvant (group 1 and 2 respectively), as negative controls developed TC1-induced solid tumours: 9/10 mice in group 1 (FIG. 9a) and 8/10 mice in group 2 (FIG. 9b).

Figure 10:
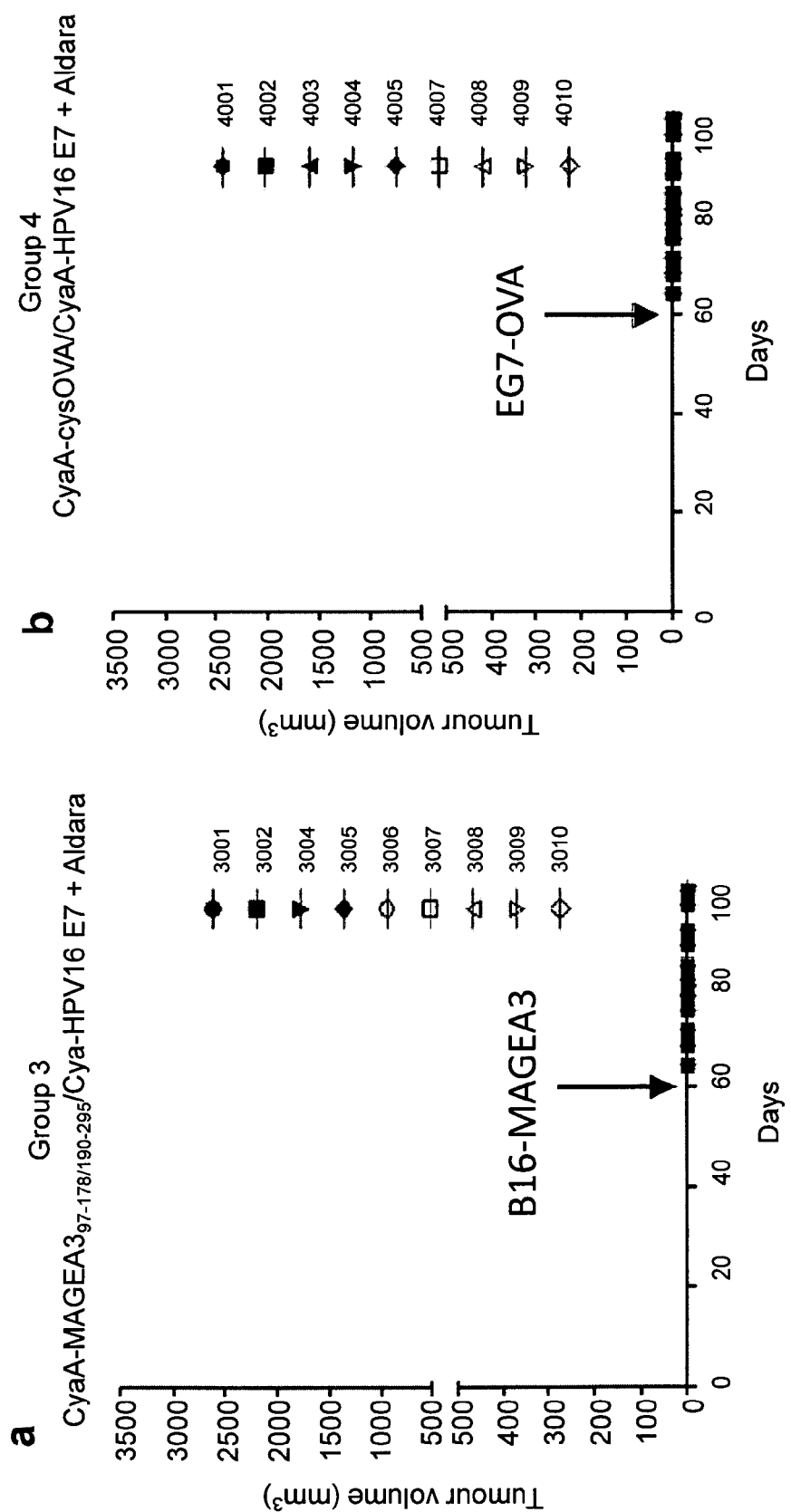
FIG. 10a. Mice that have been cured for a TC1 induced tumour with CyaA-based bivalent vaccination are protected against another unrelated tumour challenge in an antigen-specific fashion. The volume of tumoral B16 MAGE A3 cells was followed up from day 60 ($D_{60}$) until day 100 ($D_{100}$), in the left flank of the mice which have survived, at day 60, the TC1 challenge. The number on the right of the graph corresponds to the number previously assigned to each mouse in the TC1 challenge (FIG. 9).
FIG. 10b. Mice that have been cured for a TC1 induced tumour with CyaA-based bivalent vaccination are protected against another unrelated tumour challenge in an antigen-specific fashion. The volume of tumoral EG7-OVA cells was followed up from day 60 ($D_{60}$) until day 100 ($D_{100}$), in the left flank of the mice which have survived, at day 60, the TC1 challenge. The number on the right of the graph corresponds to the number previously assigned to each mouse in the TC1 challenge (FIG. 9).
FIG. 10c. Mice that have been cured for a TC1 induced tumour with CyaA-based bivalent vaccination are protected against another unrelated tumour challenge in an antigen-specific fashion. The volume of tumoral B16 MAGE A3 cells was followed up from day 60 ($D_0$) until day 100 ($D_{100}$), in the left flank of the mice which have survived, at day 60, the TC1 challenge. The number on the right of the graph corresponds to the number previously assigned to each mouse in the TC1 challenge (FIG. 9).
FIG. 10d. Mice that have been cured for a TC1 induced tumour with CyaA-based bivalent vaccination are protected against another unrelated tumour challenge in an antigen-specific fashion. The volume of tumoral EG7-OVA cells was followed up from day 60 ($D_{60}$) until day 100 ($D_{100}$), in the left flank of the mice which have survived, at day 60, the TC1 challenge. The number on the right of the graph corresponds to the number previously assigned to each mouse in the TC1 challenge (FIG. 9).
Figure 10:
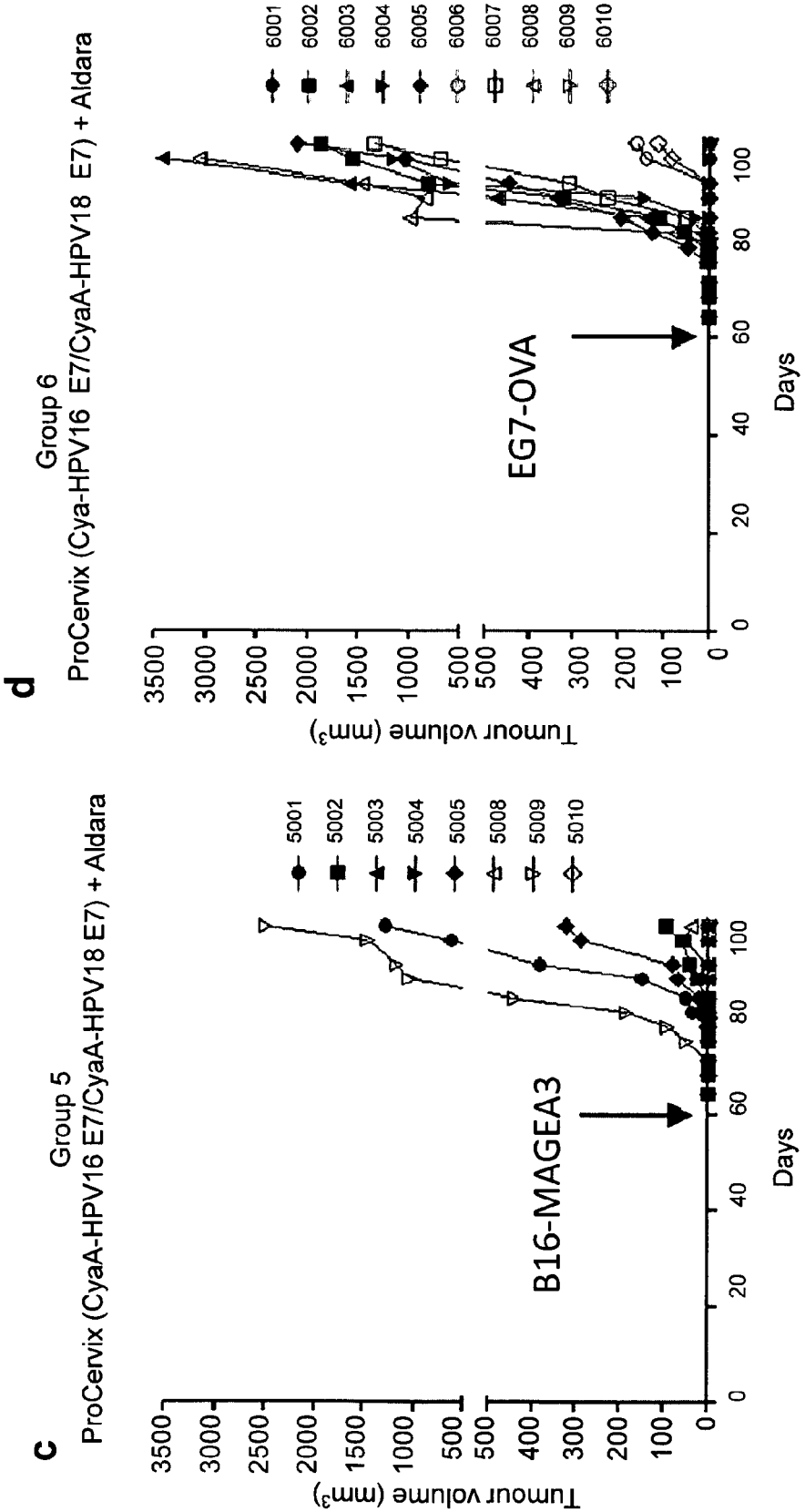

At day 60, survival mice from groups 3 and 5 were inoculated, in their left flank, with B16-tumour cells expressing the MAGE A3 protein. None of the mice, that were vaccinated with CyaA-HPV16E7$_{\Delta 30\text{-}42}$/CyaA-MAGE A3 in the presence of Aldara™ and that have cleared TC1-induced tumours, showed B16-MAGEA3 tumour development after challenge (0 out of 9 mice developed B16-MAGEA3 tumours; FIG. 10a), indicating that these mice were protected against the challenge with B16-MAGE A3-induced solid tumours.

In contrast, mice vaccinated with Aldara™-adjuvanted ProCervix and that have cleared TC1-induced tumours develop B16-MAGEA3 tumours (6 out of 8 mice developed B16-MAGEA3 tumours; FIG. 10c), indicating that Procervix (HPV16E7/HPV18E7) did not confer protective memory T-cell immunity against the challenge by B16-MAGEA3 tumour cells. Thus, the protection against the development of MAGE A3-induced tumours observed in group 3 mice was achieved as a result of the induction of a MAGE A3-specific T-cell mediated memory response in mice vaccinated with CyaA-MAGEA3, whereas the T-cell mediated memory response elicited in group 5 mice was raised against an antigen (HPV18 E7) which is irrelevant regarding the nature of the B16-MAGEA3 tumour cells.

In conclusion, these experiments demonstrate that bivalent CyaA may be used, following one administration, both to eradicate TC-1 cells (HPV18E7-specific immune response), and to prevent the development of B16-MAGEA3 tumor cells (MAGE A3-specific T cell mediated memory response). Moreover, results obtained after day 60 showed that the prophylactic effect obtained against the B16-MAGEA3 tumor cells did not impair the therapeutic effect obtained against TC-1 cells (eradication of TC1 cells until day 100; FIG. 9c).

Bivalent CyaA-HPV16E7$_{\Delta 30\text{-}42}$/CyaA-cysOVA Therapeutic Vaccination Provides Eradication of HPV16 E7-Expressing Solid Tumours and Protection Against the Development of EG7-OVA Induced-Tumours Mice vaccinated with CyaA-HPV16E7$_{\Delta 30\text{-}42}$/CyaA-CysOVA in presence of Aldara™ as transcutaneous adjuvant (group 4) and mice vaccinated with Aldara-adjuvanted ProCervix (group 5 and 6) cleared TC1-induced solid tumours within 40 days: 9 out of 10 mice in group 4 (FIG. 9d) and 8 out of 10 mice in group 5 and 9 out of 10 in group 6 (FIGS. 9 e and f). The strong clearance of tumors was confirmed until day 100. In contrast, mice that were vaccinated with the Placebo with or without adjuvant (group 1 and 2 respectively), as negative controls, developed TC1-induced solid tumours: 9/10 mice in group 1 (FIG. 9a) and 8/10 mice in group 2 (FIG. 9b).

At day 60, survival mice from groups 4 and 6 were inoculated, in their left flank, with EG7-OVA tumour cells (malignant syngeneic cells expressing the ovalbumin protein). In group 6, mouse 6004 developed a tumor after day 60

(FIG. 9f), such that it was inoculated with EG7-OVA tumour cells like the 9 other mice of the group which did not develop tumors. None of the mice, that were vaccinated with CyaA-HPV16E7$_{\Delta 30\text{-}42}$/CyaA-CysOVA in presence of Aldara™ and that have cleared TC1-induced tumours, showed EG7-OVA tumour development after the challenge (0 out of 9 mice developed EG7-OVA tumours; FIG. 10b), demonstrating that these mice were protected against the challenge with EG7-OVA tumour cells. In contrast, mice that were vaccinated with Aldara™-adjuvanted ProCervix and that have cleared TC1-induced tumours developed EG7-OVA tumours (8 out of 10 mice developed EG7-OVA tumours; FIG. 10d), indicating that Procervix (HPV16E7/HPV18E7) did not confer protective memory T-cell immunity against the challenge by EG7-OVA tumour cells. Thus, the protection against the development of EG7-OVA-induced solid tumours observed in group 4 was achieved as a result of the induction of an OVA-specific T-cell mediated memory response in mice vaccinated with CyaA-HPV16E7$_{\Delta 30\text{-}42}$/CyaA-CysOVA, whereas the T-cell mediated memory response elicited in group 6 mice was raised against an antigen (HPV18 E7) which is irrelevant regarding the nature of the EG7-OVA tumours.

In conclusion, these experiments demonstrate that bivalent CyaA may be used, following one administration, both to eradicate TC-1 cells (HPV18E7-specific immune response), and to prevent the development of EG7-OVA-induced solid tumours. Moreover, results obtained after day 60 showed that the prophylactic effect obtained against the EG7-OVA tumor cells did not impair the therapeutic effect obtained against TC-1 cells (eradication of TC1 cells until day 100; FIG. 9d).

C. Conclusion

The novel concept brought in the present application, with the bivalent ProCervix therapeutic vaccination is, in one hand, to treat for example HPV16 infected patients, eradicate the infection and, in the other hand, to provide T-cell mediated memory responses for both HPV16 E7 and HPV18 E7 antigens, thus establishing for the ProCervix-vaccinated patients a long term protection against possible re-infection with HPV16 and also against later infection with HPV18. This was confirmed with two other bivalent vaccinations (CyaA-HPV16E7$_{\alpha A\text{-}42}$/CyaA-MAGE A3 and CyaA-HPV16E7$_{\Delta 30\text{-}42}$/CyaA-CysOVA) that have been shown, in the one hand, to treat HPV16 infected mice (eradiction of TC1 cells), and in the other hand, to provide protection against the development of B16-MAGE A3 tumors or EG7-OVA tumors respectively.

Using a preclinical murine model of cervical carcinoma [TC-1 tumour cells (Lin, Guarnieri et al. 1996; Zwaveling, Ferreira Mota et al. 2002)], it was shown that therapeutic vaccination of mice bearing solid HPV16 E7-expressing tumours with ProCervix combined to an adjuvant molecule [TLR agonists as Aldara™ (Johnston and Bystryn 2006; Heib, Becker et al. 2007; Schon and Schon 2008) or Poly-ICLC (Longhi, Trumpfheller et al. 2009)] leads to an efficient tumour regression.

Moreover, it was shown that vaccine-induced tumour clearance can be correlated with the presence of long lasting HPV16 E7-specific CTL memory responses in mice that have fully eradicated the tumour. Unexpectedly, it was also put in evidence that in these tumour-free mice, ProCervix therapeutic vaccination generates, in parallel, functional HPV18 E7-specific CTL memory responses. Both HPV16 E7 and HPV18 E7 memory CTL displayed a lytic potential in vivo.

The observations that CyaA-carried polypeptide(s) are able to generate a preventive T-cell memory response(s) against a second group of epitopes in a mammalian host (prophylactic immune response) while enabling to generate a immunotherapeutic treatment of first determined pathological condition(s) diagnosed in said mammalian host by eliciting a T cell immune response against a first group of epitopes, is surprising. Indeed, it is well known that competition exists between different epitopes, either regarding access to APC, processing and presentation by APC and availability of cytokines. This phenomenon leads to a hierarchy of dominant and subdominant epitopes, and enables T-cell immune response to be activated and other T-cell immune response(s) to be suppressed. This phenomenon was expected in the present situation where T cells recognizing the first group of epitopes already exist in the patient before administration of the vector-carried polypeptides (since one or some epitopes of the first group have already been presented to the host immune system), whereas native T cells have to be activated regarding the second group of epitopes. Interestingly, the present invention has shown that, in contrast to what it is expected, the preventive immune response against the second group of epitopes contained in a CyaA-carried polypeptides seems not to be disfavoured with respect to the therapeutic immune response against the first group of epitopes. These results mean that no competition is observed between the immune response induced against the first group of epitopes and the immune response induced against the second group of epitopes. Consequently, the inventors have shown that CyaA-carried polypeptide(s) is/are sufficiently efficient to elicit a T cell immune response within an immunotherapeutic treatment of first determined pathological condition(s) diagnosed in a mammalian host and to elicit a T cell memory immune response within the prophylaxis against second determined pathological condition(s) in the same mammalian host.

BIBLIOGRAPHY

Ahmed, R., M. J. Bevan, et al. (2009). "The precursors of memory: models and controversies." Nat Rev Immunol 9(9): 662-668.

Bachmann, M. F. and G. T. Jennings (2010). "Vaccine delivery: a matter of size, geometry, kinetics and molecular patterns." Nat Rev Immunol 10(11): 787-796.

Barber, D. L., E. J. Wherry, et al. (2003). "Cutting edge: rapid in vivo killing by memory CD8 T cells." J Immunol 171(1): 27-31.

Barchet, W., S. Oehen, et al. (2000). "Direct quantitation of rapid elimination of viral antigen-positive lymphocytes by antiviral CD8(+) T cells in vivo." Eur J Immunol 30(5): 1356-1363.

Frazer, I. H. (2009). "Interaction of human papillomaviruses with the host immune system: a well evolved relationship." Virology 384(2): 410-414.

Goodwin, M. S. and A. A. Weiss (1990). "Adenylate cyclase toxin is critical for colonization and pertussis toxin is critical for lethal infection by Bordetella pertussis in infant mice." Infect Immun 58(10): 3445-3447.

Guermonprez et al. Journal of Experimental Medicine, 193(9), pp 1035-1044, 2001 Heib, V., M. Becker, et al. (2007). "Mast cells are crucial for early inflammation, migration of Langerhans cells, and CTL responses following topical application of TLR7 ligand in mice." Blood 110(3): 946-953.

Ingulli, E. (2007). "Tracing tolerance and immunity in vivo by CFSE-labeling of administered cells." Methods Mol Biol 380: 365-376.

Iwasaki, A. (2010). "Antiviral immune responses in the genital tract: clues for vaccines." Nat Rev Immunol 10(10): 699-711.

Johnston, D. and J. C. Bystryn (2006). "Topical imiquimod is a potent adjuvant to a weakly-immunogenic protein prototype vaccine." Vaccine 24(11): 1958-1965.

Kaech, S. M., S. Hemby, et al. (2002). "Molecular and functional profiling of memory CD8 T cell differentiation." Cell 111(6): 837-851.

Ladant et al. Journal of Biological Chemistry, 267(4): 2244-2250, 1992.

Lin, K. Y., F. G. Guarnieri, et al. (1996). "Treatment of established tumors with a novel vaccine that enhances major histocompatibility class II presentation of tumor antigen."Cancer Res 56(1): 21-26.

Longhi, M. P., C. Trumpfheller, et al. (2009). "Dendritic cells require a systemic type I interferon response to mature and induce CD4+ Th1 immunity with poly IC as adjuvant." J Exp Med 206(7): 1589-1602.

Merad, M., F. Ginhoux, et al. (2008). "Origin, homeostasis and function of Langerhans cells and other langerin-expressing dendritic cells." Nat Rev Immunol 8(12): 935-947.

Preville, X., D. Ladant, et al. (2005). "Eradication of established tumors by vaccination with recombinant Bordetella pertussis adenylate cyclase carrying the human papillomavirus 16 E7 oncoprotein." Cancer Res 65(2): 641-649.

Pulendran, B., S. Li, et al. (2010). "Systems vaccinology." Immunity 33(4): 516-529.

Rosato, A., A. Zoso, et al. (2006). "Predicting tumor outcome following cancer vaccination by monitoring quantitative and qualitative CD8+ T cell parameters." J Immunol 176(3): 1999-2006.

Sallusto, F., A. Lanzavecchia, et al. (2010). "From vaccines to memory and back."Immunity 33(4): 451-463.

Schon, M. P. and M. Schon (2008). "TLR7 and TLR8 as targets in cancer therapy." Oncogene 27(2): 190-199.

Schreiber, T. H., V. V. Deyev, et al. (2009). "Tumor-induced suppression of CTL expansion and subjugation by gp96-Ig vaccination." Cancer Res 69(5): 2026-2033.

Simsova, M., P. Sebo, et al. (2004). "The adenylate cyclase toxin from Bordetella pertussis—a novel promising vehicle for antigen delivery to dendritic cells." Int J Med Microbiol 293(7-8): 571-576.

Stanley, M. (2010). "Potential mechanisms for HPV vaccine-induced long-term protection." *Gynecol Oncol* 118(1 Suppl): S2-7.

Trimble, C. L. and I. H. Frazer (2009). "Development of therapeutic HPV vaccines." *Lancet Oncol* 10(10): 975-980.

Woodland, D. L. and J. E. Kohlmeier (2009). "Migration, maintenance and recall of memory T cells in peripheral tissues." *Nat Rev Immunol* 9(3): 153-161.

Zwaveling, S., S. C. Ferreira Mota, et al. (2002). "Established human papillomavirus type 16-expressing tumors are effectively eradicated following vaccination with long peptides." *J Immunol* 169(1): 350-358.

The invention claimed is:

1. A method of immunotherapeutic treatment of a first pathological condition and prophylaxis of a second pathological condition in a mammalian host, which comprises:
administering to the mammalian host a composition comprising a first group of epitopes and a second group of epitopes,
wherein the groups of epitopes are from the E6 or from the E7 protein of an oncogenic HPV type selected from the group consisting of HPV16, HPV18, HPV31, HPV33, HPV35, HPV45, HPV52 and HPV58,
wherein the first group of epitopes is contained in a polypeptide and the second group of epitopes is contained in the same polypeptide and said polypeptide is carried by one vector or wherein the first group of epitopes is contained in a polypeptide and the second group of epitopes is contained in a different polypeptide and said polypeptides are carried by the same vector or are carried by separate vectors and
wherein the vector(s) is/are a CyaA protein, or a fragment thereof,
wherein said first group of epitopes is not sufficient to obtain prophylaxis against the second pathological condition,
wherein the first group of epitopes leads to the elicitation of a T cell immune response against the first group of epitopes upon administering said composition thereby providing immunotherapeutic treatment against said first pathological condition associated with said first group of epitopes, and wherein, upon administering said composition, the second group of epitopes leads to the elicitation of a T cell memory immune response against the second group of epitopes upon administering said composition thereby providing prophylaxis against said second pathological condition associated with said second group of epitopes.

2. A method of preventing the re-occurrence of a first pathological condition in a mammalian host, which comprises:

eliciting a T cell immune response against a group of epitopes by administering to the mammalian host a vector carrying a polypeptide which comprises the group of epitopes, wherein the vector carrying the group of epitopes is a CyaA protein, or a fragment thereof, and wherein the presence of the group of epitopes within the vector is sufficient to present the epitopes to the immune system in the mammalian host.

3. The method according to claim 1, wherein the polypeptide that comprises the first group of epitopes also comprises the second group of epitopes.

4. The method according to claim 1, wherein said first and second group of epitopes are in different polypeptides.

5. The method according to claim 1, wherein the epitopes are carried by one vector.

6. The method according to claim 1, wherein the first group of epitopes is in a polypeptide carried by a first vector and the second group of epitopes is in a polypeptide carried by a separate vector.

7. The method according to claim 6, wherein said first group of epitopes is in separate polypeptides within said first vector and/or the second group of epitopes is in separate polypeptides within said separate vector.

8. The method according to claim 1, wherein said CyaA is encoded by a *Bordetella* species genome selected from the group consisting of: *Bordetella pertussis, Bordetella parapertussis* and *Bordetella bronchiseptica*.

9. The method according to claim 6, wherein said CyaA is selected from the group consisting of *Bordetella pertussis* CyA (SEQ ID NO: 1), *Bordetella parapertussis* CyA (SEQ ID NO: 2) and *Bordetella bronchiseptica* CyA (SEQ ID NO: 3).

10. The method according to claim 8, wherein said CyaA fragment specifically binds to CD11b-expressing cells and consists of residues 1 to 224 and 235 to 1706 of *B. pertussis* CyaA (SEQ ID NO: 1).

11. The method according to claim 8, wherein said CyaA protein is detoxified, non-toxic or devoid of enzymatic activity.

12. The method according to claim 10, wherein CyaA fragment is detoxified, non-toxic or devoid of enzymatic activity.

13. The method according to claim 1, wherein said CyaA protein or CyaA fragment comprises at least one, or all, of the epitopes as a result of genetic fusion.

14. The method according to claim 13, wherein at least one, or all, of the epitopes are genetically inserted into the CyaA protein.

15. The method according to claim 1, wherein said epitopes are derived from a tumor antigen or a pathogen antigen.

16. The method according to claim 15, wherein said epitopes are derived from a bacterial antigen, a viral antigen, a fungus antigen or a parasite antigen.

17. The method according to claim 15, wherein said first group of epitopes is present in an antigenic fragment of the E7 protein from HPV16, and said second group of epitopes is present in an antigenic fragment of the E7 protein from HPV18.

18. The method according to claim 7, wherein:
(a) the first group of epitopes consists of the first 29 amino acid residues of HPV16-E7 inserted between amino acid residues corresponding to codons 319 and 320 of the sequence of the CyaA protein (SEQ ID NOS: 4-6), and of the residues 43 to 98 of HPV16-E7 inserted between amino acid residues corresponding to codons 224 and 235 of the sequence of the CyaA protein (SEQ ID NOS: 4-6); and
(b) the second group of epitopes consists of the first 31 amino acid residues of HPV18-E7 inserted between amino acid residues corresponding to codons 319 and 320 of the sequence of the CyaA protein (SEQ ID NOS: 4-6), and the residues 43 to 105 of HPV18-E7 inserted between amino acid residues corresponding to codons 224 and 235 of the sequence of the CyaA protein (SEQ ID NOS: 4-6).

19. The method according to claim 15, wherein said at least one epitope is from the polypeptide sequence of a MAGE A3 tumor antigen.

20. The method according to claim 19, wherein said polypeptides are present in the *B. pertussis* CyaA protein sequence (SEQ ID NO: 1), and wherein:
(a) the first polypeptide consists of residues 97 to 178 of MAGE A3 and has been inserted between amino acid residues corresponding to codons 319 and 320 of CyaA (SEQ ID NO: 4); and
(b) the second polypeptide consists of residues 190 to 221 fused to residues 242 to 295 of MAGE A3 and has been inserted between amino acid residues corresponding to codons 224 and 235 of CyaA (SEQ ID NO: 4).

21. The method according to claim 1, further comprising administering at least one adjuvant.

22. The method according to claim 11, wherein said CyaA protein comprises a dipeptide Leu-Gln inserted in frame between residues 188 and 189 of *B. pertussis* CyaA (SEQ ID NO: 1).

23. The method according to claim 12, wherein said CyaA protein comprises a dipeptide Leu-Gln inserted in frame between residues 188 and 189 of *B. pertussis* CyaA (SEQ ID NO: 1).

24. The method according to claim 14, wherein the epitopes are genetically inserted into permissive sites of the CyaA protein.

25. The method of claim 17, wherein the mammalian host has been diagnosed with HPV16 and HPV18 infection.

26. The method of claim 17, wherein said prophylaxis against said second determined pathological condition is not observed when the vector carrying the polypeptide derived from the E7 protein of HPV18 is not administered to the mammalian host.

27. The method of claim 17, wherein said prophylaxis against said second determined pathological condition is not observed when the vector carrying the polypeptide derived from the E7 protein of HPV16 is not administered to the mammalian host.

28. The method according to claim 1, further comprising administering at least one antitumoral or antiviral active compound.

29. The method according to claim 1, wherein the composition is administered in a prime-boost regimen said composition being administered to the host at least twice.

* * * * *

SEQUENCE LISTING

```
<160> NUMBER OF SEQ ID NOS: 9

<210> SEQ ID NO 1
<211> LENGTH: 1706
<212> TYPE: PRT
<213> ORGANISM: Bordetella pertussis
<220> FEATURE:
<221> NAME/KEY: misc_feature
<223> OTHER INFORMATION: Protein sequence of adenylate cyclase (CyaA)

<400> SEQUENCE: 1

Met Gln Gln Ser His Gln Ala Gly Tyr Ala Asn Ala Ala Asp Arg Glu
1               5                   10                  15

Ser Gly Ile Pro Ala Ala Val Leu Asp Gly Ile Lys Ala Val Ala Lys
            20                  25                  30

Glu Lys Asn Ala Thr Leu Met Phe Arg Leu Val Asn Pro His Ser Thr
        35                  40                  45

Ser Leu Ile Ala Glu Gly Val Ala Thr Lys Gly Leu Gly Val His Ala
    50                  55                  60

Lys Ser Ser Asp Trp Gly Leu Gln Ala Gly Tyr Ile Pro Val Asn Pro
65                  70                  75                  80

Asn Leu Ser Lys Leu Phe Gly Arg Ala Pro Glu Val Ile Ala Arg Ala
                85                  90                  95

Asp Asn Asp Val Asn Ser Ser Leu Ala His Gly His Thr Ala Val Asp
            100                 105                 110

Leu Thr Leu Ser Lys Glu Arg Leu Asp Tyr Leu Arg Gln Ala Gly Leu
        115                 120                 125

Val Thr Gly Met Ala Asp Gly Val Val Ala Ser Asn His Ala Gly Tyr
    130                 135                 140

Glu Gln Phe Glu Phe Arg Val Lys Glu Thr Ser Asp Gly Arg Tyr Ala
145                 150                 155                 160

Val Gln Tyr Arg Arg Lys Gly Gly Asp Asp Phe Glu Ala Val Lys Val
                165                 170                 175

Ile Gly Asn Ala Ala Gly Ile Pro Leu Thr Ala Asp Ile Asp Met Phe
            180                 185                 190

Ala Ile Met Pro His Leu Ser Asn Phe Arg Asp Ser Ala Arg Ser Ser
        195                 200                 205

Val Thr Ser Gly Asp Ser Val Thr Asp Tyr Leu Ala Arg Thr Arg Arg
    210                 215                 220

Ala Ala Ser Glu Ala Thr Gly Gly Leu Asp Arg Glu Arg Ile Asp Leu
225                 230                 235                 240

Leu Trp Lys Ile Ala Arg Ala Gly Ala Arg Ser Ala Val Gly Thr Glu
                245                 250                 255

Ala Arg Arg Gln Phe Arg Tyr Asp Gly Asp Met Asn Ile Gly Val Ile
            260                 265                 270

Thr Asp Phe Glu Leu Glu Val Arg Asn Ala Leu Asn Arg Arg Ala His
        275                 280                 285
```

-continued

Ala Val Gly Ala Gln Asp Val Val Gln His Gly Thr Glu Gln Asn Asn
            290                 295                 300

Pro Phe Pro Glu Ala Asp Glu Lys Ile Phe Val Val Ser Ala Thr Gly
305                 310                 315                 320

Glu Ser Gln Met Leu Thr Arg Gly Gln Leu Lys Glu Tyr Ile Gly Gln
            325                 330                 335

Gln Arg Gly Glu Gly Tyr Val Phe Tyr Glu Asn Arg Ala Tyr Gly Val
            340                 345                 350

Ala Gly Lys Ser Leu Phe Asp Asp Gly Leu Gly Ala Ala Pro Gly Val
            355                 360                 365

Pro Ser Gly Arg Ser Lys Phe Ser Pro Asp Val Leu Glu Thr Val Pro
370                 375                 380

Ala Ser Pro Gly Leu Arg Arg Pro Ser Leu Gly Ala Val Glu Arg Gln
385                 390                 395                 400

Asp Ser Gly Tyr Asp Ser Leu Asp Gly Val Gly Ser Arg Ser Phe Ser
            405                 410                 415

Leu Gly Glu Val Ser Asp Met Ala Ala Val Glu Ala Ala Glu Leu Glu
            420                 425                 430

Met Thr Arg Gln Val Leu His Ala Gly Ala Arg Gln Asp Asp Ala Glu
            435                 440                 445

Pro Gly Val Ser Gly Ala Ser Ala His Trp Gly Gln Arg Ala Leu Gln
450                 455                 460

Gly Ala Gln Ala Val Ala Ala Gln Arg Leu Val His Ala Ile Ala
465                 470                 475                 480

Leu Met Thr Gln Phe Gly Arg Ala Gly Ser Thr Asn Thr Pro Gln Glu
            485                 490                 495

Ala Ala Ser Leu Ser Ala Ala Val Phe Gly Leu Gly Glu Ala Ser Ser
            500                 505                 510

Ala Val Ala Glu Thr Val Ser Gly Phe Phe Arg Gly Ser Ser Arg Trp
            515                 520                 525

Ala Gly Gly Phe Gly Val Ala Gly Ala Met Ala Leu Gly Gly Gly
            530                 535                 540

Ile Ala Ala Ala Val Gly Ala Gly Met Ser Leu Thr Asp Asp Ala Pro
545                 550                 555                 560

Ala Gly Gln Lys Ala Ala Gly Ala Glu Ile Ala Leu Gln Leu Thr
            565                 570                 575

Gly Gly Thr Val Glu Leu Ala Ser Ser Ile Ala Leu Ala Leu Ala Ala
            580                 585                 590

Ala Arg Gly Val Thr Ser Gly Leu Gln Val Ala Gly Ala Ser Ala Gly
            595                 600                 605

Ala Ala Ala Gly Ala Leu Ala Ala Leu Ser Pro Met Glu Ile Tyr
610                 615                 620

Gly Leu Val Gln Gln Ser His Tyr Ala Asp Gln Leu Asp Lys Leu Ala
625                 630                 635                 640

Gln Glu Ser Ser Ala Tyr Gly Tyr Glu Gly Asp Ala Leu Leu Ala Gln
            645                 650                 655

Leu Tyr Arg Asp Lys Thr Ala Ala Glu Gly Ala Val Ala Gly Val Ser
            660                 665                 670

Ala Val Leu Ser Thr Val Gly Ala Val Ser Ile Ala Ala Ala
            675                 680                 685

Ser Val Val Gly Ala Pro Val Ala Val Val Thr Ser Leu Leu Thr Gly
            690                 695                 700

Ala Leu Asn Gly Ile Leu Arg Gly Val Gln Gln Pro Ile Ile Glu Lys

-continued

|     |     |     |     |     |     |     |     |     |     |     |     |
|-----|-----|-----|-----|-----|-----|-----|-----|-----|-----|-----|-----|
| 705 |     |     |     | 710 |     |     |     | 715 |     |     | 720 |
| Leu | Ala | Asn | Asp | Tyr | Ala | Arg | Lys | Ile | Asp | Glu | Leu Gly Gly Pro Gln |
|     |     |     | 725 |     |     |     | 730 |     |     |     | 735 |
| Ala | Tyr | Phe | Glu | Lys | Asn | Leu | Gln | Ala | Arg | His | Glu Gln Leu Ala Asn |
|     |     |     | 740 |     |     |     | 745 |     |     |     | 750 |

Ser Asp Gly Leu Arg Lys Met Leu Ala Asp Leu Gln Ala Gly Trp Asn
                755                 760                 765

Ala Ser Ser Val Ile Gly Val Gln Thr Thr Glu Ile Ser Lys Ser Ala
                770                 775                 780

Leu Glu Leu Ala Ala Ile Thr Gly Asn Ala Asp Asn Leu Lys Ser Val
785                 790                 795                 800

Asp Val Phe Val Asp Arg Phe Val Gln Gly Glu Arg Val Ala Gly Gln
                805                 810                 815

Pro Val Val Leu Asp Val Ala Gly Gly Ile Asp Ile Ala Ser Arg
                820                 825                 830

Lys Gly Glu Arg Pro Ala Leu Thr Phe Ile Thr Pro Leu Ala Ala Pro
                835                 840                 845

Gly Glu Glu Gln Arg Arg Thr Lys Thr Gly Lys Ser Glu Phe Thr
850                 855                 860

Thr Phe Val Glu Ile Val Gly Lys Gln Asp Arg Trp Arg Ile Arg Asp
865                 870                 875                 880

Gly Ala Ala Asp Thr Thr Ile Asp Leu Ala Lys Val Val Ser Gln Leu
                885                 890                 895

Val Asp Ala Asn Gly Val Leu Lys His Ser Ile Lys Leu Asp Val Ile
                900                 905                 910

Gly Gly Asp Gly Asp Val Val Leu Ala Asn Ala Ser Arg Ile His
                915                 920                 925

Tyr Asp Gly Gly Ala Gly Thr Asn Thr Val Ser Tyr Ala Ala Leu Gly
                930                 935                 940

Arg Gln Asp Ser Ile Thr Val Ser Ala Asp Gly Glu Arg Phe Asn Val
945                 950                 955                 960

Arg Lys Gln Leu Asn Asn Ala Asn Val Tyr Arg Glu Gly Val Ala Thr
                965                 970                 975

Gln Thr Thr Ala Tyr Gly Lys Arg Thr Glu Asn Val Gln Tyr Arg His
                980                 985                 990

Val Glu Leu Ala Arg Val Gly Gln Leu Val Glu Val Asp Thr Leu Glu
                995                 1000                1005

His Val Gln His Ile Ile Gly Gly Ala Gly Asn Asp Ser Ile Thr
                1010                1015                1020

Gly Asn Ala His Asp Asn Phe Leu Ala Gly Gly Ser Gly Asp Asp
                1025                1030                1035

Arg Leu Asp Gly Gly Ala Gly Asn Asp Thr Leu Val Gly Gly Glu
                1040                1045                1050

Gly Gln Asn Thr Val Ile Gly Gly Ala Gly Asp Asp Val Phe Leu
                1055                1060                1065

Gln Asp Leu Gly Val Trp Ser Asn Gln Leu Asp Gly Gly Ala Gly
                1070                1075                1080

Val Asp Thr Val Lys Tyr Asn Val His Gln Pro Ser Glu Glu Arg
                1085                1090                1095

Leu Glu Arg Met Gly Asp Thr Gly Ile His Ala Asp Leu Gln Lys
                1100                1105                1110

Gly Thr Val Glu Lys Trp Pro Ala Leu Asn Leu Phe Ser Val Asp
                1115                1120                1125

```
His Val Lys Asn Ile Glu Asn Leu His Gly Ser Arg Leu Asn Asp
1130                1135                1140

Arg Ile Ala Gly Asp Asp Gln Asp Asn Glu Leu Trp Gly His Asp
1145                1150                1155

Gly Asn Asp Thr Ile Arg Gly Arg Gly Gly Asp Asp Ile Leu Arg
1160                1165                1170

Gly Gly Leu Gly Leu Asp Thr Leu Tyr Gly Glu Asp Gly Asn Asp
1175                1180                1185

Ile Phe Leu Gln Asp Asp Glu Thr Val Ser Asp Asp Ile Asp Gly
1190                1195                1200

Gly Ala Gly Leu Asp Thr Val Asp Tyr Ser Ala Met Ile His Pro
1205                1210                1215

Gly Arg Ile Val Ala Pro His Glu Tyr Gly Phe Gly Ile Glu Ala
1220                1225                1230

Asp Leu Ser Arg Glu Trp Val Arg Lys Ala Ser Ala Leu Gly Val
1235                1240                1245

Asp Tyr Tyr Asp Asn Val Arg Asn Val Glu Asn Val Ile Gly Thr
1250                1255                1260

Ser Met Lys Asp Val Leu Ile Gly Asp Ala Gln Ala Asn Thr Leu
1265                1270                1275

Met Gly Gln Gly Gly Asp Asp Thr Val Arg Gly Gly Asp Gly Asp
1280                1285                1290

Asp Leu Leu Phe Gly Gly Asp Gly Asn Asp Met Leu Tyr Gly Asp
1295                1300                1305

Ala Gly Asn Asp Thr Leu Tyr Gly Gly Leu Gly Asp Asp Thr Leu
1310                1315                1320

Glu Gly Gly Ala Gly Asn Asp Trp Phe Gly Gln Thr Gln Ala Arg
1325                1330                1335

Glu His Asp Val Leu Arg Gly Gly Asp Gly Val Asp Thr Val Asp
1340                1345                1350

Tyr Ser Gln Thr Gly Ala His Ala Gly Ile Ala Ala Gly Arg Ile
1355                1360                1365

Gly Leu Gly Ile Leu Ala Asp Leu Gly Ala Gly Arg Val Asp Lys
1370                1375                1380

Leu Gly Glu Ala Gly Ser Ser Ala Tyr Asp Thr Val Ser Gly Ile
1385                1390                1395

Glu Asn Val Val Gly Thr Glu Leu Ala Asp Arg Ile Thr Gly Asp
1400                1405                1410

Ala Gln Ala Asn Val Leu Arg Gly Ala Gly Gly Ala Asp Val Leu
1415                1420                1425

Ala Gly Gly Glu Gly Asp Asp Val Leu Leu Gly Gly Asp Gly Asp
1430                1435                1440

Asp Gln Leu Ser Gly Asp Ala Gly Arg Asp Arg Leu Tyr Gly Glu
1445                1450                1455

Ala Gly Asp Asp Trp Phe Phe Gln Asp Ala Ala Asn Ala Gly Asn
1460                1465                1470

Leu Leu Asp Gly Gly Asp Gly Arg Asp Thr Val Asp Phe Ser Gly
1475                1480                1485

Pro Gly Arg Gly Leu Asp Ala Gly Ala Lys Gly Val Phe Leu Ser
1490                1495                1500

Leu Gly Lys Gly Phe Ala Ser Leu Met Asp Glu Pro Glu Thr Ser
1505                1510                1515
```

```
Asn Val  Leu Arg Asn Ile Glu  Asn Ala Val Gly Ser  Ala Arg Asp
    1520                1525                1530

Asp Val  Leu Ile Gly Asp Ala  Gly Ala Asn Val Leu  Asn Gly Leu
    1535                1540                1545

Ala Gly  Asn Asp Val Leu Ser  Gly Gly Ala Gly Asp  Asp Val Leu
    1550                1555                1560

Leu Gly  Asp Glu Gly Ser Asp  Leu Leu Ser Gly Asp  Ala Gly Asn
    1565                1570                1575

Asp Asp  Leu Phe Gly Gly Gln  Gly Asp Asp Thr Tyr  Leu Phe Gly
    1580                1585                1590

Val Gly  Tyr Gly His Asp Thr  Ile Tyr Glu Ser Gly  Gly Gly His
    1595                1600                1605

Asp Thr  Ile Arg Ile Asn Ala  Gly Ala Asp Gln Leu  Trp Phe Ala
    1610                1615                1620

Arg Gln  Gly Asn Asp Leu Glu  Ile Arg Ile Leu Gly  Thr Asp Asp
    1625                1630                1635

Ala Leu  Thr Val His Asp Trp  Tyr Arg Asp Ala Asp  His Arg Val
    1640                1645                1650

Glu Ile  Ile His Ala Ala Asn  Gln Ala Val Asp Gln  Ala Gly Ile
    1655                1660                1665

Glu Lys  Leu Val Glu Ala Met  Ala Gln Tyr Pro Asp  Pro Gly Ala
    1670                1675                1680

Ala Ala  Ala Ala Pro Pro Ala  Ala Arg Val Pro Asp  Thr Leu Met
    1685                1690                1695

Gln Ser  Leu Ala Val Asn Trp  Arg
    1700                1705

<210> SEQ ID NO 2
<211> LENGTH: 1740
<212> TYPE: PRT
<213> ORGANISM: Bordetella parapertussis
<220> FEATURE:
<221> NAME/KEY: misc_feature
<223> OTHER INFORMATION: Protein sequence of adenylate cyclase (CyaA)

<400> SEQUENCE: 2

Met Leu Asp Val Trp Phe Leu Gln Lys Asp Glu Val Leu Ser Ala Thr
1               5                   10                  15

His Arg Leu Arg Arg Cys Glu Ser Val Gln Ser Thr Thr Tyr Arg Gln
            20                  25                  30

Ile His Met Gln Gln Ser His Gln Ala Gly Tyr Ala Asn Ala Ala Asp
        35                  40                  45

Arg Glu Ser Gly Ile Pro Ala Ala Val Leu Asp Gly Ile Lys Ala Val
    50                  55                  60

Ala Lys Glu Lys Asn Ala Thr Leu Met Phe Arg Leu Val Asn Pro His
65                  70                  75                  80

Ser Thr Ser Leu Ile Ala Glu Gly Val Ala Thr Lys Gly Leu Gly Val
                85                  90                  95

His Ala Lys Ser Ser Asp Trp Gly Leu Gln Ala Gly Tyr Ile Pro Val
            100                 105                 110

Asn Pro Asn Leu Ser Lys Leu Phe Gly Arg Ala Pro Glu Val Ile Ala
        115                 120                 125

Arg Ala Asp Asn Asp Val Asn Ser Ser Leu Ala His Gly His Thr Ala
    130                 135                 140

Val Asp Leu Thr Leu Ser Lys Glu Arg Leu Asp Tyr Leu Arg Gln Ala
145                 150                 155                 160
```

```
Gly Leu Val Thr Gly Met Ala Asp Gly Val Ala Ser Asn His Ala
            165                 170                 175

Gly Tyr Glu Gln Phe Glu Phe Arg Val Lys Glu Thr Ser Asp Gly Arg
        180                 185                 190

Tyr Ala Val Gln Tyr Arg Arg Lys Gly Asp Asp Phe Glu Ala Val
            195                 200                 205

Lys Val Ile Gly Asn Ala Ala Gly Ile Pro Leu Thr Ala Asp Ile Asp
            210                 215                 220

Met Phe Ala Ile Met Pro His Leu Ser Asn Phe Arg Asp Ser Ala Arg
225                 230                 235                 240

Ser Ser Val Thr Ser Gly Asp Ser Val Thr Asp Tyr Leu Ala Arg Thr
            245                 250                 255

Arg Arg Ala Ala Ser Glu Ala Thr Gly Gly Leu Asp Arg Glu Arg Ile
            260                 265                 270

Asp Leu Leu Trp Lys Ile Ala Arg Ala Gly Ala Arg Ser Ala Val Gly
            275                 280                 285

Thr Glu Ala Arg Arg Gln Phe Arg Tyr Asp Gly Asp Met Asn Ile Gly
            290                 295                 300

Val Ile Thr Asp Phe Glu Leu Glu Val Arg Asn Ala Leu Asn Arg Arg
305                 310                 315                 320

Ala His Ala Val Gly Ala Gln Asp Val Val Gln His Gly Thr Glu Gln
            325                 330                 335

Asn Asn Pro Phe Pro Glu Ala Asp Glu Lys Ile Phe Val Val Ser Ala
            340                 345                 350

Thr Gly Glu Ser Gln Met Leu Thr Arg Gly Gln Leu Lys Glu Tyr Ile
            355                 360                 365

Gly Gln Gln Arg Gly Glu Gly Tyr Val Phe Tyr Glu Asn Arg Ala Tyr
            370                 375                 380

Gly Val Ala Gly Lys Ser Leu Phe Asp Asp Gly Leu Gly Ala Ala Pro
385                 390                 395                 400

Gly Val Pro Gly Gly Arg Ser Lys Ser Ser Pro Asp Val Leu Glu Thr
            405                 410                 415

Val Pro Ala Ser Pro Gly Leu Arg Pro Ser Leu Gly Ala Val Glu
            420                 425                 430

Arg Gln Asp Ser Gly Tyr Asp Ser Leu Asp Gly Val Gly Ser Arg Ser
            435                 440                 445

Phe Ser Leu Gly Glu Val Ser Asp Met Ala Ala Val Glu Ala Ala Glu
450                 455                 460

Leu Glu Met Thr Arg Gln Val Leu His Ala Gly Ala Arg Gln Asp Asp
465                 470                 475                 480

Ala Glu Pro Gly Val Ser Gly Ala Ser Ala His Trp Gly Gln Arg Ala
            485                 490                 495

Leu Gln Gly Ala Gln Ala Val Ala Ala Gln Arg Leu Val His Ala
            500                 505                 510

Ile Ala Leu Met Thr Gln Phe Gly Arg Ala Gly Ser Thr Asn Thr Pro
            515                 520                 525

Gln Glu Ala Ala Ser Leu Ser Ala Ala Val Phe Gly Leu Gly Glu Ala
            530                 535                 540

Ser Ser Ala Val Ala Glu Thr Val Ser Gly Phe Phe Arg Gly Ser Ser
545                 550                 555                 560

Arg Trp Ala Gly Gly Phe Gly Val Ala Gly Gly Ala Met Ala Leu Gly
            565                 570                 575
```

```
Gly Gly Ile Ala Ala Ala Val Gly Ala Gly Met Ser Leu Thr Asp Asp
            580                 585                 590

Ala Pro Ala Gly Gln Lys Ala Ala Val Gly Ala Glu Ile Ala Leu Gln
595                 600                 605

Leu Thr Gly Gly Thr Val Glu Leu Ala Ser Ser Ile Ala Leu Ala Leu
    610                 615                 620

Ala Ala Ala Arg Gly Val Thr Ser Gly Leu Gln Val Ala Gly Ala Ser
625                 630                 635                 640

Ala Gly Ala Ala Ala Gly Ala Leu Ala Ala Leu Ser Pro Met Glu
        645                 650                 655

Ile Tyr Gly Leu Val Gln Gln Ser His Tyr Ala Asp Gln Leu Asp Lys
            660                 665                 670

Leu Ala Gln Glu Ser Ser Ala Tyr Gly Tyr Glu Gly Asp Ala Leu Leu
    675                 680                 685

Ala Gln Leu Tyr Arg Asp Lys Thr Ala Ala Glu Gly Ala Val Ala Gly
    690                 695                 700

Val Ser Ala Val Leu Ser Thr Val Gly Ala Ala Val Ser Ile Ala Ala
705                 710                 715                 720

Ala Ala Ser Val Val Gly Ala Pro Val Ala Val Val Thr Ser Leu Leu
            725                 730                 735

Thr Gly Ala Leu Asn Gly Ile Leu Arg Gly Val Gln Gln Pro Ile Ile
        740                 745                 750

Glu Lys Leu Ala Asn Asp Tyr Ala Arg Lys Ile Asp Glu Leu Gly Gly
        755                 760                 765

Pro Gln Ala Tyr Phe Glu Lys Asn Leu Gln Ala Arg His Glu Gln Leu
    770                 775                 780

Ala Asn Ser Asp Gly Leu Arg Lys Met Leu Ala Asp Leu Gln Ala Gly
785                 790                 795                 800

Trp Asn Ala Ser Ser Val Ile Gly Val Gln Thr Thr Glu Ile Ser Lys
            805                 810                 815

Ser Ala Leu Glu Leu Ala Ala Ile Thr Gly Asn Ala Asp Asn Leu Lys
        820                 825                 830

Ser Ala Asp Val Phe Val Asp Arg Phe Ile Gln Gly Glu Arg Val Ala
        835                 840                 845

Gly Gln Pro Val Val Leu Asp Val Ala Ala Gly Gly Ile Asp Ile Ala
850                 855                 860

Ser Arg Lys Gly Glu Arg Pro Ala Leu Thr Phe Ile Thr Pro Leu Ala
865                 870                 875                 880

Ala Pro Gly Glu Glu Gln Arg Arg Thr Lys Thr Gly Lys Ser Glu
            885                 890                 895

Phe Thr Thr Phe Val Glu Ile Val Gly Lys Gln Asp Arg Trp Arg Ile
            900                 905                 910

Arg Asp Gly Ala Ala Asp Thr Thr Ile Asp Leu Ala Lys Val Val Ser
        915                 920                 925

Gln Leu Val Asp Ala Asn Gly Val Leu Lys His Ser Ile Lys Leu Glu
    930                 935                 940

Val Ile Gly Gly Asp Gly Asp Val Val Leu Ala Asn Ala Ser Arg
945                 950                 955                 960

Ile His Tyr Asp Gly Gly Ala Gly Thr Asn Thr Val Ser Tyr Ala Ala
            965                 970                 975

Leu Gly Arg Gln Asp Ser Ile Thr Val Ser Ala Asp Gly Glu Arg Phe
    980                 985                 990

Asn Val Arg Lys Gln Leu Asn Asn  Ala Asn Val Tyr Arg  Glu Gly Val
```

-continued

```
             995                 1000               1005
Ala Thr Gln Lys Thr Ala Tyr Gly Lys Arg Thr Glu Asn Val Gln
             1010               1015              1020

Tyr Arg His Val Glu Leu Ala Arg Val Gly Gln Leu Val Glu Val
             1025               1030              1035

Asp Thr Leu Glu His Val Gln His Ile Ile Gly Gly Ala Gly Asn
             1040               1045              1050

Asp Ser Ile Thr Gly Asn Ala His Asp Asn Phe Leu Ala Gly Gly
             1055               1060              1065

Ala Gly Asp Asp Arg Leu Asp Gly Gly Ala Gly Asn Asp Thr Leu
             1070               1075              1080

Val Gly Gly Glu Gly His Asn Thr Val Val Gly Gly Ala Gly Asp
             1085               1090              1095

Asp Val Phe Leu Gln Asp Leu Gly Val Trp Ser Asn Gln Leu Asp
             1100               1105              1110

Gly Gly Ala Gly Val Asp Thr Val Lys Tyr Asn Val His Gln Pro
             1115               1120              1125

Ser Glu Glu Arg Leu Glu Arg Met Gly Asp Thr Gly Ile His Ala
             1130               1135              1140

Asp Leu Gln Lys Gly Thr Val Glu Lys Trp Pro Ala Leu Asn Leu
             1145               1150              1155

Phe Ser Val Asp His Val Lys Asn Ile Glu Asn Leu His Gly Ser
             1160               1165              1170

Ser Leu Asn Asp Ser Ile Ala Gly Asp Asp Arg Asp Asn Glu Leu
             1175               1180              1185

Trp Gly Asp Asp Gly Asn Asp Thr Ile His Gly Arg Gly Gly Asp
             1190               1195              1200

Asp Ile Leu Arg Gly Gly Leu Gly Leu Asp Thr Leu Tyr Gly Glu
             1205               1210              1215

Asp Gly Asn Asp Ile Phe Leu Gln Asp Asp Glu Thr Val Ser Asp
             1220               1225              1230

Asp Ile Asp Gly Gly Ala Gly Leu Asp Thr Val Asp Tyr Ser Ala
             1235               1240              1245

Met Ile His Ala Gly Lys Ile Val Ala Pro His Glu Tyr Gly Phe
             1250               1255              1260

Gly Ile Glu Ala Asp Leu Ser Glu Gly Trp Val Arg Lys Ala Ala
             1265               1270              1275

Arg Arg Gly Met Gly Tyr Tyr Asp Ser Val Arg Ser Val Glu Asn
             1280               1285              1290

Val Ile Gly Thr Ser Met Lys Asp Val Leu Ile Gly Asp Ala Gln
             1295               1300              1305

Ala Asn Thr Leu Met Gly Gln Gly Gly Asp Asp Thr Val Arg Gly
             1310               1315              1320

Gly Asp Gly Asp Asp Leu Leu Phe Gly Gly Asp Gly Asn Asp Met
             1325               1330              1335

Leu Tyr Gly Asp Ala Gly Asn Asp Thr Leu Tyr Gly Gly Leu Gly
             1340               1345              1350

Asp Asp Thr Leu Glu Gly Gly Ala Gly Asn Asp Trp Phe Gly Gln
             1355               1360              1365

Thr Pro Ala Arg Glu His Asp Val Leu Arg Gly Gly Ala Gly Val
             1370               1375              1380

Asp Thr Val Asp Tyr Ser Gln Ala Gly Ala His Ala Gly Val Ala
             1385               1390              1395
```

Thr Gly Arg Ile Gly Leu Gly Ile Leu Ala Asp Leu Gly Ala Gly
1400             1405                 1410

Arg Val Asp Lys Leu Gly Glu Ala Gly Ser Ser Ala Tyr Asp Thr
1415             1420                 1425

Val Ser Gly Ile Glu Asn Val Val Gly Thr Glu Leu Ala Asp Arg
1430             1435                 1440

Ile Thr Gly Asp Ala Gln Ala Asn Val Leu Arg Gly Ala Gly Gly
1445             1450                 1455

Ala Asp Val Leu Ala Gly Gly Glu Gly Asp Asp Val Leu Leu Gly
1460             1465                 1470

Gly Glu Gly Asp Asp Gln Leu Ser Gly Asp Ala Gly Arg Asp Arg
1475             1480                 1485

Leu Tyr Gly Glu Ala Gly Asp Asp Trp Phe Phe Gln Asp Ala Ala
1490             1495                 1500

Asn Ala Gly Asn Leu Leu Asp Gly Gly Asp Gly Asn Asp Thr Val
1505             1510                 1515

Asp Phe Ser Gly Pro Gly Arg Gly Leu Asp Ala Gly Ala Lys Gly
1520             1525                 1530

Val Phe Leu Ser Leu Gly Lys Gly Phe Ala Ser Leu Met Asp Glu
1535             1540                 1545

Pro Glu Thr Ser Asn Val Leu Arg His Ile Glu Asn Ala Val Gly
1550             1555                 1560

Ser Val Arg Asp Asp Val Leu Ile Gly Asp Ala Gly Ala Asn Val
1565             1570                 1575

Leu Asn Gly Leu Ala Gly Asn Asp Val Leu Ser Gly Gly Ala Gly
1580             1585                 1590

Asp Asp Val Leu Leu Gly Asp Glu Gly Ser Asp Leu Leu Ser Gly
1595             1600                 1605

Asp Ala Gly Asn Asp Asp Leu Phe Gly Gly Gln Gly Asp Asp Thr
1610             1615                 1620

Tyr Leu Phe Gly Ala Gly Tyr Gly His Asp Thr Ile Tyr Glu Ser
1625             1630                 1635

Gly Gly Gly His Asp Thr Ile Arg Ile Asn Ala Gly Ala Asp Gln
1640             1645                 1650

Leu Trp Phe Ala Arg Gln Gly Asn Asp Leu Glu Ile Arg Ile Leu
1655             1660                 1665

Gly Thr Asp Asp Ala Leu Thr Val His Asp Trp Tyr Arg Asp Ala
1670             1675                 1680

Asp His Arg Val Glu Ala Ile His Ala Ala Asn Gln Ala Ile Asp
1685             1690                 1695

Pro Ala Gly Ile Glu Lys Leu Val Glu Ala Met Ala Gln Tyr Pro
1700             1705                 1710

Asp Pro Gly Ala Ala Ala Ala Pro Pro Ala Ala Arg Val Pro
1715             1720                 1725

Asp Thr Leu Met Gln Ser Leu Ala Val Asn Trp Arg
1730             1735                 1740

<210> SEQ ID NO 3
<211> LENGTH: 1740
<212> TYPE: PRT
<213> ORGANISM: Bordetella bronchiseptica
<220> FEATURE:
<221> NAME/KEY: misc_feature
<223> OTHER INFORMATION: Protein sequence of adenylate cyclase (CyaA)

```
<400> SEQUENCE: 3

Met Leu Asp Val Trp Phe Leu Gln Lys Asp Glu Val Leu Ser Ala Thr
1               5                   10                  15

His Arg Leu Arg Arg Cys Glu Ser Val Gln Ser Thr Thr Tyr Arg Gln
            20                  25                  30

Ile His Met Gln Gln Ser His Gln Ala Gly Tyr Ala Asn Ala Ala Asp
        35                  40                  45

Arg Glu Ser Gly Ile Pro Ala Ala Val Leu Asp Gly Ile Lys Ala Val
    50                  55                  60

Ala Lys Glu Lys Asn Ala Thr Leu Met Phe Arg Leu Val Asn Pro His
65                  70                  75                  80

Ser Thr Ser Leu Ile Ala Glu Gly Val Ala Thr Lys Gly Leu Gly Val
                85                  90                  95

His Ala Lys Ser Ser Asp Trp Gly Leu Gln Ala Gly Tyr Ile Pro Val
            100                 105                 110

Asn Pro Asn Leu Ser Lys Leu Phe Gly Arg Ala Pro Glu Val Ile Ala
        115                 120                 125

Arg Ala Asp Asn Asp Val Asn Ser Ser Leu Ala His Gly His Thr Ala
    130                 135                 140

Val Asp Leu Thr Leu Ser Lys Glu Arg Leu Asp Tyr Leu Arg Gln Ala
145                 150                 155                 160

Gly Leu Val Thr Gly Met Ala Asp Gly Val Val Ala Ser Asn His Ala
                165                 170                 175

Gly Tyr Glu Gln Phe Glu Phe Arg Val Lys Glu Thr Ser Asp Gly Arg
            180                 185                 190

Tyr Ala Val Gln Tyr Arg Arg Lys Gly Gly Asp Asp Phe Glu Ala Val
    195                 200                 205

Lys Val Ile Gly Asn Ala Ala Gly Ile Pro Leu Thr Ala Asp Ile Asp
210                 215                 220

Met Phe Ala Ile Met Pro His Leu Ser Asn Phe Arg Asp Ser Ala Arg
225                 230                 235                 240

Ser Ser Val Thr Ser Gly Asp Ser Val Thr Asp Tyr Leu Ala Arg Thr
                245                 250                 255

Arg Arg Ala Ala Ser Glu Ala Thr Gly Gly Leu Asp Arg Glu Arg Ile
            260                 265                 270

Asp Leu Leu Trp Lys Ile Ala Arg Ala Gly Ala Arg Ser Ala Val Gly
        275                 280                 285

Thr Glu Ala Arg Arg Gln Phe Arg Tyr Asp Gly Asp Met Asn Ile Gly
    290                 295                 300

Val Ile Thr Asp Phe Glu Leu Glu Val Arg Asn Ala Leu Asn Arg Arg
305                 310                 315                 320

Ala His Ala Val Gly Ala Gln Asp Val Val Gln His Gly Thr Glu Gln
                325                 330                 335

Asn Asn Pro Phe Pro Glu Ala Asp Glu Lys Ile Phe Val Val Ser Ala
            340                 345                 350

Thr Gly Glu Ser Gln Met Leu Thr Arg Gly Gln Leu Lys Glu Tyr Ile
        355                 360                 365

Gly Gln Gln Arg Gly Glu Gly Tyr Val Phe Tyr Glu Asn Arg Ala Tyr
    370                 375                 380

Gly Val Ala Gly Lys Ser Leu Phe Asp Asp Gly Leu Gly Ala Ala Pro
385                 390                 395                 400

Gly Val Pro Gly Gly Arg Ser Lys Ser Ser Pro Asp Val Leu Glu Thr
                405                 410                 415
```

-continued

Val Pro Ala Ser Pro Gly Leu Arg Arg Pro Ser Leu Gly Ala Val Glu
            420                 425                 430

Arg Gln Asp Ser Gly Tyr Asp Ser Leu Asp Gly Val Gly Ser Arg Ser
        435                 440                 445

Phe Ser Leu Gly Glu Val Ser Asp Met Ala Ala Val Glu Ala Ala Glu
    450                 455                 460

Leu Glu Met Thr Arg Gln Val Leu His Ala Gly Ala Arg Gln Asp Asp
465                 470                 475                 480

Ala Glu Pro Gly Val Ser Gly Ala Ser Ala His Trp Gly Gln Arg Ala
                485                 490                 495

Leu Gln Gly Ala Gln Ala Val Ala Ala Gln Arg Leu Val His Ala
            500                 505                 510

Ile Ala Leu Met Thr Gln Phe Gly Arg Ala Gly Ser Thr Asn Thr Pro
        515                 520                 525

Gln Glu Ala Ala Ser Leu Ser Ala Ala Val Phe Gly Leu Gly Glu Ala
530                 535                 540

Ser Ser Ala Val Ala Glu Thr Val Ser Gly Phe Phe Arg Gly Ser Ser
545                 550                 555                 560

Arg Trp Ala Gly Gly Phe Gly Val Ala Gly Ala Met Ala Leu Gly
                565                 570                 575

Gly Gly Ile Ala Ala Ala Val Gly Ala Gly Met Ser Leu Thr Asp Asp
            580                 585                 590

Ala Pro Ala Gly Gln Lys Ala Ala Gly Ala Glu Ile Ala Leu Gln
        595                 600                 605

Leu Thr Gly Gly Thr Val Glu Leu Ala Ser Ser Ile Ala Leu Ala Leu
            610                 615                 620

Ala Ala Ala Arg Gly Val Thr Ser Gly Leu Gln Val Ala Gly Ala Ser
625                 630                 635                 640

Ala Gly Ala Ala Ala Gly Ala Leu Ala Ala Leu Ser Pro Met Glu
                645                 650                 655

Ile Tyr Gly Leu Val Gln Gln Ser His Tyr Ala Asp Gln Leu Asp Lys
            660                 665                 670

Leu Ala Gln Glu Ser Ser Ala Tyr Gly Tyr Glu Gly Asp Ala Leu Leu
        675                 680                 685

Ala Gln Leu Tyr Arg Asp Lys Thr Ala Glu Gly Ala Val Ala Gly
    690                 695                 700

Val Ser Ala Val Leu Ser Thr Val Gly Ala Ala Val Ser Ile Ala Ala
705                 710                 715                 720

Ala Ala Ser Val Val Gly Ala Pro Val Ala Val Thr Ser Leu Leu
                725                 730                 735

Thr Gly Ala Leu Asn Gly Ile Leu Arg Gly Val Gln Gln Pro Ile Ile
            740                 745                 750

Glu Lys Leu Ala Asn Asp Tyr Ala Arg Lys Ile Asp Glu Leu Gly Gly
        755                 760                 765

Pro Gln Ala Tyr Phe Glu Lys Asn Leu Gln Ala Arg His Glu Gln Leu
    770                 775                 780

Ala Asn Ser Asp Gly Leu Arg Lys Met Leu Ala Asp Leu Gln Ala Gly
785                 790                 795                 800

Trp Asn Ala Ser Ser Val Ile Gly Val Gln Thr Thr Glu Ile Ser Lys
                805                 810                 815

Ser Ala Leu Glu Leu Ala Ala Ile Thr Gly Asn Ala Asp Asn Leu Lys
            820                 825                 830

```
Ser Ala Asp Val Phe Val Asp Arg Phe Ile Gln Gly Glu Arg Val Ala
         835                 840                 845
Gly Gln Pro Val Val Leu Asp Val Ala Gly Gly Ile Asp Ile Ala
850                 855                 860
Ser Arg Lys Gly Glu Arg Pro Ala Leu Thr Phe Ile Thr Pro Leu Ala
865                 870                 875                 880
Ala Pro Gly Glu Glu Gln Arg Arg Thr Lys Thr Gly Lys Ser Glu
                885                 890                 895
Phe Thr Thr Phe Val Glu Ile Val Gly Lys Gln Asp Arg Trp Arg Ile
                900                 905                 910
Arg Asp Gly Ala Ala Asp Thr Thr Ile Asp Leu Ala Lys Val Val Ser
            915                 920                 925
Gln Leu Val Asp Ala Asn Gly Val Leu Lys His Ser Ile Lys Leu Glu
930                 935                 940
Val Ile Gly Gly Asp Gly Asp Asp Val Val Leu Ala Asn Ala Ser Arg
945                 950                 955                 960
Ile His Tyr Asp Gly Gly Ala Gly Thr Asn Thr Val Ser Tyr Ala Ala
                965                 970                 975
Leu Gly Arg Gln Asp Ser Ile Thr Val Ser Ala Asp Gly Glu Arg Phe
            980                 985                 990
Asn Val Arg Lys Gln Leu Asn Asn Ala Asn Val Tyr Arg Glu Gly Val
        995                1000                1005
Ala Thr Gln Lys Thr Ala Tyr Gly Lys Arg Thr Glu Asn Val Gln
   1010                1015                1020
Tyr Arg His Val Glu Leu Ala Arg Val Gly Gln Leu Val Glu Val
   1025                1030                1035
Asp Thr Leu Glu His Val Gln His Ile Ile Gly Gly Ala Gly Asn
   1040                1045                1050
Asp Ser Ile Thr Gly Asn Ala His Asp Asn Phe Leu Ala Gly Gly
   1055                1060                1065
Ala Gly Asp Asp Arg Leu Asp Gly Gly Ala Gly Asn Asp Thr Leu
   1070                1075                1080
Val Gly Gly Glu Gly His Asn Thr Val Val Gly Gly Ala Gly Asp
   1085                1090                1095
Asp Val Phe Leu Gln Asp Leu Gly Val Trp Ser Asn Gln Leu Asp
   1100                1105                1110
Gly Gly Ala Gly Val Asp Thr Val Lys Tyr Asn Val His Gln Pro
   1115                1120                1125
Ser Glu Glu Arg Leu Glu Arg Met Gly Asp Thr Gly Ile His Ala
   1130                1135                1140
Asp Leu Gln Lys Gly Thr Val Glu Lys Trp Pro Ala Leu Asn Leu
   1145                1150                1155
Phe Ser Val Asp His Val Lys Asn Ile Glu Asn Leu His Gly Ser
   1160                1165                1170
Ser Leu Asn Asp Ser Ile Ala Gly Asp Asp Arg Asp Asn Glu Leu
   1175                1180                1185
Trp Gly Asp Asp Gly Asn Asp Thr Ile His Gly Arg Gly Gly Asp
   1190                1195                1200
Asp Ile Leu Arg Gly Gly Leu Gly Leu Asp Thr Leu Tyr Gly Glu
   1205                1210                1215
Asp Gly Asn Asp Ile Phe Leu Gln Asp Asp Glu Thr Val Ser Asp
   1220                1225                1230
Asp Ile Asp Gly Gly Ala Gly Leu Asp Thr Val Asp Tyr Ser Ala
```

-continued

```
            1235                1240                1245
Met Ile His Ala Gly Lys Ile Val Ala Pro His Glu Tyr Gly Phe
            1250                1255                1260
Gly Ile Glu Ala Asp Leu Ser Glu Gly Trp Val Arg Lys Ala Ala
            1265                1270                1275
Arg Arg Gly Met Asp Tyr Tyr Asp Ser Val Arg Ser Val Glu Asn
            1280                1285                1290
Val Ile Gly Thr Ser Met Lys Asp Val Leu Ile Gly Asp Ala Gln
            1295                1300                1305
Ala Asn Thr Leu Met Gly Gln Gly Gly Asp Thr Val Arg Gly
            1310                1315                1320
Gly Asp Gly Asp Asp Leu Leu Phe Gly Gly Asp Gly Asn Asp Met
            1325                1330                1335
Leu Tyr Gly Asp Ala Gly Asn Asp Thr Leu Tyr Gly Gly Leu Gly
            1340                1345                1350
Asp Asp Thr Leu Glu Gly Gly Ala Gly Asn Asp Trp Phe Gly Gln
            1355                1360                1365
Thr Pro Ala Arg Glu His Asp Val Leu Arg Gly Gly Ala Gly Val
            1370                1375                1380
Asp Thr Val Asp Tyr Ser Gln Ala Gly Ala His Ala Gly Val Ala
            1385                1390                1395
Thr Gly Arg Ile Gly Leu Gly Ile Leu Ala Asp Leu Gly Ala Gly
            1400                1405                1410
Arg Val Asp Lys Leu Gly Glu Ala Gly Ser Ser Ala Tyr Asp Thr
            1415                1420                1425
Val Ser Gly Ile Glu Asn Val Val Gly Thr Glu Leu Ala Asp Arg
            1430                1435                1440
Ile Thr Gly Asp Ala Gln Ala Asn Val Leu Arg Gly Ala Gly Gly
            1445                1450                1455
Ala Asp Val Leu Ala Gly Gly Glu Gly Asp Asp Val Leu Leu Gly
            1460                1465                1470
Gly Asp Gly Asp Asp Gln Leu Ser Gly Asp Ala Gly Arg Asp Arg
            1475                1480                1485
Leu Tyr Gly Glu Ala Gly Asp Asp Trp Phe Phe Gln Asp Ala Ala
            1490                1495                1500
Asn Ala Gly Asn Leu Leu Asp Gly Gly Asp Gly Asn Asp Thr Val
            1505                1510                1515
Asp Phe Ser Gly Pro Gly Arg Gly Leu Asp Ala Gly Ala Lys Gly
            1520                1525                1530
Val Phe Leu Ser Leu Gly Lys Gly Phe Ala Ser Leu Met Asp Glu
            1535                1540                1545
Pro Glu Thr Ser Asn Val Leu Arg His Ile Glu Asn Ala Val Gly
            1550                1555                1560
Ser Val Arg Asp Asp Val Leu Ile Gly Asp Ala Gly Ala Asn Val
            1565                1570                1575
Leu Asn Gly Leu Ala Gly Asn Asp Val Leu Ser Gly Gly Ala Gly
            1580                1585                1590
Asp Asp Val Leu Leu Gly Asp Glu Gly Ser Asp Leu Leu Ser Gly
            1595                1600                1605
Asp Ala Gly Asn Asp Asp Leu Phe Gly Gly Gln Gly Asp Asp Thr
            1610                1615                1620
Tyr Leu Phe Gly Ala Gly Tyr Gly His Asp Thr Ile Tyr Glu Ser
            1625                1630                1635
```

-continued

| Gly | Gly | Gly | His | Asp | Thr | Ile | Arg | Ile | Asn | Ala | Gly | Ala | Asp | Gln |
|     |     | 1640|     |     |     | 1645|     |     |     | 1650|     |     |     |     |

| Leu | Trp | Phe | Ala | Arg | Gln | Gly | Asn | Asp | Leu | Glu | Ile | Arg | Ile | Leu |
|     | 1655|     |     |     |     | 1660|     |     |     |     | 1665|     |     |     |

| Gly | Thr | Asp | Asp | Ala | Leu | Thr | Val | His | Asp | Trp | Tyr | Arg | Asp | Ala |
|     | 1670|     |     |     |     | 1675|     |     |     |     | 1680|     |     |     |

| Asp | His | Arg | Val | Glu | Ala | Ile | His | Ala | Ala | Asn | Gln | Ala | Ile | Asp |
|     | 1685|     |     |     |     | 1690|     |     |     |     | 1695|     |     |     |

| Pro | Ala | Gly | Ile | Glu | Lys | Leu | Val | Glu | Ala | Met | Ala | Gln | Tyr | Pro |
|     | 1700|     |     |     |     | 1705|     |     |     |     | 1710|     |     |     |

| Asp | Pro | Gly | Ala | Ala | Ala | Ala | Ala | Pro | Pro | Ala | Ala | Arg | Val | Pro |
|     | 1715|     |     |     |     | 1720|     |     |     |     | 1725|     |     |     |

| Asp | Thr | Leu | Met | Gln | Ser | Leu | Ala | Val | Asn | Trp | Arg |
|     | 1730|     |     |     |     | 1735|     |     |     |     | 1740|

<210> SEQ ID NO 4
<211> LENGTH: 5121
<212> TYPE: DNA
<213> ORGANISM: Bordetella pertussis
<220> FEATURE:
<221> NAME/KEY: misc_feature
<223> OTHER INFORMATION: Nucleotide sequence of adenylate cyclase (CyaA)
      gene

<400> SEQUENCE: 4

```
atgcagcaat cgcatcaggc tggttacgca aacgccgccg accgggagtc tggcatcccc     60
gcagccgtac tcgatggcat caaggccgtg gcgaaggaaa aaaacgccac attgatgttc    120
cgcctggtca acccccattc caccagcctg attgccgaag ggtggccac caaaggattg     180 ggcgtgcacg ccaagtcgtc cgattggggg ttgcaggcgg gctacattcc cgtcaacccg    240
aatctttcca aactgttcgg ccgtgcgccc gaggtgatcg cgcgggccga caacgacgtc    300
aacagcagcc tggcgcatgg ccataccgcg gtcgacctga cgctgtcgaa agagcggctt    360
gactatctgc ggcaagcggg cctggtcacc ggcatggccg atggcgtggt cgcgagcaac    420
cacgcaggct acgagcagtt cgagtttcgc gtgaaggaaa cctcggacgg gcgctatgcc    480
gtgcagtatc gccgcaaggg cggcgacgat ttcgaggcgg tcaaggtgat cggcaatgcc    540
gccggtattc cactgacggc ggatatcgac atgttcgcca ttatgccgca tctgtccaac    600
ttccgcgact cggcgcgcag ttcggtgacc agcggcgatt cggtgaccga ttacctggcg    660
cgcacgcggc gggccgccag cgaggccacg ggcggcctgg atcgcgaacg catcgacttg    720
ttgtggaaaa tcgctcgcgc cggcgcccgt tccgcagtgg gcaccgaggc gcgtcgccag    780
ttccgctacg acggcgacat gaatatcggc gtgatcaccg atttcgagct ggaagtgcgc    840
aatgcgctga acaggcgggc gcacgccgtc ggcgcgcagg acgtggtcca gcatggcact    900
gagcagaaca atcctttccc ggaggcagat gagaagattt tcgtcgtatc ggccaccggt    960
gaaagccaga tgctcacgcg cgggcaactg aaggaataca ttggccagca gcgcggcgag   1020
ggctatgtct tctacgagaa ccgtgcatac ggcgtggcgg ggaaaagcct gttcgacgat   1080
gggctgggag ccgcgcccgg cgtgccgagc ggacgttcga agttctcgcc ggatgtactg   1140
gaaacggtgc cggcgtcacc cggattgcgg cggccgtcgc tgggcgcagt ggaacgccag   1200
gattccggct atgacagcct tgatggggtg ggatcgcgat cgttctcgtt gggcgaggtg   1260
tccgacatgg ccgccgtgga agcggcggaa ctggaaatga cccggcaagt cttgcacgcc   1320
ggggcgcggc aggacgatgc cgagccgggc gtgagcggtg cgtcggcgca ctgggggcag   1380
```

```
cgggcgctgc agggcgccca ggcggtggcg gcggcgcagc ggctggttca tgccattgcc    1440
ctgatgacgc aattcggccg ggccggttcc accaacacgc cgcaggaagc ggcctcgttg    1500
tcggcggccg tgttcggctt gggcgaggcc agcagcgccg tggccgaaac cgtgagcggt    1560
tttttccgcg ggtcttcgcg ctgggccggc ggtttcggcg tggctggcgg cgcgatggcg    1620
ctgggaggcg gcatcgccgc ggccgttggc gccgggatgt cgttgaccga tgacgcgccg    1680
gccggacaga aggccgccgc cggcgccgag atcgcgctgc agttgacagg tggaacggtc    1740
gagctggctt cttccatcgc gttggcgctg gccgcggcgc gcggcgtgac cagcggcttg    1800
caggtggccg gggcgtcggc cggggcggct gccggcgcat tggccgcggc gctcagtccc    1860
atggagatct acggcctggt gcagcaatcg cactatgcgg atcagctgga caagctggcg    1920
caggaatcga gcgcatacgg ttacgagggc gacgccttgc tggcccagct gtatcgcgac    1980
aagacggccg ccgagggcgc cgtcgccggc gtctccgccg tcctgagcac ggtgggggcg    2040
gcggtgtcga tcgccgcggc ggccagcgtg gtagggccc cggtggcggt ggtcacttcc    2100
ttgctgaccg gggctctcaa cggcatcctg cgcggcgtgc agcagcccat catcgaaaag    2160
ctggccaacg attacgctcg caagatcgac gagctgggcg ggccgcaagc gtacttcgag    2220
aaaaacctgc aggcgcgtca cgaacaactg gccaattcgg acggcctacg gaaaatgctg    2280
gccgacctgc aggccggttg gaacgccagc agcgtgatcg gggtgcagac gacagagatc    2340
tccaagtcgg cgctcgaact ggccgccatt accggcaacg cggacaacct gaaatccgtc    2400
gacgtgttcg tggaccgctt cgtccagggc gagcgggtgg ccggccagcc ggtggtcctc    2460
gacgtcgccg ccggcggcat cgatatcgcc agccgcaagg gcgagcggcc ggcgctgacg    2520
ttcatcacgc cgctggccgc gccaggagaa gagcagcgcc ggcgcacgaa acgggcaag    2580 agcgaattca ccacattcgt cgagatcgtg ggcaagcagg accgctggcg catccgggac    2640
ggcgcggccg acaccaccat cgatctggcc aaggtggtgt cgcaactggt cgacgccaat    2700
ggcgtgctca agcacagcat caaactggat gtgatcggcg gagatggcga tgacgtcgtg    2760
cttgccaatg cttcgcgcat ccattatgac ggcggcgcgg gcaccaacac ggtcagctat    2820
gccgccctgg gtcgacagga ttccattacc gtgtccgccg acggggaacg tttcaacgtg    2880
cgcaagcagt tgaacaacgc caacgtgtat cgcgaaggcg tggctaccca gacaaccgcc    2940
tacggcaagc gcacggagaa tgtccaatac cgccatgtcg agctggcccg tgtcgggcaa    3000
ctggtggagg tcgacacgct cgagcatgtg cagcacatca tcggcggggc cggcaacgat    3060
tcgatcaccg gcaatgcgca cgacaacttc ctagccggcg ggtcgggcga cgacaggctg    3120
gatggcggcg ccggcaacga caccctggtt ggcggcgagg gccaaaacac ggtcatcggc    3180
ggcgccggcg acgacgtatt cctgcaggac ctggggggtat ggagcaacca gctcgatggc    3240
ggcgcgggcg tcgataccgt gaagtacaac gtgcaccagc cttccgagga gcgcctcgaa    3300
cgcatgggcg acacgggcat ccatgccgat cttcaaaagg gcacggtcga gaagtggccg    3360
gccctgaacc tgttcagcgt cgaccatgtc aagaatatcg agaatctgca cggctcccgc    3420
ctgaacgacc gcatcgccgg cgacgaccag gacaacgagc tctggggcca cgatggcaac    3480
gacacgatac gcgccggggg cggcgacgac atcctgcgcg gcggcctggg cctgacacg    3540 ctgtatggcg aggacggcaa cgacatcttc ctgcaggacg acgagaccgt cagcgatgac    3600
atcgacggcg gcgcggggct ggacaccgtc gactactccg ccatgatcca tccaggcagg    3660
atcgttgcgc cgcatgaata cggcttcggg atcgaggcgg acctgtccag ggaatgggtg    3720
```

```
cgcaaggcgt ccgcgctggg cgtggactat tacgataatg tccgcaatgt cgaaaacgtc     3780
atcggtacga gcatgaagga tgtgctcatc ggcgacgcgc aagccaatac cctgatgggc     3840
cagggcggcg acgataccgt gcgcggcggc gacggcgatg atctgctgtt cggcggcgac     3900
ggcaacgaca tgctgtatgg cgacgccggc aacgacaccc tctacggggg gctgggcgac     3960
gatacccttg aaggcggcgc gggcaacgat tggttcggcc agacgcaggc gcgcgagcat     4020
gacgtgctgc gcggcggaga tggggtggat accgtcgatt acagccagac cggcgcgcat     4080
gccggcattg ccgcgggtcg catcgggctg gcatcctgg ctgacctggg cgccggccgc      4140
gtcgacaagc tgggcgaggc cggcagcagc gcctacgata cggtttccgg tatcgagaac     4200
gtggtgggca cggaactggc cgaccgcatc acgggcgatg cgcaggccaa cgtgctgcgc     4260
ggcgcgggtg cgccgacgt gcttgcgggc ggcgagggcg acgatgtgct gctgggcggc      4320
gacggcgacg accagctgtc gggcgacgcc ggacgcgatc gcttgtacgg cgaagccggt     4380
gacgactggt tcttccagga tgccgccaat gccggcaatc tgctcgacgg cggcgacggc     4440
cgcgataccg tggatttcag cggcccgggc cggggcctcg acgccggcgc aaagggcgta     4500
ttcctgagct tgggcaaggg gttcgccagc ctgatggacg aacccgaaac cagcaacgtg     4560
ttgcgcaata tcgagaacgc cgtgggcagc gcgcgtgatg acgtgctgat cggcgacgca     4620
ggcgccaacg tcctcaatgg cctgcgggc aacgacgtgc tgtccggcgg cgctggcgac      4680
gatgtgctgc tgggcgacga gggctcggac ctgctcagcg gcgatgcggg caacgacgat     4740
ctgttcggcg ggcagggcga tgatacttat ctgttcgggg tcgggtacgg gcacgacacg     4800
atctacgaat cgggcggcgg ccatgacacc atccgcatca acgcggggc ggaccagctg      4860 tggttcgcgc gccagggcaa cgacctggag atccgcattc tcggcaccga cgatgcactt     4920
accgtgcacg actggtatcg cgacgccgat caccgggtgg aaatcatcca tgccgccaac     4980
caggcggtag accaggcagg catcgaaaag ctggtcgagg caatggcgca gtatccggac     5040
cccggcgcgg cggcggctgc cccgccggcg gcgcgcgtgc cggacacgct gatgcagtcc     5100
ctggctgtca actggcgctg a                                              5121
```

<210> SEQ ID NO 5
<211> LENGTH: 5223
<212> TYPE: DNA
<213> ORGANISM: Bordetella parapertussis
<220> FEATURE:
<221> NAME/KEY: misc_feature
<223> OTHER INFORMATION: Nucleotide sequence of adenylate cyclase (CyaA) gene

<400> SEQUENCE: 5
gtgctggatg tttggttctt gcagaaggat gaggttctga gcgctacaca ccggttgcgt 60
cggtgcgaat ccgttcaatc gactacttat cgacagatcc acatgcagca atcgcatcag 120
gctggttacg caaacgccgc cgaccgggag tctggcatcc ccgcagccgt actcgatggc 180
atcaaggccg tggcgaagga aaaaaacgcc acattgatgt tccgcctggt caaccccat 240 tccaccagcc tgattgccga aggggtggcc accaaaggat tgggcgtgca cgccaagtcg 300
tccgattggg ggttgcaggc gggctacatt cccgtcaacc cgaatctttc caaactgttc 360
ggccgtgcgc ccgaggtgat cgcgcgggcc gacaacgacg tcaacagcag cctggcgcat 420
ggccataccg cggtcgacct gacgctgtcg aaagagcggc ttgactatct gcggcaagcg 480
ggcctggtca ccggcatggc cgatggcgtg gtcgcgagca accacgcagg ctacgagcag 540
ttcgagtttc gcgtgaagga aacctcggac gggcgctatg ccgtgcagta tcgccgcaag 600

```
ggcggcgacg atttcgaggc ggtcaaggtg atcggcaatg ccgccggtat tccactgacg      660
gcggatatcg acatgttcgc catcatgccg catctgtcca acttccgcga ctcggcgcgc      720
agttcggtga ccagcggcga ttcggtgacc gattacctgg cgcgcacgcg gcgggccgcc      780
agcgaggcca cgggcggcct ggatcgcgaa cgcatcgact tgttgtggaa aatcgctcgc      840
gccggcgccc gttccgcagt gggcaccgag gcgcgtcgcc agttccgcta cgacggcgac      900
atgaatatcg gcgtgatcac cgatttcgag ctggaagtgc gcaatgcgct gaacaggcgg      960
gcgcacgccg tcggcgcgca ggacgtggtc cagcatggca ctgagcagaa caatcctttc     1020
ccggaggcag atgagaagat tttcgtcgta tcggccaccg gtgaaagcca gatgctcacg     1080
cgcgggcaac tgaaggaata cattggccag cagcgcggcg agggctatgt cttctacgag     1140
aaccgtgcat acgcgtggc ggggaaaagc ctgttcgacg atgggctggg agccgcgccc     1200
ggcgtgccgg cggacgttc gaagtcctcg ccggatgtac tggaaacggt gccggcgtca     1260
cccggattgc ggcggccgtc gctgggcgca gtggaacgcc aggattccgg ctatgacagc     1320
cttgatgggg tgggatcgcg atcgttctcg ttgggcgagg tgtccgacat ggccgccgtg     1380
gaagcggcgg aactggaaat gacccggcaa gtcttgcacg ccggggcgcg gcaggacgat     1440
gccgagccgg gcgtgagcgg tgcgtcggcg cactgggggc agcgggcgct gcaggcgcc      1500 caggcggtgg cggcggcgca gcggctggtt catgccattg ccctgatgac gcaattcggc     1560
cgggccggtt ccaccaacac gccgcaggaa gcggcctcgt tgtcggcggc cgtgttcggc     1620
ttgggcgagg ccagcagcgc cgtggccgaa accgtgagcg gttttttccg cgggtcttcg     1680
cgctgggccg gcggtttcgg cgtggctggc ggcgcgatgg cgctgggagg cggcatcgcc     1740
gcggccgttg gcgccgggat gtcgttgacc gatgacgcgc cggccggaca gaaggccgcc     1800
gtcggcgccg agatcgcgct gcagttgaca ggtggaacgg tcgagctggc ttcttccatc     1860
gcgttggcgc tggccgcggc gcgcggcgtg accagcggct gcaggtggc ggggcgtcg      1920 gccggggcgg ctgccggcgc attggccgcg gcgctcagtc ccatggagat ctacggcctg     1980
gtgcagcaat cgcactatgc ggatcagctg gacaagctgg cgcaggaatc gagcgcatac     2040
ggttacgagg gcgacgcctt gctggcccag ctgtatcgcg acaagacggc cgccgagggc     2100
gccgtcgccg gcgtctccgc cgtcctgagc acggtggggg cggcggtgtc gatcgccgcg     2160
gcggccagcg tggtaggcgc cccggtgcg gtggtcactt ccttgttgac cggggctctc     2220
aacggcatcc tgcgcggcgt gcagcagccc atcatcgaaa agctggccaa tgattacgct     2280
cgcaagatcg acgagctggg cgggccgcaa gcgtacttcg agaaaaacct gcaggcgcgt     2340
cacgaacaac tggccaattc ggacggccta cggaaaatgc tggctgacct gcaggccggg     2400
tggaacgcca gcagcgtgat cggggtgcag acgacagaga tttccaagtc ggcgctcgaa     2460
ctggccgcca ttaccggcaa cgcggacaac ctgaaatccg ccgacgtgtt cgtggaccgc     2520
ttcatccagg gcgagcgggt ggccggccag ccggtggtac tcgacgtcgc cgccggcggc     2580
atcgatatcg ccagccgcaa gggcgagcgg ccggcgctga cgttcatcac gccgctggcc     2640
gcgccaggag aagagcagcg ccggcgcacg aagacgggca agagcgaatt caccacattc     2700
gtcgagatcg tgggcaagca ggaccgctgg cgcatccggg acggcgcggc cgacaccacc     2760
atcgatctgg ccaaggtggt gtcgcaactg gtcgacgcca atggcgtgct caagcacagc     2820
atcaaactgg aggtgatcgg cggagatggc gatgatgtcg tgcttgccaa tgcttcgcgc     2880
atccattacg acggcggcgc gggaaccaac acggtcagct atgccgccct gggccgacag     2940
```

```
gattccatta ccgtgtccgc cgacggggaa cgtttcaacg tgcgcaagca gttgaacaac      3000
gccaacgtgt atcgcgaagg cgtggctacc cagaaaaccg cctacggcaa gcgcacggag      3060
aatgtccaat accgccatgt cgagctggcc cgtgtcgggc aactggtgga ggtcgacacg      3120
ctcgagcatg tgcagcacat catcggcggg gccggcaacg attcgatcac cggcaatgcg      3180
cacgacaact tcctggccgg cggggcgggc gacgacaggc tggatggcgg cgccggcaac      3240
gacacactgg tcggcggcga gggccacaac acggtcgtcg gcggcgctgg cgacgacgta      3300
ttcctgcagg acctgggggt atggagcaac cagctcgatg gcggcgcggg cgtcgatacc      3360
gtgaagtaca acgtgcacca gccttccgag gaacgcctcg aacgcatggg cgacacgggc      3420
atccatgccg atcttcaaaa gggcacggtc gagaagtggc cggccctgaa cctgttcagc      3480
gtcgaccatg tcaagaatat cgagaatctg cacggctcca gcctgaacga cagcatcgcc      3540
ggcgacgacc gggacaacga gctctggggc gacgatggca acgacacgat acacggccgg      3600
ggcggcgacg atatcctgcg cggcggcctg ggcctggaca cgctgtatgg cgaggacggc      3660
aacgacatct tcctgcagga cgacgagacc gtcagcgatg acatcgacgg cggcgcgggg      3720
ctggacaccg tcgactattc cgccatgatc catgcaggca agatcgttgc gccgcatgaa      3780
tacggcttcg ggatcgaggc ggacctgtcc gaagggtggg tgcgcaaggc ggcccggcgc      3840
ggcatgggct actacgacag tgtccgcagt gtcgaaaacg tcatcggcac gagcatgaag      3900
gatgtgctca tcggcgacgc gcaagccaat accctgatgg gccagggcgg cgacgatacc      3960
gtgcgcggcg cgacggcga tgatctgctg ttcggcggcg acggcaacga catgctgtat      4020
ggagacgccg caacgacac cctctacgga gggctgggcg acgataccct tgaaggcggc      4080
gcgggcaacg attggttcgg ccagacgccg gcgcgcgagc atgacgtgct gcgcggcggg      4140 gctgggggtgg ataccgtgga ttacagccag gcgggcgcgc atgccggcgt tgccacgggt      4200
cgcatcgggc tgggtattct ggcggacctg ggcgccggcc gcgtcgacaa gctgggcgag      4260
gccggcagca gcgcctacga tacggtttcc ggcatcgaaa atgtggtggg cacggaactg      4320
gccgaccgca tcacgggcga tgcgcaggcc aacgtactgc gcggcgcggg tggtgccgac      4380
gtgcttgcgg gcggcgaggg cgacgatgtg ctgctgggcg gcgagggcga tgaccagctg      4440
tcgggcgacg ccggacgcga ccgcttgtac ggcgaagccg gtgacgactg gttcttccag      4500
gatgccgcca atgccggcaa tctgctcgac ggtggtgacg gcaacgatac cgtggatttc      4560
agcggcccgg gccggggcct cgacgccggc gcaaagggcg tattcctgag cctgggcaag      4620
gggttcgcca gcctgatgga cgaacccgaa accagcaacg tgttgcgcca tatcgagaac      4680
gccgtgggca gcgtgcgtga tgacgtgctg atcggcgacg caggcgccaa cgtcctcaat      4740
ggcctggcgg gcaacgacgt gttgtccggc ggcgccggcg acgatgtgct gctgggcgac      4800
gagggctcgg acctgctcag cggcgatgcg ggcaacgacg atctgttcgg cgggcagggc      4860 gatgataccct atctgttcgg ggccgggtac ggacatgaca cgatctacga atcgggcggc      4920
ggccatgaca ccatccgtat caacgcgggg gcggaccagc tgtggtttgc gcgccagggc      4980
aacgacctgg agatccgcat tcttggcacc gacgatgcac ttaccgtgca cgactggtat      5040
cgcgacgccg atcaccgggt ggaagccatc catgccgcca accaggccat agacccggcc      5100
ggcatcgaaa agctggtcga ggcaatggcg cagtacccgg accccggcgc ggcggcggct      5160
gccccgccgg cggcgcgcgt gccggacacg ctgatgcagt ccctggctgt caactggcgc      5220
tga                                                                   5223
```

<210> SEQ ID NO 6
<211> LENGTH: 5223
<212> TYPE: DNA
<213> ORGANISM: Bordetella bronchiseptica
<220> FEATURE:
<221> NAME/KEY: misc_feature
<223> OTHER INFORMATION: Nucleotide sequence of adenylate cyclase (CyaA) gene

<400> SEQUENCE: 6

```
gtgctggatg tttggttctt gcagaaggat gaggttctga gcgctacaca ccggttgcgt     60
cggtgcgaat ccgttcaatc gactacttat cgacagatcc acatgcagca atcgcatcag    120
gctggttacg caaacgccgc cgaccgggag tctggcatcc ccgcagccgt actcgatggc    180
atcaaggccg tggcgaagga aaaaaacgcc acattgatgt tccgcctggt caaccccat    240
tccaccagcc tgattgccga aggggtggcc accaaaggat tgggcgtgca cgccaagtcg    300
tccgattggg ggttgcaggc gggctacatt cccgtcaacc cgaatctttc caaactgttc    360
ggccgtgcgc ccgaggtgat cgcgcgggcc gacaacgacg tcaacagcag cctggcgcat    420
ggccataccg cggtcgacct gacgctgtcg aaagagcggc ttgactatct gcggcaagcg    480
ggcctggtca ccggcatggc cgatggcgtg gtcgcgagca accacgcagg ctacgagcag    540
ttcgagtttc gcgtgaagga aacctcggac gggcgctatg ccgtgcagta tcgccgcaag    600
ggcggcgacg atttcgaggc ggtcaaggtg atcggcaatg ccgccggtat tccactgacg    660
gcggatatcg acatgttcgc catcatgccg catctgtcca acttccgcga ctcggcgcgc    720
agttcggtga ccagcggcga ttcggtgacc gattacctgg cgcgcacgcg gcgggccgcc    780
agcgaggcca cgggcggcct ggatcgcgaa cgcatcgact tgttgtggaa aatcgctcgc    840
gccggcgccc gttccgcagt gggcaccgag gcgcgtcgcc agttccgcta cgacggcgac    900
atgaatatcg gcgtgatcac cgatttcgag ctggaagtgc gcaatgcgct gaacaggcgg    960
gcgcacgccg tcggcgcgca ggacgtggtc cagcatggca ctgagcagaa caatcctttc   1020
ccggaggcag atgagaagat tttcgtcgta tcggccaccg gtgaaagcca gatgctcacg   1080
cgcgggcaac tgaaggaata cattggccag cagcgcggcg agggctatgt cttctacgag   1140
aaccgtgcgt acggcgtggc ggggaaaagc ctgttcgacg atgggctggg agccgcgccc   1200
ggcgtgccgg gcggacgttc gaagtcctcg ccggatgtac tggaaacggt gccggcgtca   1260
cccggattgc ggcggccgtc gctgggcgca gtggaacgcc aggattccgg ctatgacagc   1320
cttgatgggg tgggatcgcg atcgttctcg ttgggcgagg tgtccgacat ggccgccgtg   1380
gaagcggcgg aactggaaat gacccggcaa gtcttgcacg ccggggcgcg gcaggacgat   1440
gccgagccgg gcgtgagcgg tgcgtcggcg cactgggggc agcgggcgct gcagggcgcc   1500
caggcggtgg cggcggcgca gcggctggtt catgccattg ccctgatgac gcaattcggc   1560
cgggccggtt ccaccaacac gccgcaggaa gcggcctcgt tgtcggcggc cgtgttcggc   1620
ttgggcgagg ccagcagcgc cgtggccgaa accgtgagcg gtttttccg cgggtcttcg   1680
cgctgggccg gcggtttcgg cgtggctggc ggcgcgatgg cgctgggagg cggcatcgcc   1740
gcggccgttg gcgccgggat gtcgttgacc gatgacgcgc cggccggaca gaaggccgcc   1800
gccggcgccg agatcgcgct gcagttgaca ggtggaacgg tcgagctggc ttcttccatc   1860
gcgttggcgc tggccgcggc gcgcggcgtg accagcggct tgcaggtggc gggggcgtcg   1920
gccggggcgg ctgccggcgc attggccgcg gcgctcagtc ccatggagat ctacggcctg   1980
gtgcagcaat cgcactatgc ggatcagctg gacaagctgg cgcaggaatc gagcgcatac   2040
```

-continued

```
ggttacgagg gcgacgcctt gctggcccag ctgtatcgcg acaagacggc cgccgagggc      2100
gccgtcgccg gcgtctccgc cgtcctgagc acggtggggg ctgcggtgtc gatcgccgcg      2160
gcggccagcg tggtaggcgc cccggtggcg gtggtcactt ccttgttgac cggggctctc      2220
aacggcatcc tgcgcggcgt gcagcagccc atcatcgaaa agctggccaa tgattacgct      2280
cgcaagatcg acgagctggg cgggccgcaa gcgtacttcg agaaaaacct gcaggcgcgt      2340
cacgaacaac tggccaattc ggacggccta cggaaaatgc tggccgacct gcaggccggg      2400
tggaacgcca gcagcgtgat cggggtgcag acgacagaga tttccaagtc ggcgctcgaa      2460
ctggccgcca ttaccggcaa cgcggacaac ctgaaatccg ccgacgtgtt cgtggaccgc      2520
ttcatccagg gcgagcgggt ggccggccag ccggtggtac tcgacgtcgc cgccggcggc      2580
atcgatatcg ccagccgcaa gggcgagcgg ccggcgctga cgttcatcac gccgctggcc      2640
gcgccaggag aagagcagcg ccggcgcacg aaaacgggca agagcgaatt caccacattc      2700
gtcgagatcg tgggcaagca ggaccgctgg cgcatccggg acggcgcggc cgacaccacc      2760
atcgatctgg ccaaggtggt gtcgcaactg gtcgacgcca atggcgtgct caagcacagc      2820
atcaaactgg aggtgatcgg cggagatggc gatgatgtcg tgcttgccaa tgcttcgcgc      2880
atccattacg acggcggcgc gggaaccaac acggtcagct atgccgccct gggccgacag      2940
gattccatta ccgtgtccgc cgacggggaa cgtttcaacg tgcgcaagca gttgaacaac      3000
gccaacgtgt atcgcgaagg cgtggctacc cagaaaaccg cctacggcaa gcgcacggag      3060
aatgtccaat accgccatgt cgagctggcc cgtgtcgggc aactggtgga ggtcgacacg      3120
ctcgagcatg tgcagcacat catcggcggg gccggcaacg attcgatcac cggcaatgcg      3180
cacgacaact tcctggccgg cggggcgggc gacgacaggc tggatggcgg cgccggcaac      3240
gacacactgg tcgcggcga gggccacaac acggtcgtcg gcggcgctgg cgacgacgta      3300
ttcctgcagg acctgggggt atggagcaac cagctcgatg gcggcgcggg cgtcgatacc      3360
gtgaagtaca acgtgcacca gccttccgag gaacgcctcg aacgcatggg cgacacgggc      3420
atccatgccg atcttcaaaa gggcacggtc gagaagtggc cggccctgaa cctgttcagc      3480
gtcgaccatg tcaagaatat cgagaatctg cacggctcca gcctgaacga cagcatcgcc      3540
ggcgacgacc gggacaacga gctctggggc gacgatggca acgacacgat acacggccgg      3600
ggcggcgacg atatcctgcg cggcggcctg ggcctggaca cgctgtatgg cgaggacggc      3660
aacgacatct tcctgcagga cgacgagacc gtcagcgatg acatcgacgg tggcgcggga      3720
ctggacaccg tcgactattc cgccatgatc catgcaggca agatcgttgc gccgcatgaa      3780
tacggcttcg ggatcgaggc ggacctgtcc gaagggtggg tgcgcaaggc ggcccggcgc      3840
ggcatggact actacgacag tgtccgcagt gtcgaaaacg tcatcggcac gagcatgaag      3900
gatgtgctca tcggcgacgc gcaagccaat accctgatgg gccagggcgg cgacgatacc      3960
gtgcgcggcg gcgacggcga tgatctgctg ttcggcggcg acggcaacga catgctgtat      4020
ggagacgccg gcaacgacac cctctacgga gggctgggcg acgataccct tgaaggcggc      4080
gcgggcaacg attggttcgg ccagacgccg gcgcgcgagc atgacgtgct gcgcggcggg      4140
gctggggtgg ataccgtgga ttacagccag gcgggcgcgc atgccggcgt tgccacgggt      4200
cgcatcgggc tgggtattct ggcggacctg ggcgccggcc gcgtcgacaa gctgggcgag      4260
gccggcagca gcgcctacga tacggtttcc ggcatcgaaa atgtggtggg cacggaactg      4320
gccgaccgca tcacgggcga tgcgcaggcc aacgtactgc gcggcgcggg tggcgccgac      4380
gtgcttgcgg gcggcgaggg cgacgatgtg ctgctgggcg gcgacggcga cgaccagctg      4440
```

```
tcgggcgacg ccggacgcga ccgcttgtac ggcgaagccg gtgacgactg gttcttccag    4500
gatgccgcca atgccggcaa tctgctcgac ggtggtgacg gcaacgatac cgtggatttc    4560
agcggcccgg gccggggcct cgacgccggc gcaaagggcg tattcctgag cctgggcaag    4620
gggttcgcca gcctgatgga cgaacccgaa accagcaacg tgttgcgcca tatcgagaac    4680
gccgtgggca gcgtgcgtga tgacgtgctg atcggcgacg caggcgccaa cgtcctcaat    4740
ggcctggcgg gcaacgacgt gctgtccggc ggcgccggcg acgatgtgct gctgggcgac    4800
gagggctcgg acctgctcag cggcgatgcg ggcaacgacg atctgttcgg cgggcagggc    4860
gatgatacct atctgttcgg ggccgggtac ggacatgaca cgatctacga atcgggcggc    4920
ggccatgaca ccatccgtat caacgcgggg gcggaccagc tgtggtttgc gcgccagggc    4980
aacgacctgg agatccgcat tcttggcacc gacgatgcac ttaccgtgca cgactggtat    5040
cgcgacgccg atcaccgggt ggaagccatc catgccgcca accaggccat agacccggcc    5100
ggcatcgaaa agctggtcga ggcaatggcg cagtacccgg accccggcgc ggcggcggct    5160
gccccgccgg cggcgcgcgt gccggacacg ctgatgcagt ccctggctgt caactggcgc    5220
tga                                                                  5223

<210> SEQ ID NO 7
<211> LENGTH: 1872
<212> TYPE: PRT
<213> ORGANISM: Artificial Sequence
<220> FEATURE:
<223> OTHER INFORMATION: Synthetic construct: CyaA - mage A3 vector

<400> SEQUENCE: 7

Met Gln Gln Ser His Gln Ala Gly Tyr Ala Asn Ala Ala Asp Arg Glu
1               5                   10                  15

Ser Gly Ile Pro Ala Ala Val Leu Asp Gly Ile Lys Ala Val Ala Lys
            20                  25                  30

Glu Lys Asn Ala Thr Leu Met Phe Arg Leu Val Asn Pro His Ser Thr
        35                  40                  45

Ser Leu Ile Ala Glu Gly Val Ala Thr Lys Gly Leu Gly Val His Ala
    50                  55                  60

Lys Ser Ser Asp Trp Gly Leu Gln Ala Gly Tyr Ile Pro Val Asn Pro
65              70                  75                  80

Asn Leu Ser Lys Leu Phe Gly Arg Ala Pro Glu Val Ile Ala Arg Ala
                85                  90                  95

Asp Asn Asp Val Asn Ser Ser Leu Ala His Gly His Thr Ala Val Asp
            100                 105                 110

Leu Thr Leu Ser Lys Glu Arg Leu Asp Tyr Leu Arg Gln Ala Gly Leu
        115                 120                 125

Val Thr Gly Met Ala Asp Gly Val Val Ala Ser Asn His Ala Gly Tyr
    130                 135                 140

Glu Gln Phe Glu Phe Arg Val Lys Glu Thr Ser Asp Gly Arg Tyr Ala
145                 150                 155                 160

Val Gln Tyr Arg Arg Lys Gly Gly Asp Asp Phe Glu Ala Val Lys Val
                165                 170                 175

Ile Gly Asn Ala Ala Gly Ile Pro Leu Thr Ala Asp Leu Gln Ile Asp
            180                 185                 190

Met Phe Ala Ile Met Pro His Leu Ser Asn Phe Arg Asp Ser Ala Arg
        195                 200                 205

Ser Ser Val Thr Ser Gly Asp Ser Val Thr Asp Tyr Leu Ala Arg Thr
```

```
             210                 215                 220
Arg Arg Ala Ser Thr Phe Pro Asp Leu Glu Ser Glu Phe Gln Ala Ala
225                 230                 235                 240

Leu Ser Arg Lys Val Ala Glu Leu Val His Phe Leu Leu Leu Lys Tyr
                245                 250                 255

Arg Ala Arg Glu Pro Val Thr Lys Ala Glu Met Leu Gly Ser Val Val
            260                 265                 270

Gly Asn Trp Gln Tyr Phe Phe Pro Val Ile Phe Ser Lys Ala Ser Ser
        275                 280                 285

Ser Leu Gln Leu Val Phe Gly Ile Glu Leu Met Glu Val Asp Pro Ile
    290                 295                 300

Gly His Leu Tyr Ile Phe Gly Thr Arg Ala Arg Leu Lys Leu Leu Trp
305                 310                 315                 320

Lys Ile Ala Arg Ala Gly Ala Arg Ser Ala Val Gly Thr Glu Ala Arg
                325                 330                 335

Arg Gln Phe Arg Tyr Asp Gly Asp Met Asn Ile Gly Val Ile Thr Asp
            340                 345                 350

Phe Glu Leu Glu Val Arg Asn Ala Leu Asn Arg Arg Ala His Ala Val
        355                 360                 365

Gly Ala Gln Asp Val Val Gln His Gly Thr Glu Gln Asn Asn Pro Phe
    370                 375                 380

Pro Glu Ala Asp Glu Lys Ile Phe Val Val Ser Ala Thr Gly Leu Gly
385                 390                 395                 400

Asp Asn Gln Ile Met Pro Lys Ala Gly Leu Leu Ile Ile Val Leu Ala
                405                 410                 415

Ile Ile Ala Arg Glu Gly Asp Cys Ala Pro Glu Glu Lys Ile Pro Lys
            420                 425                 430

Lys Leu Leu Thr Gln His Phe Val Gln Glu Asn Tyr Leu Glu Tyr Arg
        435                 440                 445

Gln Val Pro Gly Ser Asp Pro Ala Cys Tyr Glu Phe Leu Trp Gly Pro
    450                 455                 460

Arg Ala Leu Val Glu Thr Ser Tyr Val Lys Val Leu His His Met Val
465                 470                 475                 480

Lys Ile Ser Gly Thr Ser Glu Ser Gln Met Leu Thr Arg Gly Gln Leu
                485                 490                 495

Lys Glu Tyr Ile Gly Gln Gln Arg Gly Glu Gly Tyr Val Phe Tyr Glu
            500                 505                 510

Asn Arg Ala Tyr Gly Val Ala Gly Lys Ser Leu Phe Asp Asp Gly Leu
        515                 520                 525

Gly Ala Ala Pro Gly Val Pro Ser Gly Arg Ser Lys Phe Ser Pro Asp
    530                 535                 540

Val Leu Glu Thr Val Pro Ala Ser Pro Gly Leu Arg Arg Pro Ser Leu
545                 550                 555                 560

Gly Ala Val Glu Arg Gln Asp Ser Gly Tyr Asp Ser Leu Asp Gly Val
                565                 570                 575

Gly Ser Arg Ser Phe Ser Leu Gly Glu Val Ser Asp Met Ala Ala Val
            580                 585                 590

Glu Ala Ala Glu Leu Glu Met Thr Arg Gln Val Leu His Ala Gly Ala
        595                 600                 605

Arg Gln Asp Asp Ala Glu Pro Gly Val Ser Gly Ala Ser Ala His Trp
    610                 615                 620

Gly Gln Arg Ala Leu Gln Gly Ala Gln Ala Val Ala Ala Ala Gln Arg
625                 630                 635                 640
```

-continued

```
Leu Val His Ala Ile Ala Leu Met Thr Gln Phe Gly Arg Ala Gly Ser
            645                 650                 655
Thr Asn Thr Pro Gln Glu Ala Ala Ser Leu Ser Ala Ala Val Phe Gly
                660                 665                 670
Leu Gly Glu Ala Ser Ser Ala Val Ala Glu Thr Val Ser Gly Phe Phe
            675                 680                 685
Arg Gly Ser Ser Arg Trp Ala Gly Gly Phe Gly Val Ala Gly Gly Ala
690                 695                 700
Met Ala Leu Gly Gly Gly Ile Ala Ala Val Gly Ala Gly Met Ser
705                 710                 715                 720
Leu Thr Asp Asp Ala Pro Ala Gly Gln Lys Ala Ala Gly Ala Glu
            725                 730                 735
Ile Ala Leu Gln Leu Thr Gly Gly Thr Val Glu Leu Ala Ser Ser Ile
            740                 745                 750
Ala Leu Ala Leu Ala Ala Arg Gly Val Thr Ser Gly Leu Gln Val
            755                 760                 765
Ala Gly Ala Ser Ala Gly Ala Ala Gly Ala Leu Ala Ala Ala Leu
            770                 775                 780
Ser Pro Met Glu Ile Tyr Gly Leu Val Gln Gln Ser His Tyr Ala Asp
785                 790                 795                 800
Gln Leu Asp Lys Leu Ala Gln Glu Ser Ser Ala Tyr Gly Tyr Glu Gly
                805                 810                 815
Asp Ala Leu Leu Ala Gln Leu Tyr Arg Asp Lys Thr Ala Ala Glu Gly
            820                 825                 830
Ala Val Ala Gly Val Ser Ala Val Leu Ser Thr Val Gly Ala Ala Val
            835                 840                 845
Ser Ile Ala Ala Ala Ser Val Val Gly Ala Pro Val Ala Val Val
850                 855                 860
Thr Ser Leu Leu Thr Gly Ala Leu Asn Gly Ile Leu Arg Gly Val Gln
865                 870                 875                 880
Gln Pro Ile Ile Glu Lys Leu Ala Asn Asp Tyr Ala Arg Lys Ile Asp
                885                 890                 895
Glu Leu Gly Gly Pro Gln Ala Tyr Phe Glu Lys Asn Leu Gln Ala Arg
            900                 905                 910
His Glu Gln Leu Ala Asn Ser Asp Gly Leu Arg Lys Met Leu Ala Asp
            915                 920                 925
Leu Gln Ala Gly Trp Asn Ala Ser Ser Val Ile Gly Val Gln Thr Thr
            930                 935                 940
Glu Ile Ser Lys Ser Ala Leu Glu Leu Ala Ala Ile Thr Gly Asn Ala
945                 950                 955                 960
Asp Asn Leu Lys Ser Val Asp Val Phe Val Asp Arg Phe Val Gln Gly
                965                 970                 975
Glu Arg Val Ala Gly Gln Pro Val Val Leu Asp Val Ala Ala Gly Gly
            980                 985                 990
Ile Asp Ile Ala Ser Arg Lys Gly  Glu Arg Pro Ala Leu  Thr Phe Ile
            995                 1000                1005
Thr Pro  Leu Ala Ala Pro Gly  Glu Glu Gln Arg Arg  Arg Thr Lys
            1010                1015                1020
Thr Gly  Lys Ser Glu Phe Thr  Thr Phe Val Glu Ile  Val Gly Lys
            1025                1030                1035
Gln Asp  Arg Trp Arg Ile Arg  Asp Gly Ala Ala Asp  Thr Thr Ile
            1040                1045                1050
```

```
Asp Leu Ala Lys Val Val Ser Gln Leu Val Asp Ala Asn Gly Val
    1055                1060                1065

Leu Lys His Ser Ile Lys Leu Asp Val Ile Gly Gly Asp Gly Asp
    1070                1075                1080

Asp Val Val Leu Ala Asn Ala Ser Arg Ile His Tyr Asp Gly Gly
    1085                1090                1095

Ala Gly Thr Asn Thr Val Ser Tyr Ala Ala Leu Gly Arg Gln Asp
    1100                1105                1110

Ser Ile Thr Val Ser Ala Asp Gly Glu Arg Phe Asn Val Arg Lys
    1115                1120                1125

Gln Leu Asn Asn Ala Asn Val Tyr Arg Glu Gly Val Ala Thr Gln
    1130                1135                1140

Thr Thr Ala Tyr Gly Lys Arg Thr Glu Asn Val Gln Tyr Arg His
    1145                1150                1155

Val Glu Leu Ala Arg Val Gly Gln Leu Val Glu Val Asp Thr Leu
    1160                1165                1170

Glu His Val Gln His Ile Ile Gly Gly Ala Gly Asn Asp Ser Ile
    1175                1180                1185

Thr Gly Asn Ala His Asp Asn Phe Leu Ala Gly Gly Ser Gly Asp
    1190                1195                1200

Asp Arg Leu Asp Gly Gly Ala Gly Asn Asp Thr Leu Val Gly Gly
    1205                1210                1215

Glu Gly Gln Asn Thr Val Ile Gly Gly Ala Gly Asp Asp Val Phe
    1220                1225                1230

Leu Gln Asp Leu Gly Val Trp Ser Asn Gln Leu Asp Gly Gly Ala
    1235                1240                1245

Gly Val Asp Thr Val Lys Tyr Asn Val His Gln Pro Ser Glu Glu
    1250                1255                1260

Arg Leu Glu Arg Met Gly Asp Thr Gly Ile His Ala Asp Leu Gln
    1265                1270                1275

Lys Gly Thr Val Glu Lys Trp Pro Ala Leu Asn Leu Phe Ser Val
    1280                1285                1290

Asp His Val Lys Asn Ile Glu Asn Leu His Gly Ser Arg Leu Asn
    1295                1300                1305

Asp Arg Ile Ala Gly Asp Asp Gln Asp Asn Glu Leu Trp Gly His
    1310                1315                1320

Asp Gly Asn Asp Thr Ile Arg Gly Arg Gly Gly Asp Asp Ile Leu
    1325                1330                1335

Arg Gly Gly Leu Gly Leu Asp Thr Leu Tyr Gly Glu Asp Gly Asn
    1340                1345                1350

Asp Ile Phe Leu Gln Asp Asp Glu Thr Val Ser Asp Asp Ile Asp
    1355                1360                1365

Gly Gly Ala Gly Leu Asp Thr Val Asp Tyr Ser Ala Met Ile His
    1370                1375                1380

Pro Gly Arg Ile Val Ala Pro His Glu Tyr Gly Phe Gly Ile Glu
    1385                1390                1395

Ala Asp Leu Ser Arg Glu Trp Val Arg Lys Ala Ser Ala Leu Gly
    1400                1405                1410

Val Asp Tyr Tyr Asp Asn Val Arg Asn Val Glu Asn Val Ile Gly
    1415                1420                1425

Thr Ser Met Lys Asp Val Leu Ile Gly Asp Ala Gln Ala Asn Thr
    1430                1435                1440

Leu Met Gly Gln Gly Gly Asp Asp Thr Val Arg Gly Gly Asp Gly
```

```
              1445                1450                1455

Asp Asp Leu Leu Phe Gly Gly Asp Gly Asn Asp Met  Leu Tyr Gly
        1460                1465                1470

Asp Ala Gly Asn Asp Thr Leu Tyr Gly Gly Leu Gly  Asp Asp Thr
        1475                1480                1485

Leu Glu Gly Gly Ala Gly Asn Asp Trp Phe Gly Gln  Thr Gln Ala
        1490                1495                1500

Arg Glu His Asp Val Leu Arg Gly Gly Asp Gly Val  Asp Thr Val
        1505                1510                1515

Asp Tyr Ser Gln Thr Gly Ala His Ala Gly Ile Ala  Ala Gly Arg
        1520                1525                1530

Ile Gly Leu Gly Ile Leu Ala Asp Leu Gly Ala Gly  Arg Val Asp
        1535                1540                1545

Lys Leu Gly Glu Ala Gly Ser Ser Ala Tyr Asp Thr  Val Ser Gly
        1550                1555                1560

Ile Glu Asn Val Val Gly Thr Glu Leu Ala Asp Arg  Ile Thr Gly
        1565                1570                1575

Asp Ala Gln Ala Asn Val Leu Arg Gly Ala Gly Gly  Ala Asp Val
        1580                1585                1590

Leu Ala Gly Gly Glu Gly Asp Asp Val Leu Leu Gly  Gly Asp Gly
        1595                1600                1605

Asp Asp Gln Leu Ser Gly Asp Ala Gly Arg Asp Arg  Leu Tyr Gly
        1610                1615                1620

Glu Ala Gly Asp Asp Trp Phe Phe Gln Asp Ala Ala  Asn Ala Gly
        1625                1630                1635

Asn Leu Leu Asp Gly Gly Asp Gly Arg Asp Thr Val  Asp Phe Ser
        1640                1645                1650

Gly Pro Gly Arg Gly Leu Asp Ala Gly Ala Lys Gly  Val Phe Leu
        1655                1660                1665

Ser Leu Gly Lys Gly Phe Ala Ser Leu Met Asp Glu  Pro Glu Thr
        1670                1675                1680

Ser Asn Val Leu Arg Asn Ile Glu Asn Ala Val Gly  Ser Ala Arg
        1685                1690                1695

Asp Asp Val Leu Ile Gly Asp Ala Gly Ala Asn Val  Leu Asn Gly
        1700                1705                1710

Leu Ala Gly Asn Asp Val Leu Ser Gly Gly Ala Gly  Asp Asp Val
        1715                1720                1725

Leu Leu Gly Asp Glu Gly Ser Asp Leu Leu Ser Gly  Asp Ala Gly
        1730                1735                1740

Asn Asp Asp Leu Phe Gly Gly Gln Gly Asp Asp Thr  Tyr Leu Phe
        1745                1750                1755

Gly Val Gly Tyr Gly His Asp Thr Ile Tyr Glu Ser  Gly Gly Gly
        1760                1765                1770

His Asp Thr Ile Arg Ile Asn Ala Gly Ala Asp Gln  Leu Trp Phe
        1775                1780                1785

Ala Arg Gln Gly Asn Asp Leu Glu Ile Arg Ile Leu  Gly Thr Asp
        1790                1795                1800

Asp Ala Leu Thr Val His Asp Trp Tyr Arg Asp Ala  Asp His Arg
        1805                1810                1815

Val Glu Ile Ile His Ala Ala Asn Gln Ala Val Asp  Gln Ala Gly
        1820                1825                1830

Ile Glu Lys Leu Val Glu Ala Met Ala Gln Tyr Pro  Asp Pro Gly
        1835                1840                1845
```

```
Ala Ala  Ala Ala Ala Pro Pro  Ala Ala Arg Val Pro  Asp Thr Leu
    1850             1855                 1860

Met Gln  Ser Leu Ala Val Asn  Trp Arg
    1865             1870

<210> SEQ ID NO 8
<211> LENGTH: 86
<212> TYPE: PRT
<213> ORGANISM: Artificial Sequence
<220> FEATURE:
<223> OTHER INFORMATION: Synthetic construct: MAGE A3 97-178

<400> SEQUENCE: 8

Leu Gly Asp Asn Gln Ile Met Pro Lys Ala Gly Leu Leu Ile Ile Val
1               5                  10                  15

Leu Ala Ile Ile Ala Arg Glu Gly Asp Cys Ala Pro Glu Glu Lys Ile
            20                  25                  30

Pro Lys Lys Leu Leu Thr Gln His Phe Val Gln Glu Asn Tyr Leu Glu
        35                  40                  45

Tyr Arg Gln Val Pro Gly Ser Asp Pro Ala Cys Tyr Glu Phe Leu Trp
    50                  55                  60

Gly Pro Arg Ala Leu Val Glu Thr Ser Tyr Val Lys Val Leu His His
65                  70                  75                  80

Met Val Lys Ile Ser Gly
                85

<210> SEQ ID NO 9
<211> LENGTH: 82
<212> TYPE: PRT
<213> ORGANISM: Artificial Sequence
<220> FEATURE:
<223> OTHER INFORMATION: Synthetic construct: MAGE A3 190-295

<400> SEQUENCE: 9

Thr Phe Pro Asp Leu Glu Ser Glu Phe Gln Ala Ala Leu Ser Arg Lys
1               5                  10                  15

Val Ala Glu Leu Val His Phe Leu Leu Leu Lys Tyr Arg Ala Arg Glu
            20                  25                  30

Pro Val Thr Lys Ala Glu Met Leu Gly Ser Val Val Gly Asn Trp Gln
        35                  40                  45

Tyr Phe Phe Pro Val Ile Phe Ser Lys Ala Ser Ser Ser Leu Gln Leu
    50                  55                  60

Val Phe Gly Ile Glu Leu Met Glu Val Asp Pro Ile Gly His Leu Tyr
65                  70                  75                  80

Ile Phe
```